United States Patent
Bahado-Singh

(10) Patent No.: US 11,884,980 B2
(45) Date of Patent: Jan. 30, 2024

(54) METHOD FOR DETECTION OF TRAUMATIC BRAIN INJURY

(71) Applicant: Bioscreening & Diagnostics LLC, Detroit, MI (US)

(72) Inventor: Ray Bahado-Singh, Grosse Pointe Shores, MI (US)

(73) Assignee: Bioscreening & Diagnostics LLC, Detroit, MI (US)

( * ) Notice: Subject to any disclaimer, the term of this patent is extended or adjusted under 35 U.S.C. 154(b) by 814 days.

(21) Appl. No.: 16/698,203

(22) Filed: Nov. 27, 2019

(65) Prior Publication Data

US 2020/0165680 A1     May 28, 2020

Related U.S. Application Data

(60) Provisional application No. 62/772,441, filed on Nov. 28, 2018.

(51) Int. Cl.
*C12Q 1/6883* (2018.01)
*G16B 20/20* (2019.01)
*G16B 40/00* (2019.01)

(52) U.S. Cl.
CPC .......... *C12Q 1/6883* (2013.01); *G16B 20/20* (2019.02); *G16B 40/00* (2019.02); *C12Q 2600/112* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 10,745,754 | B2 * | 8/2020 | Bahado-Singh | C12Q 1/6883 |
| 11,075,002 | B2 * | 7/2021 | Teng | G06F 16/907 |
| 2009/0203011 | A1 * | 8/2009 | Liebenberg | C12Q 1/6886 435/6.12 |
| 2020/0102610 | A1 * | 4/2020 | Bahado-Singh | C12Q 1/6883 |
| 2020/0165675 | A1 * | 5/2020 | Marsh | C12Q 1/68 |
| 2022/0260570 | A1 * | 8/2022 | Lofton-Day | G01N 33/57419 |

FOREIGN PATENT DOCUMENTS

WO      WO-2018222830 A1 * 12/2018 ............... C12Q 1/68

OTHER PUBLICATIONS

Sagarkar et al (2017) (Minimal traumatic brain injury causes persistent changes in DNA methylation at BDNF gene promoters in rat amygdala: A possible role in anxiety-like behaviors, Neurobiology of Disease, vol. 106, Oct. 2017) (Year: 2017).*

Meng et al (2017) (Traumatic Brain Injury Induces Genome-Wide Transcriptomic, Methylomic, and Network Perturbations in Brain and Blood Predicting Neurological Disorders, eBioMedicine, vol. 16, 2017) (Year: 2017).*
Molaei et al (2016) (A machine learning based approach for identifying traumatic brain injury patients for whom a head CT scan can be avoided, 2016 Annual International Conference of the IEEE Engineering in Medicine and Biology Society (EMBC)), a (Year: 2016).*
Haghighi et al (2015) (Neuronal DNA Methylation Profiling of Blast-Related Traumatic Brain Injury, Journal of Neurotrauma, vol. 32, 2015), (Year: 2015).*
Shimada-Sugimoto (2017) (Epigenome-wide association study of DNA methylation in panic disorder, Clinical Epigenetics, 9:6, 2017) (Year: 2017).*
Mallya (The manifestation of anxiety disorders after traumatic brain injury: a review, journal of neurotrauma, vol. 32, 2015) (Year: 2015).*
Molaei et al (2016) (A machine learning based approach for identifying traumatic brain injury patients for whom a head CT scan can be avoided, 2016 Annual International Conference of the IEEE Engineering in Medicine and Biology Society (EMBC)), (Year: 2016).*
Schneider et al (2017) (Schneider KJ, Leddy JJ, Guskiewicz KM, et al. Br J Sports Med Feb. 2017;51:930-934). (Year: 2017).*
European Office Action dated Apr. 1, 2021 for European Patent Application No. 19211893.3, a foreign counterpart to U.S. Appl. No. 16/698,203, 6 pages.
Bahado-Singh et al., "Artificial Intelligence and the Detection of Pediatric Concussion Using Epigenomic Analysis," Oct. 2019, Brain Research, vol. 1726, 12 pages.
Extended European Search Report dated Apr. 30, 2020 for European Patent Application No. 19211893.3, 8 pages.
Haghighi et al, "Neuronal DNA Methylation Profiling of Blast-Related Traumatic Brain Injury," Aug. 2015, Journal of Neurotrauma, 32(16): 1200-1209.
Mateen et al, "DNA Methylation: Basic Biology and Application to Traumatic Brain Injury," Aug. 2017, Journal of Neurotrauma, 34(16): 2379-2388.
Wong et al, "Epigenetic Changes Following Traumatic Brain Injury and their Implications for Outcome, Recovery and Therapy," May 2016, Neuroscience Letters, 625: 26-33.

* cited by examiner

*Primary Examiner* — Laura B Goddard
*Assistant Examiner* — Sarah A Alsomairy
(74) *Attorney, Agent, or Firm* — Lee & Hayes P.C.

(57) ABSTRACT

The present disclosure describes significant methylation changes in multiple genes and multiple metabolites in body fluid in response to TBI. Gene pathways affected included several known to be involved in neurological and brain function. A large number of good to excellent biomarkers for the detection of TBI was identified. The combination of epigenomic, clinical and metabolomic markers in different combinations overall were highly accurate for the detection of pediatric concussion using Artificial Intelligence-based techniques.

18 Claims, 3 Drawing Sheets

METHOD FOR DETECTION OF TRAUMATIC BRAIN INJURY

CROSS REFERENCE TO RELATED APPLICATIONS

This application claims the benefit of U.S. Provisional Application No. 62/772,441 filed Nov. 28, 2018, entitled "Method for Detection of TBI", which is incorporated herein by reference in its entirety.

FIELD

The present disclosure provides methods for diagnosing concussion.

BACKGROUND

Traumatic brain injury (TBI) has been reported to occur in 1.6-3.2 million Americans annually [1] and around 70-90% of these injuries are considered to be mild. Given the frequency of failed recognition and under-reporting of mild TBI (mTBI), it is estimated that its true incidence in the US is closer to 3,400,000 cases yearly, three times higher than currently reported [2]. This is an area of significant public health concern, as a marked increase in the emergency room visits has been reported over the last decade (Lumba-Brown A et al. *Centers for Disease Control and Prevention guideline on the Diagnosis and Management of mild traumatic brain injury among children, JAMA Pediatr* doi:10.1001/jamapediatrics 2018.2853.) The terms "mTBI" and "concussion" are often used interchangeably. While there are now ongoing efforts to distinguish these two conditions, the absence of distinctive symptoms, biomarkers, and consensus diagnostic criteria significantly challenges these efforts [3]. While initially considered a mild, transient disorder with limited long-term consequences, recent data, mainly autopsy based, suggest more significant long-term consequences in mTBI [4].

Sports injuries account for 20% of concussions in children and adults (https://www.cdc.gov/traumaticbraininjury/pdf/bluebook.pdf). Children and teens are among those at greatest risk for concussion. A much larger number of children are engaged in athletic activities than adults [5]. Indeed, one report found that 20.5% of 13-19 year old high-school athletes reported having more than one concussions [6]. In addition, most athletic activities among children are supervised by non-professional volunteers in contrast to college and professional level sports. Lack of medical knowledge significantly limits the ability of such supervising non-professionals to identify concussions when they occur in children, thus magnifying the risk of single impact and recurrent concussion injuries. Not surprisingly, the children themselves may not recognize the injury or its potential significance and have less ability compared to adults, to reliably report when such injuries occur.

Most concussions occur without loss of consciousness. As loss of consciousness is no longer a requirement for diagnosis of concussion, the most conspicuous sign and symptom has been removed from the diagnostic requirements, thereby increasing the chances of failed recognition in children. Together these findings significantly elevate the likely frequency of pediatric concussion.

Pediatric concussion presents a unique challenge and the health consequences may be even greater than concussion in older individuals. Published evidence suggests that when controlled for age, neurocognitive performance in concussed children <7 years old was worse than in older children [7]. Many explanations have been offered to try to understand the increased vulnerability of children to concussive blows. These include immaturity of the pediatric brain, relatively larger head size, thinner and thus less protective cranial bones and larger subarachnoid space which allows greater mobility of the brain on impact [5]. Incomplete myelination may put the pediatric brain at greater risk for shear injury [8].

Children with mTBI have more extensive cerebral edema and more metabolic perturbations than compared to adults [9]. Finally, children may be at increased risk for severe complications of recurrent concussion [10] and younger children <10 years old are more likely to display adverse behavioral outcomes compared to older children [11].

Given the unique vulnerabilities of children summarized above, biomarkers would be particularly beneficial in this population for accurate assessment and diagnosis, and appropriate management of concussion [12]. Despite an exponential increase in the number of concussion biomarkers that are being evaluated, there is currently no specific and sensitive biomarker for concussion that is available for clinical use at the bedside.

SUMMARY

Measuring methylation levels of cytosine ('CpG') loci throughout the genome, a total of 412 CpG sites, each associated with a separate gene, in which there was significant methylation changes associated with concussion compared to unaffected controls, in leucocyte DNA were found. There were a total of 119 methylation markers with good individual diagnostic accuracy (AUC≥0.80-0.89) and four with excellent individual diagnostic accuracy (AUC≥0.90-1.00) for the detection of concussion. The percentage difference in CpG methylation between pediatric concussion and controls was >10% in many of the methylation sites suggesting biological significance i.e. methylation level changes are significant enough to affect gene transcription. Pathway analysis using the differentially methylated genes identified several biologically important neuronal and brain pathways that were perturbed including those associated with: impaired brain function, memory, neurotransmission, intellectual disability, cognitive impairment, behavioral change and associated disorders including Alzheimer's disease, severe epileptic encephalopathy. Targeted metabolomic analysis (Nuclear Magnetic resonance-"NMR" and Liquid chromatography-Mass Spectrometry-Mass Spectrometry (LC-MS-MS)) was also performed on serum of the cases and controls undergoing epigenomic evaluation. Using Deep Learning (DL)/artificial intelligence (AI) and other machine learning (ML) AI (and also conventional logistic regression approaches), the combination of epigenomic, clinical and metabolomic markers was found to be highly accurate for the detection of concussion including mTBI. Children and adolescents are at high risk for concussion and therefore were used in this study. The findings significance herein and applications are in no way limited to children and adolescents however.

DETAILED DESCRIPTION

Figure 1A:
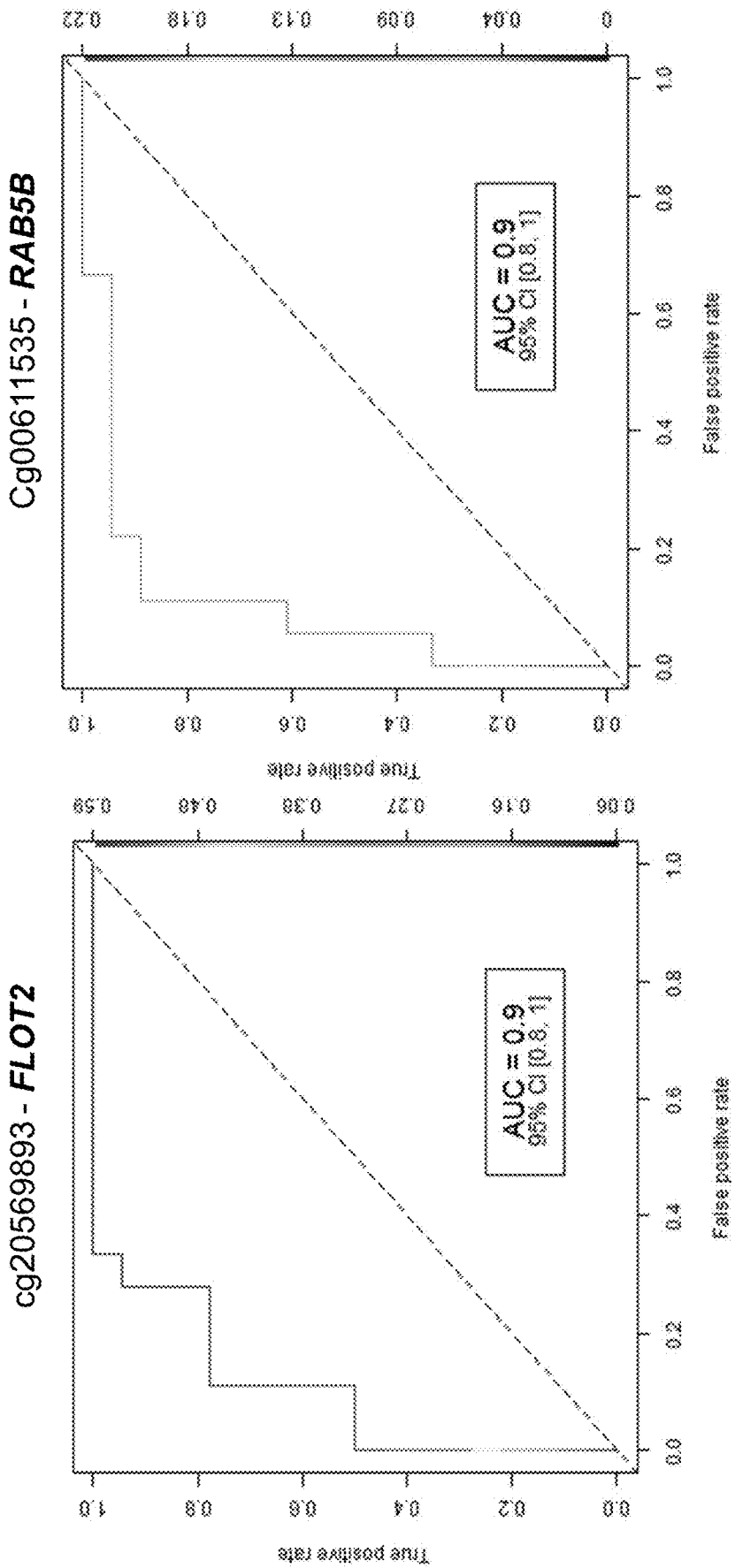
FIGS. 1A and 1B. Display Receiver operating characteristic (ROC) curve (graphic demonstration of predictive accuracy) of four specific CpG loci for the prediction of Pediatric concussion. A total of 449 CpG sites in 412 differentially-methylated genes that have an area under the ROC curve 0.75 were identified. An AUC 0.75 suggests that a marker could potentially have clinical utility. At each of these differentially methylated cytosine (CpG) loci, the False Detection Rate (FDR) p-value for the methylation difference between pediatric concussion cases and controls was <0.0001 and thus highly statistically significant. The most important individual CpG locus (and associated genes) based on level of methylation change in mTBI compared to unaffected controls included markers cg06393885 (chr 5, GALNT10), cg20569893 (chr 17, FLOT2), cg00611535 (chr 12, RAB5B), and cg16882751 (chr 1, FCMR) (where the chromosome; CpG locus-associated gene symbol provided). AUC: Area Under the Receiver Operating Characteristics Curve; 95% CI: 95% Confidence Interval. Lower and upper Confidence Intervals are given in parentheses.

Concussion, also known as minor head trauma or mild traumatic brain injury (mTBI) is the most common type of traumatic brain injury. Guidelines now recommend the use of the term mild traumatic brain injury. Several organizations including the World Health Organization (WHO) US Centers for Disease Control and Prevention (CDC) define mTBI as "an acute brain injury resulting from mechanical energy to the head from external physical forces." One or more of the following findings are required to make the diagnosis: 1. confusion, disorientation, loss of consciousness for 30 minutes or less, post traumatic amnesia for less than 24 hours and/or other transient neurologic abnormalities such as focal signs, symptoms or seizure. 2. Glasgow Coma Scale score of 13-15 after 30 minutes post-injury or later upon presentation for healthcare (Carroll L J, Cassidy J D, Holm L, et al. WHO Collaborating Center Task Force on Mild Traumatic Brain Injury. Methodological Issues and research recommendations for mild traumatic brain injury. J Rehab Med 2004; 43(suppl.):113-25.) Most concussions are unrecognized or do not present for medical attention. While most concussion resolve within six weeks, post-concussion syndrome can include physical, cognitive, and emotional problems. There is currently intense scientific interest in understanding the biological mechanisms of and in the development of biomarkers for the detection and monitoring of this common disorder. The pediatric period is one of heightened risk both in terms of frequency and also the susceptibility of the developing brain to perceived minor trauma.

Individuals at high risk for concussion extend across the general population. The highest rates are in young children (0-4 years), who are unable to provide any significant history. Older adolescents (age 15-19 years) and the elderly have high rates of TBI and concussion also. From the point of view of ethnicity, African Americans have the highest rates of TBI followed by whites. There is also a strong correlation between TBI and with alcohol use and abuse, which puts college students at elevated risk. Further, the relationship between TBI and alcohol use is heavily correlated with the occurrence of motor vehicle accidents. Falls are the most common cause of TBI, and this partly accounts for the high rates of TBI in young children and elderly individuals. Sports and recreational activities are a major cause of mTBI. The impact on children and adolescents is enormous. Approximately 30-45 million children and adolescents in the USA are believed to participate in organized sport each year. Approximately 7.6 million adolescents are engaged in high school sports. The risk of concussion is highest in contact sports. With 1.1 million high school students involved in American football there is a high level of risk for high school athletes in general and in particular in those playing football. These numbers are significantly larger than the number of college and professional athletes! Approximately 36% of college athletes report concussion, while 25% of high school athletes report concussion with 20% reporting recurrent concussions. According to the CDC there are up to 3.8 million sports related concussions per year in the USA. The American College of Sports Medicine estimates that 85% of sports related concussions are under-diagnosed.

Individuals in the military are at high risk of combat related TBI. The Department of Defense reported a total of approximately 300,000 TBI between 2000-2013 of these 80% were reported to be concussions.

A high percentage of the USA population is at risk for concussion and as noted the estimates of concussion frequency are likely to be gross underestimates, this is in large part due to the fact that objective tests or biomarkers do not currently exist. Currently the diagnosis of concussion is based on neuropsychological tests, such as Glasgow Coma Scale Score. Findings may be lacking on physical exam. Neuroimaging techniques such as CT and MRI are also used however the CT has low sensitivity for the milder forms of brain injury and MRI is too expensive for routine assessment. Relatively newer imaging techniques such as functional MRI, diffusion tensor imaging (DTI) and magnetic resonance spectroscopy and PET scanning are currently being evaluated. The cost and lack of uniform expertise with these technologies across hospitals remain a concern however.

During the early post traumatic period symptoms such as decline of cognition (difficulty concentrating, distractedness, forgetfulness), headaches, dizziness, fatigue, and depression can develop. In a percentage of cases, these symptoms can persist for many months. However, longer term consequences such as post traumatic sleep disorder develops in a significant minority of cases (~14%). Recurrent concussive episodes are now thought to increase the risk of severe long-term brain disorders such as chronic traumatic encephalopathy (CTE). The pediatric population is at higher risk for symptoms and complications from concussion. This is thought to be due to the immaturity of the brain, relatively larger head size and therefore a bigger target for injury and the softer skull, thus providing less protection against outside forces. A recent publication documented that among college and professional football players, those who started playing before age 12 years were at higher risk of developing subsequent Chronic Traumatic encephalopathy (CTE) emphasizing the unique susceptibility to trauma of children's the brain. Finally, the CDC estimated in a report to congress in 2003 that the annual cost of mild TBI in the US is approximately $16.7 billion.

Importance of Concussion/TBI Biomarkers.

The FDA and similar international organizations have prioritized the development of biomarkers for TBI and concussion. Biomarker development is an important part of the Critical Pathway Initiative of the FDA.

The main function of the ideal concussion biomarker would be for the detection of this under-diagnosed disorder. Additional desirable benefits could include the ability to measure concussion severity, monitor disease progression, long term prognosis and brain response to therapy. Future biomarkers could add very significant value by indicating the particular anatomical area(s) of the brain that have been injured.

Existing Concussion/TBI Biomarkers.

Some of the best studied biomarkers currently include s100β, Glial Fibrillary Acidic Protein (GFAP), Neuronal specific enolase (NSE), Tau Protein and others. A more extensive list can be obtained at (CNS Trauma Biomarkers and surrogate endpoints pipeline from Bench to bedside. In Kobeissy F N, editors, Brain Neurotrauma: Molecular, Neuropsychological, and Rehabilitation Aspects. Boca Raton (Fla.). CRC Press/Taylor and Francis 2015).

A further important benefit of biomarkers is to elucidate the mechanisms of ongoing brain damage after the initial trauma (e.g. oxidative stress, inflammation, biochemical abnormalities etc.) and thus generate the scientific basis for the development of novel pharmaceuticals and other treatment agents. Despite the significant potential benefits of biomarkers these have not been realized. The current recommendation is that outside of a research setting, biomarkers should not be used for the evaluation of mTBI in children (Lumba-Brown A et al. Centers for Disease Control and Prevention guideline on the Diagnosis and Management of mild traumatic brain injury among children, JAMA Pediatr doi:10.1001/jamapediatrics 2018.2853).

While genetic factors are generally not causative for the initial trauma, there is still the potential that genetic factors could have a significant role in the subsequent inflammatory response that contributes so significantly to ongoing brain damage following the initial trauma. Polymorphisms of many genes have been linked to outcomes in TBI. This have been comprehensively reviewed elsewhere. [13] Such genes include but are not limited to TNF-α, IL-1, IL-6 and APOE 4. However, these findings have not been uniformly confirmed, and there is even less genetic data available on TBI in children. The APOE 4 allele has been linked to poor global outcomes in concussion in children [14]. A genome-wide association study (GWAS) study yielded four qualified articles which cumulatively confirmed an association between the APOE gene allele and neurologic outcomes in TBI in children [15].

There is paucity of data about the epigenetics of concussion. Animal experimental data reveals an influence of epigenetic changes, including histone modification and DNA hypomethylation, in the brain's response to TBI [16, 17]. Decreases in plasma methionine levels have been reported after mTBI in humans [18]. Methionine, is an essential amino acid, serves as a substrate for s-adenosyl methionine (SAM). SAM is the major methyl donor for methylation reactions including DNA methylation, a key epigenetic mechanism. A decrease in SAM production was observed in mild traumatic brain injury (mTBI), as well as decreases in serum choline and betaine concentrations. Both choline and betaine are also methyl donors involved in DNA methylation pathways.

The monumental challenge in studying TBI is the inaccessibility of the brain for direct study in clinical subjects. A study by Petrone et al. [19] found that an early response to mTBI in (non-pediatric) human subjects was a change in peripheral blood neutrophil and lymphocyte counts. More interestingly, they demonstrated significant changes in the expression level of many immune-related genes in the blood of mTBI patients, including MMP9, LY96, CCR, 7ARG1, and S100a12. Good diagnostic accuracy for mTBI detection were reported using blood mRNA expression levels of these genes. The purpose of this study and application is to identify blood-based biomarkers for accurate detection of mTBI in patients including adults and pediatric patients, as no such markers are available to date.

Metabolomics refers to the quantitation and identification of the small molecules which are the substrates and by-products of cellular biochemical reactions. Global assessment of endogenous and exogenous metabolites from the cells, tissues or biofluids is performed (Wishart O S. Chapter 3: Small molecules and disease. PLoS Comput Biol. 2012; 8(12: e1002805). Metabolomics is down-stream of genomics, proteomics and transcriptomics and most closely correlates with disease phenotype. It involves the comprehensive, simultaneous and systematic profiling of metabolite concentrations, which is sensitive to disease phenotype. It holds significant promise both for the generation of biomarkers for disease detection and for elucidating the pathogenesis of disease. Limited data currently exists on the use of metabolomics in traumatic brain injury but animal data suggest that metabolomic markers may have significant diagnostic accuracy for traumatic brain injury (Bahado-Singh et al., (2016) Serum Metabolomic Markers for Traumatic Brain Injury: A Mouse Model. Metabolomics 12:100. https://doi.or/10.1007/s11306-016-1044-3: Bahado-Singh et al., (2016) Identification of candidate biomarkers of brain damage in a mouse model of closed head injury: a metabolomic pilot study. Metabolomics. 12:42. https://doi.org/10.1007/s11306-016-0957-1).

A recent metabolomics study (REF: Daley_M. Qekaban, G., Bartha, R. et al. Metabolomics (2016) 12:185. https://doi.org/10.10071s11306-0 16-1131-5) including adolescent athletes was able to achieve the 92% diagnostic accuracy in the detection of concussion. To this date this is the only metabolomics study that was performed in the identification of pediatric concussion biomarkers. This data however was generated from children at the border of adulthood and strictly related to trauma resulting from athletic pursuits which is likely to be more severe than brain trauma sustained from other head trauma sustained during the course of routine childhood activities.

Artificial Intelligence (AI) represents a discipline in computer sciences which focuses on the development of systems for the performance of intellectual tasks that are normally requires human cognition (Chartrand G, Cheng P M, Vorontsov E, et al. deep Learning: A primer for Radiologists RadioGraphics 2017; 37:2113-31). Machine Learning (ML) is a branch of AI in which computers are trained to perform tasks based on the computers experiential learning rather than by explicit programming by humans. Deep Learning is the latest and a rapidly developing branch of AI. Deep Learning is a class of machine learning in which the number of layers of neural networks is significantly expanded i.e. greater 'neuronal' complexity and thus expanding computational power. It has been shown to further improve performance in important current applications such as image and speech recognition. It appears to have a greater capacity to handle and interpret the torrent of data being generated by systems biology analysis. and preliminary data would suggest that it is ideally suited for the complexities of epigenomic and metabolomic data analysis. Other examples of AI algorithms include Random Forest (RF), Support Vector Machine (SVM), Linear Discriminant Analysis (LDA), Prediction of Analysis for Microarrays (PAM), and Generalized Linear Model (GLM).

The term "epigenetics" can be used to describe the interaction between genes and the environment. These interactions do not result in changes to the genome itself (no nucleotide sequence changes) but still account for variations in phenotypic expression. Epigenetic modifications are a major mechanism by which injury and destructive prenatal environmental factors can lead to long-term disturbances of brain development, such as cognitive, motor, or behavioral impairments. During the acute and secondary phases of brain injury there is substantial loss of acetylation and methylation tags and considerable variation in microRNA expression. MicroRNA are short non-coding RNAs that control gene expression and are also known to exert significant influence on DNA methylation. Reduced acetylation, another epigenetic mechanism, is associated with cognitive decline, which is accelerated after brain injury. Changes to epigenetic processes might be particularly relevant for white matter injury. Epigenetic dysregulation occurs with important risk factors (for example, age, alcohol usage, etc.) for TBI including mTBI.

Epigenetics is defined as heritable (i.e. passed onto offspring) changes in gene expression of cells that are not primarily due to mutations or changes in the sequence of nucleotides (adenine, thiamine, guanine, and cytosine) in the genes. Epigenetics is a reversible regulation of gene expression by several potential mechanisms. One such mechanism which is the most extensively studied is DNA methylation. Other mechanisms include changes in the 3-dimensional structure of the DNA, histone protein modification, and micro-RNA inhibitory activity. The epigenetic mechanisms are known to be extensively inter-related.

The present disclosure describes the use of epigenomic and metabolomic markers and Artificial Intelligence analytic techniques for accurate detection of pediatric concussion.

Epigenomic Analysis.

Using the Illumina HumanMethylation450 BeadChip assay, methylation levels of CpG sites across the genome were examined in 18 pediatric concussion cases and compared to 18 of unaffected healthy matched controls. Pathway analysis was performed using Ingenuity pathway analysis to elucidate the mechanism of the disorder. In addition, the diagnostic accuracy of epigenomic markers for the detection of concussion was determined. Area under the receiver operating characteristics (AUC) curves and 95% CI and FDR p-values were calculated for the detection of concussion.

Metabolomic Analysis.

In addition to epigenomic analysis, $^1$H-NMR (proton based Nuclear magnetic resonance) spectroscopy and Liquid chromatography-Mass spectrometry-Mass spectrometry (LC-MS-MS)—based metabolomic analysis was performed on the serum of the study patients. Clinical and demographic data were obtained for each patient. We report on a subgroup of cases and controls that had both epigenomic and metabolomic analysis to demonstrate the value of combined omics for the detection of concussion.

Several different Artificial Intelligence (AI) techniques including Deep Learning (DL), the newest form of AI, were used to predict concussion using i) epigenetic i.e. DNA methylation markers ii) metabolomic iii) clinical and demographic markers and finally iv) different combination of omics, clinical and demographic markers.

The present disclosure describes the identification of 412 discrete CpG loci, each associated with a distinct gene, in which there was statistically significant methylation changes associated with concussion. There was a total of 119 methylation markers with good individual diagnostic accuracy (AUC≥0.80-0.89) and four with excellent individual diagnostic accuracy (AUC≥0.90-1.00) for the detection of concussion. The CpG methylation differences between pediatric concussion and controls was 210% in many of the methylation sites suggesting biological significance i.e. an effect on gene expression. Ingenuity molecular Pathway analysis based on the affected genes identified several biologically important neurological (gene) pathways that were perturbed including those associated with: impaired brain function, memory, neurotransmission, intellectual disability, cognitive impairment, behavioral change and associated disorders including Alzheimer's disease, severe epileptic encephalopathy. Epigenomic markers by themselves were highly accurate for the detection of concussion. When these were combined with clinical predictors the accuracy was only minimally higher (but not statistically significantly so) than the use of epigenomic markers alone. Combinations of epigenomic, clinical and metabolomic markers were evaluated in differently performing subsets of epigenomic markers. The metabolomic markers include metabolites or small molecules. The addition of metabolomic to epigenetic markers slightly lowered predictive accuracy from epigenomic markers by themselves. Using all three groups of markers (epigenomic, clinical plus metabolomic markers) did not improve accuracy over combined epigenetic plus clinical markers combined, but slightly improved performance over epigenetic markers alone.

The present disclosure confirms highly significant differences in the percentage methylation of cytosine nucleotides in leucocyte DNA throughout the genome in individuals with mTBI versus normal groups using a widely available commercial bisulfite-based assay for distinguishing methylated from unmethylated cytosine. Cytosine loci analyzed were not limited to CpG islands or to specific genes but included cytosine loci outside of CpG islands and outside of genes. For the purposes of this particular disclosure, cytosine loci associated with known genes were reported. Significant differences in cytosine methylation loci throughout the genome were observed between TBI patients and unaffected controls. The combination of cytosine loci can be used to accurately predict TBI and particularly mTBI or concussion which is the most common form of TBI and which frequently fails to be diagnosed.

Particular aspects provide panels of known and identifiable cytosine loci throughout the genome whose methylation levels (expressed as percentages) is useful for distinguishing TBI from normal cases.

Additional aspects describe the capability of combining other recognized TBI clinical tests and novel metabolomics markers combined with cytosine methylation for the diagnosis of TBI. Multiple individual cytosine (CpG) loci demonstrate highly significant differences in the degree of their methylation in TBI versus normal cases (FDR q-values <0.05 to $1.0\times10^{32}$).

TBI is classified based on the severity of the injury, the pathological features of the injury, and the mechanism (causative forces) of the injury. Severity of TBI could be mild, moderate and severe depending on the extent of damage to the brain, patients level of consciousness and reactions to stimuli. Pathological features can include lesions within the skull and outside of the brain or within the brain tissue. The injury can also be focal, confined to a specific area, or diffuse, distributed to a general area. Causes of the TBI can include falls, violence, transportation accidents, and sports.

Cytosine refers to one of a group of four building blocks "nucleotides" from which DNA is constructed. The chemical structure of cytosine is in the form of a pyrimidine ring. Apart from cytosine, the other nucleotides or building blocks found in DNA are thiamine, adenine, and guanosine.

The term methylation refers to the enzymatic addition of a "methyl group" or single carbon atom to position #5 of the pyrimidine ring of cytosine which leads to the conversion of cytosine to 5-methyl-cytosine. The methylation of cytosine as described is accomplished by the actions of a family of enzymes named DNA methyltransferases (DNMTs). The 5-methyl-cytosine when formed is prone to mutation or the chemical transformation of the original cytosine to form thymine. Five-methyl-cytosines account for about 1% of the nucleotide bases overall in the normal genome.

The term hypermethylation refers to increased frequency or percentage methylation at a particular cytosine locus when specimens from an individual or group of interest is compared to a normal or control group.

Cytosine is usually paired with guanosine another nucleotide in a linear sequence along the single DNA strand to form CpG pairs. "CpG" refers to a cytosine-phosphate-guanosine chemical bond in which phosphate binds the two nucleotides together. In mammals, in approximately 70-80% of these CpG pairs the cytosine is methylated (Chatterjee R, Vinson C. Biochemica et Biophisica Acta 2012; 1819:763-70). The term "CpG island" refers to regions in the genome with high concentration of CG dinucleotide pairs or CpG sites. "CpG islands" are often found close to genes in mammalian DNA. The length of DNA occupied by the CpG island is usually 300-3000 base pairs. The CG cluster is on the same single strand of DNA. The CpG island is defined by various criteria including i) the length of recurrent CG dinucleotide pairs occupying at least 200 bp of DNA and ii) a CG content of the segment of at least 50% along with the fact that the observed/expected CpG ratio should be greater than 60%. In humans about 70% of the promoter regions of genes have high CG content. The CG dinucleotide pairs may exist elsewhere in the gene or outside of a gene and not know to be associated with a particular gene.

Approximately 40% of the promoter region (region of the gene which controls its transcription or activation) of mammalian genes have associated CpG islands and three quarters of these promoter-regions have high CpG concentrations. Overall in most CpG sites scattered throughout the DNA the cytosine nucleotide is methylated. In contrast in the, CpG sites located in the CpG islands of promoter regions of genes, the cytosine is unmethylated suggesting a role of methylation status of cytosine in CpG Islands in gene transcriptional activity.

The methylation of cytosines associated with or located in a gene is classically associated with suppression of gene transcription. In some genes however, increased methylation has the opposite effect and results in activation or increased transcription of a gene. One potential mechanism explaining the latter phenomenon is that methylation of cytosine could potentially inhibit the binding of gene suppressor elements thus releasing the gene from inhibition. Epigenetic modification, including DNA methylation, is the mechanism by which for example cells which contain identical DNA and genes experience activation of different genes and result in the differentiation into unique tissues e.g. heart or intestines.

The receiver operating characteristics (ROC) curve is a graph plotting sensitivity—defined in this setting as the percentage of TBI cases with a positive test or abnormal cytosine methylation levels at a particular cytosine locus on the Y axis and false positive rate (1—specificity or 100% —specificity when the latter is expressed as a percentage)—i.e. the number of normal non-TBI cases with abnormal cytosine methylation at the same locus—on the X-axis. Specificity is defined as the percentage of normal cases with normal methylation levels at the locus of interest or a negative test. False positive rate refers to the percentage of normal individuals falsely found to have a positive test (i.e. abnormal methylation levels); it can be calculated as 100-specificity (%) or expressed as a decimal format [1-specificity (expressed as a decimal point)].

The area under the ROC curves (AUC) indicates the accuracy of the test in identifying normal from abnormal cases[37].

The AUC is the area under the ROC plot from the curve to the diagonal line from the point of intersection of the X- and Y-axes and with an angle of incline of 45°. The higher the area under receiver operating characteristics (ROC) curve the greater is the accuracy of the test in predicting the condition of interest. An area under the ROC=1.0 indicates a perfect test, which is positive (abnormal) in all cases with the disorder and negative in all normal cases (without the disorder). Methylation assay refers to an assay, a large number of which are commercially available, for determining the level of methylation at a particular cytosine in the genome. In this particular context, we are using this approach to distinguish the level of methylation in affected cases (mTBI) compared to unaffected controls.

Methylation Assays.

Several quantitative methylation assays are available. These include COBRA™ which uses methylation sensitive restriction endonuclease, gel electrophoresis and detection based on labeled hybridization probes. Another available technique is the Methylation Specific PCR (MSP) for amplification of DNA segments of interest. This is performed after sodium 'bisulfite' conversion of cytosine using methylation sensitive probes. MethyLight™, a quantitative methylation assay-based uses fluorescence based PCR. Another method used is the Quantitative Methylation (QM™) assay, which combines PCR amplification with fluorescent probes designed to bind to putative methylation sites. Ms-SNuPE™ is a quantitative technique for determining differences in methylation levels in CpG sites. As with other techniques bisulfite treatment is first performed leading to the conversion of unmethylated cytosine to uracil while methyl cytosine is unaffected. PCR primers specific for bisulfite converted DNA is used to amplify the target sequence of interest. The amplified PCR product is isolated and used to quantitate the methylation status of the CpG site of interest. The preferred method of measurement of cytosine methylation is the Illumina method.

Illumina Method.

For DNA methylation assay the Illumina Infinium® Human Methylation 450 Beadchip assay was used for genome wide quantitative methylation profiling. Briefly genomic DNA is extracted from cells in this case archived blood spot, for which the original source of the DNA is white blood cells. Using techniques widely known in the trade, the genomic DNA is isolated using commercial kits. Proteins and other contaminants were removed from the DNA using proteinase K. The DNA is removed from the solution using available methods such as organic extraction, salting out or binding the DNA to a solid phase support.

Bisulfite Conversion.

As described in the Infiniumrr Assay Methylation Protocol Guide, DNA is treated with sodium bisulfite which converts unmethylated cytosine to uracil, while the methylated cytosine remains unchanged. The bisulfite converted DNA is then denatured and neutralized. The denatured DNA is then amplified. The whole genome application process increases the amount of DNA by up to several thousand-fold. The next step uses enzymatic means to fragment the DNA. The fragmented DNA is next precipitated using isopropanol and separated by centrifugation. The separated DNA is next suspended in a hybridization buffer. The fragmented DNA is then hybridized to beads that have been covalently limited to 50mer nucleotide segments at a locus specific to the cytosine nucleotide of interest in the genome. There is a total of over 500,000 bead types specifically designed to anneal to the locus where the particular cytosine is located. The beads are bound to silicon-based arrays. There are two bead types designed for each locus, one bead type represents a probe that is designed to match to the methylated locus at which the cytosine nucleotide will remain unchanged. The other bead type corresponds to an initially unmethylated cytosine which after bisulfite treatment is converted to a thiamine nucleotide. Unhybridized (not annealed to the beads) DNA is washed away leaving only DNA segments bound to the appropriate bead and containing the cytosine of interest. The bead bound oligomer, after annealing to the corresponding patient DNA sequence, then undergoes single base extension with fluorescently labeled nucleotide using the 'overhang' beyond the cytosine of interest in the patient DNA sequence as the template for extension.

If the cytosine of interest is unmethylated then it will match perfectly with the unmethylated or "U" bead probe. This enables single base extensions with fluorescent labeled nucleotide probes and generate fluorescent signals for that bead probe that can be read in an automated fashion. If the cytosine is methylated, single base mismatch will occur with the "U" bead probe oligomer. No further nucleotide extension on the bead oligomer occurs however thus preventing incorporation of the fluorescent tagged nucleotides on the bead. This will lead to low fluorescent signal form the bead "U" bead. The reverse will happen on the "M" or methylated bead probe.

Laser is used to stimulate the fluorophore bound to the single base used for the sequence extension. The level of methylation at each cytosine locus is determined by the intensity of the fluorescence from the methylated compared to the unmethylated bead. Cytosine methylation level is expressed as "β" which is the ratio of the methylated bead probe signal to total signal intensity at that cytosine locus. These techniques for determining cytosine methylation have been previously described and are widely available for commercial use.

The present disclosure describes the use of a commercially available methylation technique to cover up to 99% Ref Seq genes involving approximately 16,000 genes and 450,000 cytosine nucleotides down to the single nucleotide level, throughout the genome (Infinium Human Methylation 450 Beach Chip Kit). The frequency of cytosine methylation at single nucleotides in a group of TBI cases compared to controls is used to estimate the risk or probability of being diagnosed with TBI. The cytosine nucleotides analyzed using this technique included cytosines within CpG islands and those at further distances outside of the CpG islands i.e. located in "CpG shores" and "CpG shelves" and even more distantly located from the island so called "CpG seas".

Identification of Specific Cytosine Nucleotides.

Reliable identification of specific cytosine loci distributed throughout the genome has been detailed (Illumnia) in the document: "CpG Loci Identification. A guide to Illumina's method for unambiguous CpG loci identification and tracking for the GoldenGate®) and Infinium™ assays for Methylation." A brief summary follows. Illumina has developed a unique CpG locus identifier that designates cytosine loci based on the actual or contextual sequence of nucleotides in which the cytosine is located. It uses a similar strategy as used by NCBI's re SNP IPS (rs#) and is based on the sequence flanking the cytosine of interest. Thus, a unique CpG locus cluster ID number is assigned to each of the cytosine undergoing evaluation. The system is reported to be consistent and will not be affected by changes in public databases and genome assemblies. Flanking sequences of 60 bases 5' and 3' to the CG locus (i.e. a total of 122 base sequences) is used to identify the locus. Thus, a unique "CpG cluster number" or cg# is assigned to the sequence of 122 bp which contains the CpG of interest. The cg# is based on Build 37 of the human genome (NCBI37). Accordingly, only if the 122 bp in the CpG duster is identical is there a risk of a locus being assigned the same number and being located in more than one position in the genome. Three separate criteria are utilized to track individual CpG locus based on this unique ID system. Chromosome number, genomic coordinate and genome build. The lesser of the two coordinates "C" or "G" in CpG is used in the unique CG loci identification. The CG locus is also designated in relation to the first 'unambiguous" pair of nucleotides containing either an 'A' (adenine) to 'T' (thiamine). If one of these nucleotides is 5' to the CG then the arrangement is designated TOP and if such a nucleotide is 3' it is designate BOT.

In addition, the forward or reverse DNA strand is indicated as being the location of the cytosine being evaluated. The assumption is made that methylation status of cytosine bases within the specific chromosome region is synchronized[41].

Description of the Method.

A total of 18 cases of TBI, along with a total of 18 controls underwent epigenetic analysis. Control cases were normal patients at the time of chart review and at patient reporting and with no known or suspected brain injury. TBI patients as a single group was compared to unaffected controls.

In embodiments, the present disclosure describes a method for diagnosing TBI based on measurement of frequency or percentage methylation of cytosine nucleotides in various identified loci in a DNA sample. In embodiment, the DNA sample can be obtained from a biological sample of a patient in need thereof. The method includes obtaining a biological sample from a patient; extracting DNA from the sample; assaying the sample to determine the percentage methylation of cytosine at loci throughout genome; comparing the cytosine methylation level of the patient to a control; and calculating the individual risk of being diagnosed with TBI based on the cytosine methylation level at different sites throughout the genome. In embodiments, the patients could be adults and the control could be a well characterized group of normal (healthy) people and/or well characterized population of TBI patients. In embodiments, the patient could be a pediatric patient. The pediatric patient can be less than about 19 years old, about 15 to 19 years old, less than about 15 years old, about 10 to 15 years old, less than 10 years old, about 5 to 10 years old, less about 4 years old, about 1 to 4 years old, or less than one year old. The control could be a well characterized group of normal (healthy) children of less than about 19 years old and/or well characterized population of TBI pediatric patients. The well characterized group of normal people or TBI patients may include one or more normal people or TBI patients or may include a population of normal people or TBI patients. The control group of normal people or TBI patients could be children of less than 19 years of age or adults of more than 19 years of age.

DNA Extraction from Blood-Spot.

DNA was obtained from blood draw or venipuncture. DNA extraction can similarly be obtained from a fingerstick leading to a blood spot on filter paper and performed as described in the EZ1® DNA Investigator Handbook, Sample and Assay Technologies, QIAGEN 4$^{th}$ Edition, April 2009. A brief summary of the DNA extraction method is provided. Two 6 mm diameter circles (or four 3 mm diameter circles) are punched out of a dried blood spot stored on filter paper and used for DNA extraction. The circle contains DNA from white blood cells from approximately 5 µL of whole blood. The circles are transferred to a 2 ml sample tube.

A total of 190 µL of diluted buffer G2 (G2 buffer distilled water in 1:1 ratio) are used to elute DNA from the filter paper. Additional buffer is added until residual sample volume in the tube is 190 1 L since filter paper will absorb a certain volume of the buffer. Ten µL of proteinase K is added and the mixture is vortexed for 10 s and quick spun. The mixture is then incubated at 56° C. for 15 minutes at 900 rpm. Further incubation at 95° C. for 5 minutes at 900 rpm is performed to increase the yield of DNA from the filter paper. Quick spin is then performed. The sample is then run on EZ1Advanced (Trace, Tip-Dance) protocol as described. The protocol is designed for isolation of total DNA from the mixture. Elution tubes containing purified DNA in 50 µL of water is now available for further analysis.

Infinium DNA Methylation Assay.

Methylation Analysis-Illumina's Infinium Human Methylation 450 Bead Chip system was used for genome-wide methylation analysis. DNA (500 ng) was subjected to bisulfite conversion to deaminate unmethylated cytosines to uracil with the EZ-96 Methylation Kit (Zymo Research) using the standard protocol for the Infinium assay. The DNA is enzymatically fragmented and hybridized to the Illumina BeadChips. BeadChips contain locus-specific oligomers and are in pairs, one specific for the methylated cytosine locus and the other for the unmethylated locus. A single base extension is performed to incorporate a biotin-labeled ddNTP. After fluorescent staining and washing, the BeadChip is scanned and the methylation status of each locus is determined using BeadStudio software (Illumina). Experimental quality was assessed using the Controls Dashboard that has sample-dependent and sample-independent controls target removal, staining, hybridization, extension, bisulfite conversion, specificity, negative control, and non-polymorphic control. The methylation status is the ratio of the methylated probe signal relative to the sum of methylated and unmethylated probes. The resulting ratio indicates whether a locus is unmethylated (0) or fully methylated. Differentially methylated sites are determined using the Illumina Custom Model and filtered according to p-value using 0.05 as a cutoff.

Illumina's Infinium HumanMethylation450 BeadChip system, an updated assay method that covers CpG sites (containing cytosine) in the promoter region of more genes, i.e., approximately 16,880 genes. In addition other cytosine loci throughout the genome and outside of genes, and within or outside of CpG islands are represented in this assay.

Cytosine Methylation for the Diagnosing TBI Using ROC Curve.

To determine the accuracy of the methylation level of a particular cytosine locus for TBI prediction, different threshold levels of methylation e.g. 10%, ≤20%, ≤30%, ≤40% etc. at the site was used to calculate sensitivity and specificity for TBI diagnosis. Thus, for example using ≤10% methylation at a particular cg locus, cases with methylation levels above this threshold would be considered to have a positive test and those with lower than this threshold are interpreted as a negative methylation test. The percentage of TBI cases with a positive test in this example 10% methylation at this particular cytosine locus would be equal to the sensitivity of the test. The percentage of normal non-TBI cases with cytosine methylation levels of <10% at this locus would be considered the specificity of the test. False positive rate is here defined as the number of normal cases with a (falsely) abnormal test result and sensitivity is defined as the number of TBI cases with (correctly) abnormal test result e.g. the level of methylation 10% at this particular cg location. A series of threshold methylation values are evaluated e.g. ≤1/10, ≤1/20, ≤1/30 etc., and used to generate a series of paired sensitivity and false positive values for each locus. A receiver operating characteristic (ROC) curve which is a plot of data points with sensitivity values on the Y-axis and false positivity rate on the X-axis is generated. This approach can be used to generate ROC curves for each individual cytosine locus that displays significant methylation differences between cases and TBI groups. In this instance the computer program ROCR package-version 3.4 ((https://CRAN.R-project.or/package=ROCR) was used to generate the area under the ROC curves.

Standard statistical testing using p-values to express the probability that the observed difference between cytosine methylation at a given locus between TBI and control DNA specimens were performed.

More stringent testing of statistical significance using False Discovery Rate (FDR) for multiple comparison was also performed. The FDR gives the probability that positive results were due to chance when multiple hypothesis testing is performed using multiple comparisons.

In embodiments, using the Illumina Infinium Assays for whole genome methylation studies, significant differences in the frequency (level or percentage) of methylation of specific cytosine nucleotides associated with particular genes were demonstrated in the TBI group when compared to a normal group. The differences in cytosine methylation levels are highly significant and of sufficient magnitude to accurately distinguish the TBI from the normal group. Thus, the methods described herein can be used as a test to screen for TBI cases among a mixed population with TBI and normal cases.

The degree of methylation of cytosines could potentially vary based on individual factors (diet, race, age, gender, medications, toxins, environmental exposures, other concurrent medical disorders and so on). Overall, despite these potential sources of variability, whole genome cytosine methylation studies identified specific sites within (and outside of) certain genes and could distinguish and therefore could serve as a useful blood screening test for identification of groups of individuals predisposed to or at increased risk for being diagnosed with TBI compared to normal cases.

Since cells, with few exceptions (mature red blood cells and mature platelets), contain nuclei and therefore DNA, the methods described herein can be used to screen for TBI using DNA from any cells with the exception of the two named above. In addition, cell free DNA from cells that have been destroyed and which can be retrieved from body fluids can be used for such screening. Such cell-free DNA is known to be disseminated from the brain into the bloodstream after head trauma. Specific techniques for identifying the tissue of origin of the cell-free DNA e.g. brain are now in existence and can be used to focus the analysis of circulating cell-free DNA methylation to particular organs of interest (Moss J, Magenheim J, Neiman D, et al). Comprehensive human cell-type methylation atlas reveals origins of circulating cell-free DNA in health and disease. Nature Communication 2018; 9: 1-19)

Cells and nucleic acids from any biological samples which contain nucleic acids can be used for the purpose of assessing or predicting TBI in a patient. Samples used for testing can be obtained from living or dead tissue and also archeological specimens containing cells or tissues. Nucleic acids include DNA or RNA, including for example, mRNA. Examples of biological samples that can be used for TBI screening include: any sample containing cell-free nucleic acids including cell-free DNA or RNA, skin, hair, follicles/roots, mucous membranes, internal body tissue. Examples of mucous membranes include cheek scrapings, buccal scrapings, or scrapings from the tongue for epigenomic analysis. For metabolomic analysis body fluids as well as tissue/cells can be used for analysis. Examples of body fluids include blood, saliva, urine, sweat, breath condensate and tears.

Biological samples can be obtained from patients (living or dead), including an adult, or a pediatric patient. The biological sample can be a body fluid, such as blood, urine or saliva. The biological sample can be tissue samples. As an example, cells and nucleic acids including DNA and RNA can be obtained from the biological sample for testing for TBI.

Embodiments include the use of genome-wide differences in cytosine methylation in DNA to screen for and determine risk or likelihood of TBI at any stage of life. These stages include the neonatal period (first 28 days after birth), infancy (up to 1 year of age), childhood (up to 10 years of age, adolescence (11 to 19 years of age), and adulthood (i.e. >19 years of age).

The results presented herein confirm that based on the differences in the level of methylation of the cytosine sites between TBI and normal cases throughout the whole human genome, the predisposition to or risk of having a TBI overall or subcategories of TBI can be determined.

Genome wide cytosine methylation study provides information on the orchestrated widespread activation and suppression of multiple genes and gene networks involved in brain injury after trauma. The approach does not require prior knowledge of the role of particular genes in brain injury in TBI. Further, hundreds of thousands of cytosine loci involving thousands of genes are evaluated simultaneously and in an unbiased fashion and can thus be used to accurately estimate the risk of TBI. Of further importance is the fact that cytosine loci outside of the genes can also control gene function. While we have mainly focused on CpG loci within and known/believed to be associated with particular genes it should be noted that methylation levels of loci situated outside of the gene can impact gene function and further contribute to the prediction of TBI.

In embodiments, the present disclosure confirms aberration or change in the methylation pattern of cytosine nucleotide occurs at multiple cytosine loci throughout the genome in individuals affected with different forms of TBI compared to individuals with normal brain development.

In embodiments, the present disclosure describes techniques and methods for predicting or estimating the risk of being diagnosed with TBI based on the differences in cytosine methylation at various DNA locations throughout the genome.

Currently no reliable clinically available biological method using cells, tissue or body fluids exist for predicting or estimating the risk of being diagnosed with TBI in individuals in the population.

TBI overall was evaluated and compared normal groups and cytosine nucleotides displaying statistically significant differences in methylation status throughout the genome were identified. Because of the extended coverage of cytosine nucleotides, some differentially methylated cytosines were located outside of CpG islands and outside of known genes. Nucleic acid cytosine methylation changes in either intragenic or extragenic cytosines individually (or in any combinations) can be used to detect or diagnose TBI.

The frequency or percentage of methylation of cytosine at one or more loci is compared with one or more controls. The controls include the frequency or percentage of methylation of cytosine of a well characterized population of normal (healthy) subjects or of a well characterized population of subjects known to have TBI. The TBI can be a specific form of TBI.

The present study reports a strong association between cytosine methylation status at a large number of cytosine sites throughout the genome using stringent False Discover Rate (FDR) analysis with q-values <0.05 and with many q-values as low as $<1 \times 10^{-3}$ depending on particular cytosine locus being considered (Table 2). A total of 18 cases of TBI and 18 normal controls underwent epigenomic analysis. Significant differences in cytosine methylation patterns at multiple loci throughout the DNA that was found in all TBI cases tested compared to normal. The particular cytosines disclosed in this application are located in or related with known genes. The findings are consistent with altered expression of multiple genes in TBI cases compared to controls.

The cytosine methylation markers reported enables targeted screening studies for the prediction and detection of TBI based on cytosine methylation throughout the genome. They also permit improved understanding of the mechanism of development of TBI for example by evaluating the cytosine methylation data using gene ontology analysis.

The cytosine evaluated in the present application includes but are not limited to cytosines in CpG islands located in the promoter regions of the genes. Other areas targeted and measured include the so called CpG island 'shores' located up to 2000 base pairs distant from CpG islands and 'shelves' which is the designation for DNA regions flanking shores. Even more distant areas from the CpG islands so called "seas" were analyzed for cytosine methylation differences. The extragenic cytosine loci, located outside of known genes (however they could potentially maintain long-distance control of unspecified genes) also detected TBI with moderate, good and excellent accuracy as indicated based on the AUROC. Thus, comprehensive and genome-wide analysis of cytosine methylation is performed.

Cell-Free DNA.

Cell free DNA (cfDNA) refers to DNA that has been released from cells as a result of natural cell death/turnover or as a result of disease processes. The cell free DNA is released into the circulation and rapidly broken down to DNA fragment. The techniques for harvesting of cell free DNA from the blood and other body fluids is well known in the arts (Li Y et al. Size separation of circulatory DNA in maternal plasma permits ready detection of fetal DNA polymorphisms. Clin Chem 2004; 50:1002-1011; Zimmerman B et al. Noninvasive prenatal aneuploidy testing of chromosomes 13, 18, 21, X, and Y, using targeted sequencing of polymorphic loci. Prenat Diagn 2012; 32:1233-41). In traumatic brain injury (TBI), damage to the blood brain barrier leads to increased circulating cfDNA in the blood and in severe TBI has been shown to correlate with prognosis (Macher H, Egea-Guerrero J J, Revuelto-Rey J et al. Role of early cell-free DNA levels decrease as a predictive marker of fatal outcome after severe traumatic brain injury. Clin Chim Acta 2012; 414:12-17). Epigenetic analysis of circulating cfDNA (from the brain after trauma) therefore represents a unique opportunity to evaluate brain function non-invasively (i.e. by analysis of the blood). Techniques for precision targeting of circulating cell free DNA from the brain will further enhance understanding of mechanism and the detection of TBI. Analyses of cell free DNA from different tissues e.g. the cortical neurons are now in existence (Moss J et al. Comprehensive human cell-type methylation atlas reveals origins of circulating cell-free DNA in health and disease. Nature communication 2018; 9: 1-19). Targeting of brain cell free DNA and epigenomic analysis will further enhance understanding of mechanism and detection of TBI.

Statistical Analyses.

The present disclosure describes a method for estimating the individual risk of being diagnosed with TBI or even a particular type of TBI. This calculation can be based on logistic regression analysis leading to identification of the significant independent predictors among a number of possible predictors (e.g. methylation loci) known to be associated with increased risk of being diagnosed with TBI. Cytosine methylation levels at different loci can be used by themselves or in combination with other known risk predictors such as for example such as clinical test e.g. Standardized Assessment of Concussion (SAC) score. This is a clinical assessment test of functions that are likely to be affected by trauma including orientation, memory, neurological functions (e.g. sensation, concentration etc), delayed recall of words and ability to withstand exertion. In addition, clinical findings such as loss of consciousness (important but not a required diagnostic feature of concussion) can be combined with methylation changes for the prediction of concussion. The probability of an individual being affected with concussion can be determined based on the logistic equation:

$$P_{TBI} = 1/1 + e - (\beta 1 x_1 + \beta 2 x_2 + \beta 3 x_3 \ldots \beta n x_n)$$

where 'x' refers to the magnitude or quantity of the particular predictor (e.g. methylation level at a particular locus) and "β" or β-coefficient herein refers to the magnitude of change in the probability of the outcome (a particular type of TBI) for each unit change in the level of the particular predictor (x), the β values are derived from the results of the logistic regression analysis. These β-values would be derived from multivariable logistic regression analysis in a large population of affected and unaffected individuals. Values for $x_1$, $x_2$, $x_3$ etc., representing in this instance methylation percentage at different cytosine locus would be derived from the individual being tested while the n-values would be derived from the logistic regression analysis of the large reference population of affected (TBI) and unaffected cases mentioned above. Based on these values, an individual's probability of having a type of TBI can be quantitatively estimated. Probability thresholds are used to define individuals at high risk (e.g. a probability of ≤1/100 of TBI may be used to define a high risk individual triggering further evaluation, while individuals with low risk e.g. <1/100 would require no further follow-up. The threshold used will among other factors be based on the diagnostic sensitivity (number of TBI cases correctly identified), specificity (number of non-TBI cases correctly identified as normal) risk and influenced by cost of CT or MRI scans and related interventions pursuant to the designation of an individual as "high risk" for TBI and such factors. Logistic regression analysis is well known as a method in disease screening for estimating an individual's risk for having a disorder. Computer programs such as ROCR package version 3.4 (https://CRAN.R-proiect.org/package=ROCR) can simplify and automate the process of generating the AUC values. In addition, other quantifiable parameters e.g. SAC score can be integrated into the logistic regression to calculate individual risk of Concussion.

Logistic regression analysis can also be used for calculation of sensitivity and specificity for the prediction of TBI based on methylation of cytosine loci.

It has been demonstrated that statistically highly significant differences exist in the percentage or level of methylation of individual cytosine nucleotides distributed throughout the genome both within and outside of the genes when cases with TBI are compared to normal unaffected cases. Cytosines demonstrating methylation differences are distributed both inside and outside of (CpG islands, shores) and genes. The disclosure describes methylation markers for distinguishing TBI from normal cases.

Particular embodiments describe a panel of cytosine markers for distinguishing individual categories of TBI from normal cases and also for distinguishing TBI as a group from normal cases without TBI. The disclosure includes risk assessment at any time or period during postnatal life.

Additional embodiments describe the use of statistical algorithms and methods for estimating the individual risk of being diagnosed with TBI based on methylation levels al informative cytosine loci.

Embodiments describe methods for diagnosing TBI based on measurement of the frequency or percentage methylation of cytosine nucleotides in various identified loci in the DNA of individuals. The present disclosure describes a method comprising the steps of: A) obtaining a sample from a patient; B) extracting DNA from blood specimens; C) assaying to determine the percentage methylation of cytosine al loci throughout the genome; D) comparing the cytosine methylation level of the patient to a well characterized population of normal and TBI groups; and E) calculating the individual risk of TBI based on the cytosine methylation level al different sites throughout the genome.

In embodiments, the sample is body fluid from which DNA is extracted for assessment of DNA methylation is blood. Examples of body fluid includes urine, and saliva. In embodiments, the sample is a tissue sample of a patient. Examples of tissue samples include hair and other sources of cells such as buccal swabs etc.

In embodiments, the methylation sites are used in many different combinations to calculate the probability of diagnosing TBI in an individual.

In embodiments, the patient is an adult. In embodiments, the patient is a newborn. In embodiments, the patient is a pediatric patient.

In embodiments, the disclosure describes determining the risk of being diagnosed with TBI at any time during any period of life from birth until death. Because concussion is a significant risk at the extremes of life, small children and the elderly and periods in between, young adolescents due to sports and recreational activities, adults in the military and adults from motor vehicular accidents and alcohol and drug consumption, the testing described for concussion screening can be performed at any age of life. In embodiments, the disclosure describes determining risk of being diagnosed with TBI as a pediatric patient. In embodiments, the disclosure describes determining risk of being diagnosed with mTBI as a pediatric patient. As pointed out however the testing can be justified at any age of life.

In embodiments, the DNA is obtained from cells. In embodiments, the DNA is cell free DNA.

In embodiments, the sample is obtained and stored for purposes of pathological examination. In embodiments, the sample is stored as slides, tissue blocks, or frozen. In embodiments, the TBI can be any of its types such as mTBI.

The present disclosure provides intragenic cytosine markers and their performance as represented by the Area under the ROC curve (AUC) and 95% Confidence Interval (CI) for the detection of TBI versus unaffected controls in Table 2.

In embodiments, measurement of the level or percentage methylation of cytosine nucleotides is obtained using gene or whole genome sequencing techniques. In embodiments, the assay is a bisulfite-based methylation assay or DNA methylation sequencing to identify methylation changes in individual cytosines throughout the genome.

In embodiments, the disclosure describes a method by which proteins transcribed from the genes described can be measured in body fluids and used to detect and diagnose mild TBI. Proteins are the products of gene transcriptional activity ('gene expression'). Methylation changes in CpG classically results in altered expression of the relevant gene. It stands to reason therefore that the levels of mTBI related proteins in the blood for example will generally reflect the DNA methylation changes (induced by brain trauma) of the relevant genes.

In embodiments, proteins transcribed from related genes can be measured and quantitated in body fluids and or tissues of pregnant mothers or affected individuals.

In another embodiment mRNA produced by affected genes is measured in tissue or body fluids and mRNA levels can be quantitated to determine activity of said genes and used to estimate likelihood of accurately diagnosing TBI. In embodiments, the method further comprises the use of an mRNA genome-wide chip for the measurement of gene activity of genes genome-wide for screening any tissue or body fluids (including blood and saliva) containing mRNA.

Tables of Genes, Genomic Loci, and Metabolomic Markers.

Table 2 provides the list of CpG loci (and associated genes) that can be used individually or in combination for mTBI detection (18 mTBI and 18 unaffected controls). Table 3 provides concentration data from the metabolomic analysis of a subgroup of 17 cases and 18 controls used for combined epigenomic and metabolomic analyses for the prediction of concussion. Tables 4-8 show the performance of epigenetic, metabolomic and clinical and demographic markers individually and in combination for mTBI or concussion detection. Supplementary Tables S1-S3 show the performance of CpG loci in particular categories of genes (miRNA, ORF and LOC genes) for the prediction of mTBI. Supplemental Table S4 shows expanded epigenomic markers for pediatric concussion.

Table 2 provides an extended list of 412 genomic (CpG) loci. One or more, two or more, up to and including all 412 of the genomic loci in Table 2 can be selected for predicting TBI in a patient. This entire set of loci will be used to create a microarray for the for predicting TBI.

Likewise, one, one or more, two or more, up to and including all of the genomic loci and other predictors (metabolomic and clinical markers) in Tables 2-8 can be used in different combinations as laid out for the prediction of TBI in a patient. In embodiments, the one or more selected genomic loci have an AUC of ≥0.60, ≥0.65, ≥0.70, ≥0.75, ≥0.80, ≥0.85, ≥0.90, ≥0.95, ≥0.96, ≥0.97, ≥0.98, or ≥0.99. Ranges described throughout the application include the specified range, the sub-ranges within the specified range, the individual numbers within the range, and the endpoints of the range. For example, description of a range such as from one or more up to 412 includes subranges such as from one or more to 100 or more, from 10 or more to 20 or more, from one or more to five or more, as well as individual numbers within that range, for example, 1, 2, 3, 4, 5, 10, 20, 100, and 173. Moreover, as further example, the description of a range of 0.75 would include all the individual numbers from 0.75 to 1.00 and including 0.75 and 1.0.

In embodiments, differentially methylated genes in the blood DNA of TBI patients include PTGDR, PTGER4, S1P1-S1P4, ADCY8, GRIN2D, PLCG2, FGD3, ARHGAP24, BDNF, PIK3CD, HSPA 1L, PTPrC, PTPN6, HLA-DMA, SIPA1, SIPAL2, INPP4A, FYN, PXN, CDC26, PDE4B, and WNT3. In embodiments, genes associated with TBI include LOC genes, such as LOC100134368 and LOC645323. In embodiments, genes associated with TBI include ORF genes such as C20rf40.

In embodiments, the genes associated with TBI include microRNAs such as miR-24-2, miR-548AS, miR-137, miR-365-1, miR-23A, and miR-27A. MicroRNA (miRNA) is an important epigenetic mechanism and exerts control over DNA methylation and suppresses gene expression among other functions. Therefore, the CpG methylation status of known microRNA genes can be measured instead of measuring actual miRNA levels in the blood to diagnose TBI. Given that DNA methylation status is known to correlate with gene expression, this approach can be used to identify miRNAs that are involved in brain injury.

TABLE 2

Differentially methylated 412 genes with Target ID, Gene ID, chromosome location, % methylation change (compared to controls), and FDR p-value for each gene identified in the analysis

| TargetID | CHR | Gene ID | % Methylation Cases | % Methylation Control | Fold change | FDR p-Val | AUC | CI_lower | CI_upper |
| --- | --- | --- | --- | --- | --- | --- | --- | --- | --- |
| cg06393885 | 5 | GALNT10 | 6.40 | 17.50 | 0.37 | 9.13705E-22 | 0.92 | 0.82 | 1.00 |
| cg20569893 | 17 | FLOT2 | 7.50 | 19.10 | 0.39 | 9.8486E-22 | 0.90 | 0.80 | 1.00 |
| cg00611535 | 12 | RAB5B | 5.63 | 11.66 | 0.48 | 4.16297E-09 | 0.90 | 0.80 | 1.00 |
| cg16882751 | 1 | FCMR | 15.64 | 37.67 | 0.42 | 1.29837E-29 | 0.90 | 0.79 | 1.00 |
| cg06233996 | 18 | NEDD4L | 4.52 | 19.01 | 0.24 | 1.62449E-31 | 0.89 | 0.78 | 1.00 |
| cg24742298 | 17 | SEZ6 | 6.36 | 24.31 | 0.26 | 1.3047E-30 | 0.89 | 0.78 | 1.00 |
| cg19470964 | 15 | LINC01585 | 7.68 | 16.03 | 0.48 | 6.30559E-13 | 0.89 | 0.77 | 1.00 |
| cg24402518 | 10 | PIK3AP1 | 8.67 | 24.02 | 0.36 | 3.95878E-31 | 0.89 | 0.77 | 1.00 |
| cg13528854 | 4 | BST1 | 6.18 | 14.64 | 0.42 | 1.43407E-14 | 0.87 | 0.75 | 0.99 |
| cg05138188 | 19 | KIRREL2 | 12.78 | 6.36 | 2.01 | 1.20458E-10 | 0.87 | 0.75 | 0.99 |
| cg00832555 | 3 | LRRC34 | 8.97 | 21.57 | 0.42 | 1.05316E-22 | 0.87 | 0.75 | 0.99 |
| cg22407154 | 17 | CCL4L1; CCL4L2 | 12.02 | 25.36 | 0.47 | 1.90004E-21 | 0.86 | 0.74 | 0.99 |
| cg18786479 | 1 | CD247 | 2.19 | 4.50 | 0.49 | 0.004573041 | 0.86 | 0.74 | 0.99 |
| cg24129356 | 6 | HLA-DMA | 9.80 | 22.76 | 0.43 | 9.53863E-23 | 0.86 | 0.74 | 0.99 |
| cg21115691 | 1 | FCAMR | 3.49 | 15.43 | 0.23 | 1.35261E-29 | 0.85 | 0.73 | 0.98 |
| cg15762032 | 10 | GAD2 | 5.44 | 14.50 | 0.38 | 4.59479E-17 | 0.85 | 0.73 | 0.98 |
| cg07077221 | 3 | HESRG; CACNA2D3 | 7.83 | 21.94 | 0.36 | 1.252E-28 | 0.85 | 0.73 | 0.98 |

TABLE 2-continued

Differentially methylated 412 genes with Target ID, Gene ID, chromosome location, % methylation change (compared to controls), and FDR p-value for each gene identified in the analysis

| TargetID | CHR | Gene ID | % Methylation Cases | % Methylation Control | Fold change | FDR p-Val | AUC | CI_lower | CI_upper |
|---|---|---|---|---|---|---|---|---|---|
| cg03957481 | 22 | KLHDC7B | 1.91 | 9.56 | 0.20 | 7.81035E−18 | 0.85 | 0.73 | 0.98 |
| cg24684739 | 11 | ZFP91; LPXN; ZFP91-CNTF | 3.54 | 7.56 | 0.47 | 6.93862E−06 | 0.85 | 0.72 | 0.98 |
| cg13631572 | 14 | ADCY4 | 3.64 | 11.95 | 0.30 | 2.77797E−17 | 0.85 | 0.72 | 0.98 |
| cg20601481 | 11 | ANKRD13D | 3.20 | 10.10 | 0.32 | 1.4423E−13 | 0.85 | 0.72 | 0.98 |
| cg12181083 | 8 | SULF1 | 7.80 | 16.13 | 0.48 | 8.86432E−13 | 0.85 | 0.72 | 0.98 |
| cg24104241 | 1 | ACTA1 | 8.39 | 18.97 | 0.44 | 6.87272E−18 | 0.85 | 0.71 | 0.98 |
| cg22026423 | 10 | BUB3 | 6.28 | 17.50 | 0.36 | 2.73084E−22 | 0.85 | 0.71 | 0.98 |
| cg19071452 | 2 | NMI | 6.57 | 18.15 | 0.36 | 6.33629E−23 | 0.85 | 0.71 | 0.98 |
| cg07801620 | 11 | CAT | 13.91 | 28.13 | 0.49 | 5.50739E−22 | 0.84 | 0.71 | 0.97 |
| cg01967102 | 3 | KAT2B | 14.51 | 33.55 | 0.43 | 2.43888E−30 | 0.84 | 0.71 | 0.97 |
| cg03343063 | 1 | PLEKHM2 | 5.69 | 19.34 | 0.29 | 7.31143E−31 | 0.84 | 0.71 | 0.97 |
| cg03307717 | 21 | U2AF1 | 10.75 | 22.02 | 0.49 | 2.15156E−17 | 0.84 | 0.71 | 0.97 |
| cg17078116 | 8 | NEFM | 4.65 | 16.64 | 0.28 | 2.21457E−27 | 0.84 | 0.70 | 0.97 |
| cg08218360 | 6 | NUDT3; RPS10 | 10.38 | 22.03 | 0.47 | 1.08889E−18 | 0.84 | 0.70 | 0.97 |
| cg16927040 | 3 | SST | 5.71 | 13.46 | 0.42 | 3.49497E−13 | 0.84 | 0.70 | 0.97 |
| cg00698595 | 11 | ETS1 | 7.22 | 15.26 | 0.47 | 1.4772E−12 | 0.83 | 0.70 | 0.97 |
| cg20891481 | 3 | FOXP1 | 6.50 | 14.28 | 0.46 | 1.57149E−12 | 0.83 | 0.70 | 0.97 |
| cg17836354 | 22 | MKL1 | 6.57 | 24.97 | 0.26 | 1.68483E−30 | 0.83 | 0.70 | 0.97 |
| cg22836191 | 8 | CHRNA6 | 5.51 | 17.89 | 0.31 | 4.63598E−27 | 0.83 | 0.69 | 0.97 |
| ch.3.1226245F | 3 | ERC2 | 2.92 | 10.46 | 0.28 | 7.34476E−16 | 0.83 | 0.69 | 0.97 |
| cg24954861 | 15 | IGF1R | 12.74 | 28.85 | 0.44 | 4.31675E−28 | 0.83 | 0.69 | 0.97 |
| cg18490792 | 16 | PLCG2 | 6.60 | 23.39 | 0.28 | 6.55642E−31 | 0.83 | 0.69 | 0.97 |
| cg27599271 | 14 | RIPK3 | 5.54 | 13.99 | 0.40 | 3.34965E−15 | 0.83 | 0.69 | 0.96 |
| cg14503399 | 8 | CPQ | 6.25 | 21.75 | 0.29 | 3.01444E−31 | 0.82 | 0.69 | 0.96 |
| cg19823803 | 4 | KIT; KIT | 7.43 | 18.64 | 0.40 | 9.86694E−21 | 0.82 | 0.69 | 0.96 |
| cg00225623 | 13 | SPATA13 | 5.50 | 14.33 | 0.38 | 2.40298E−16 | 0.82 | 0.69 | 0.96 |
| cg03290752 | 3 | TBL1XR1 | 5.70 | 13.43 | 0.42 | 3.76048E−13 | 0.82 | 0.69 | 0.96 |
| cg01698105 | 6 | LRRC16A | 5.77 | 14.65 | 0.39 | 3.53967E−16 | 0.82 | 0.68 | 0.96 |
| cg03530294 | 22 | APOL3 | 4.99 | 14.22 | 0.35 | 3.59302E−18 | 0.82 | 0.68 | 0.96 |
| cg12386061 | 3 | CTDSPL | 6.99 | 18.63 | 0.38 | 1.59598E−22 | 0.82 | 0.68 | 0.96 |
| cg14666113 | 8 | GATA4 | 3.63 | 12.60 | 0.29 | 2.43589E−19 | 0.82 | 0.68 | 0.96 |
| cg15685268 | 11 | IGSF9B | 5.26 | 11.45 | 0.46 | 1.00771E−09 | 0.82 | 0.68 | 0.96 |
| cg04385966 | 3 | KLHL6 | 4.54 | 16.36 | 0.28 | 4.86807E−27 | 0.82 | 0.68 | 0.96 |
| cg19946512 | 9 | RNF38 | 7.83 | 19.34 | 0.40 | 4.76089E−21 | 0.82 | 0.68 | 0.96 |
| cg26405376 | 5 | RNF44 | 5.60 | 13.73 | 0.41 | 2.69917E−14 | 0.82 | 0.68 | 0.96 |
| cg12205413 | 6 | BACH2 | 6.75 | 14.81 | 0.46 | 4.98124E−13 | 0.82 | 0.68 | 0.96 |
| cg25240468 | 2 | CCT4 | 0.67 | 2.19 | 0.31 | 0.042088096 | 0.82 | 0.68 | 0.96 |
| cg15665792 | 7 | ELMO1 | 15.32 | 31.32 | 0.49 | 2.4182E−25 | 0.82 | 0.68 | 0.96 |
| cg16709232 | 17 | KIF19 | 3.21 | 6.81 | 0.47 | 3.62932E−05 | 0.82 | 0.68 | 0.96 |
| cg05053923 | 5 | LINC00992 | 4.61 | 11.69 | 0.39 | 1.65627E−12 | 0.82 | 0.68 | 0.96 |
| cg24604213 | 2 | SP140L | 4.99 | 13.46 | 0.37 | 6.28074E−16 | 0.82 | 0.68 | 0.96 |
| cg16049690 | 5 | BTNL9 | 10.40 | 23.50 | 0.44 | 1.87114E−22 | 0.81 | 0.67 | 0.96 |
| cg27384352 | 7 | CDK5; SLC4A2 | 4.05 | 8.15 | 0.50 | 8.15584E−06 | 0.81 | 0.67 | 0.96 |
| cg08067617 | 19 | F2RL3 | 5.86 | 15.76 | 0.37 | 6.14802E−19 | 0.81 | 0.67 | 0.96 |
| cg13565152 | 9 | HINT2 | 6.51 | 3.14 | 2.07 | 5.30759E−05 | 0.81 | 0.67 | 0.96 |
| cg16795830 | 6 | LST1 | 4.28 | 18.04 | 0.24 | 1.02775E−31 | 0.81 | 0.67 | 0.96 |
| cg07498879 | 22 | OSM | 4.74 | 20.61 | 0.23 | 3.79848E−31 | 0.81 | 0.67 | 0.96 |
| cg26921036 | 4 | TEC | 7.78 | 24.27 | 0.32 | 5.47344E−31 | 0.81 | 0.67 | 0.96 |
| cg25997979 | 10 | ZMIZ1 | 2.86 | 12.27 | 0.23 | 3.69783E−22 | 0.81 | 0.67 | 0.96 |
| cg15596749 | 1 | BLACAT1 | 6.14 | 14.43 | 0.43 | 3.77171E−14 | 0.81 | 0.67 | 0.95 |
| cg25769852 | 12 | CD69 | 9.75 | 23.00 | 0.42 | 1.43041E−23 | 0.81 | 0.67 | 0.95 |
| cg13620034 | 8 | MSC | 5.72 | 16.61 | 0.34 | 4.30693E−22 | 0.81 | 0.67 | 0.95 |
| cg05601847 | 4 | THAP9 | 9.55 | 26.16 | 0.37 | 5.8866E−31 | 0.81 | 0.67 | 0.95 |
| cg05845319 | 3 | EPM2AIP1; MLH1 | 5.35 | 11.08 | 0.48 | 1.34497E−08 | 0.81 | 0.66 | 0.95 |
| cg17579384 | 1 | GCSAML | 7.14 | 15.58 | 0.46 | 1.39399E−13 | 0.81 | 0.66 | 0.95 |
| cg04104119 | 5 | LNPEP | 10.46 | 28.28 | 0.37 | 1.2027E−30 | 0.81 | 0.66 | 0.95 |
| cg23677243 | 15 | MEIS2 | 8.37 | 18.44 | 0.45 | 1.44489E−16 | 0.81 | 0.66 | 0.95 |
| cg25924217 | 17 | NPTX1 | 5.47 | 13.71 | 0.40 | 9.9582E−15 | 0.81 | 0.66 | 0.95 |
| cg04192740 | 5 | STK10 | 5.97 | 18.98 | 0.31 | 3.05439E−28 | 0.81 | 0.66 | 0.95 |
| cg00663077 | 4 | ZFP42 | 10.05 | 21.77 | 0.46 | 3.33961E−19 | 0.81 | 0.66 | 0.95 |
| cg04379606 | 16 | ZNF75A; TIGD7 | 3.81 | 12.13 | 0.31 | 4.82615E−17 | 0.81 | 0.66 | 0.95 |
| cg05851250 | 3 | ANO10 | 7.15 | 22.84 | 0.31 | 3.38947E−31 | 0.81 | 0.66 | 0.95 |
| cg21599974 | 4 | ARHGAP24 | 5.68 | 13.21 | 0.43 | 1.24889E−12 | 0.81 | 0.66 | 0.95 |
| cg09243716 | 8 | DLC1 | 7.13 | 22.50 | 0.32 | 2.77884E−31 | 0.81 | 0.66 | 0.95 |
| cg10303411 | 6 | FAM65B | 5.24 | 22.70 | 0.23 | 9.79114E−31 | 0.81 | 0.66 | 0.95 |
| cg12378187 | 3 | FEZF2 | 8.96 | 22.33 | 0.40 | 6.90954E−25 | 0.81 | 0.66 | 0.95 |
| cg25563256 | 17 | FGF11 | 12.37 | 25.83 | 0.48 | 1.99317E−21 | 0.81 | 0.66 | 0.95 |
| cg24134845 | 10 | HPSE2 | 3.03 | 7.86 | 0.39 | 4.31193E−08 | 0.81 | 0.66 | 0.95 |
| cg26720543 | 2 | INPP5D | 4.61 | 19.78 | 0.23 | 2.4696E−31 | 0.81 | 0.66 | 0.95 |
| cg00231338 | 12 | PLBD1 | 11.22 | 26.86 | 0.42 | 1.6683E−28 | 0.81 | 0.66 | 0.95 |
| cg27510024 | 2 | RFX8 | 11.82 | 24.71 | 0.48 | 1.72808E−20 | 0.81 | 0.66 | 0.95 |
| cg18351999 | 11 | SIGIRR | 6.28 | 13.50 | 0.46 | 2.09497E−11 | 0.81 | 0.66 | 0.95 |
| cg18419977 | 11 | SLC22A18AS; SLC22A18 | 6.13 | 15.17 | 0.40 | 3.47273E−16 | 0.81 | 0.66 | 0.95 |

TABLE 2-continued

Differentially methylated 412 genes with Target ID, Gene ID, chromosome location, % methylation change (compared to controls), and FDR p-value for each gene identified in the analysis

| TargetID | CHR | Gene ID | % Methylation Cases | % Methylation Control | Fold change | FDR p-Val | AUC | CI_lower | CI_upper |
|---|---|---|---|---|---|---|---|---|---|
| cg16117781 | 1 | TNFRSF9 | 16.06 | 32.85 | 0.49 | 9.26684E-27 | 0.81 | 0.66 | 0.95 |
| cg17277890 | 11 | TRIM22 | 6.06 | 15.00 | 0.40 | 5.52092E-16 | 0.81 | 0.66 | 0.95 |
| cg07212778 | 2 | C1QL2 | 2.06 | 9.06 | 0.23 | 2.03981E-15 | 0.80 | 0.66 | 0.95 |
| cg20293777 | 4 | HPGDS | 6.28 | 20.07 | 0.31 | 3.35181E-30 | 0.80 | 0.66 | 0.95 |
| cg03286855 | 7 | RAPGEF5 | 12.31 | 29.45 | 0.42 | 8.04544E-31 | 0.80 | 0.66 | 0.95 |
| cg05651417 | 7 | SNX10 | 6.10 | 20.25 | 0.30 | 1.31649E-31 | 0.80 | 0.66 | 0.95 |
| cg14415885 | 1 | TBX15 | 2.62 | 9.01 | 0.29 | 9.05712E-13 | 0.80 | 0.66 | 0.95 |
| cg18801599 | 17 | TMEM101 | 4.70 | 10.90 | 0.43 | 3.60861E-10 | 0.80 | 0.66 | 0.95 |
| cg25526061 | 10 | ADAM8 | 4.80 | 19.29 | 0.25 | 1.6176E-31 | 0.80 | 0.65 | 0.95 |
| cg02812947 | 8 | ADCY8 | 4.31 | 12.72 | 0.34 | 1.24617E-16 | 0.80 | 0.65 | 0.95 |
| cg00897144 | 13 | ALOX5AP | 7.93 | 17.86 | 0.44 | 1.1661E-16 | 0.80 | 0.65 | 0.95 |
| cg13448968 | 2 | CHPF | 1.08 | 2.72 | 0.40 | 0.032177843 | 0.80 | 0.65 | 0.95 |
| cg00514609 | 11 | CRYAB; HSPB2 | 8.29 | 18.62 | 0.45 | 2.46986E-17 | 0.80 | 0.65 | 0.95 |
| cg00157796 | 6 | FNDC1 | 1.61 | 5.59 | 0.29 | 5.33361E-07 | 0.80 | 0.65 | 0.95 |
| cg27035251 | 19 | JAK3 | 6.88 | 14.78 | 0.47 | 1.59087E-12 | 0.80 | 0.65 | 0.95 |
| cg22761241 | 1 | LINC01225 | 11.65 | 27.59 | 0.42 | 7.66047E-29 | 0.80 | 0.65 | 0.95 |
| cg06648277 | 10 | NKX6-2 | 3.74 | 15.29 | 0.24 | 9.86624E-28 | 0.80 | 0.65 | 0.95 |
| cg10464462 | 17 | RFFL | 3.03 | 15.46 | 0.20 | 4.44216E-32 | 0.80 | 0.65 | 0.95 |
| cg15444626 | 17 | SAMD14 | 5.95 | 12.28 | 0.48 | 1.42937E-09 | 0.80 | 0.65 | 0.95 |
| cg04184297 | 17 | SLC16A3 | 2.70 | 19.51 | 0.14 | 6.61457E-31 | 0.80 | 0.65 | 0.95 |
| cg00803453 | 2 | SPEG | 4.35 | 11.65 | 0.37 | 2.40505E-13 | 0.80 | 0.65 | 0.95 |
| cg27531206 | 1 | UCK2 | 7.57 | 26.54 | 0.29 | 2.34644E-30 | 0.80 | 0.65 | 0.95 |
| cg16478871 | 16 | XPO6. | 11.63 | 30.11 | 0.39 | 1.7731E-30 | 0.80 | 0.65 | 0.95 |
| cg16536329 | 5 | ZNF454 | 10.79 | 22.55 | 0.48 | 1.33747E-18 | 0.80 | 0.65 | 0.95 |
| cg17240760 | 1 | CD53 | 8.91 | 18.43 | 0.48 | 9.94145E-15 | 0.80 | 0.65 | 0.94 |
| cg06470626 | 16 | CDR2 | 8.54 | 17.59 | 0.49 | 7.20618E-14 | 0.80 | 0.65 | 0.94 |
| cg03647767 | 10 | JMJD1C | 6.98 | 25.45 | 0.27 | 1.75730E-30 | 0.80 | 0.65 | 0.94 |
| cg09965733 | 14 | LRFN5 | 6.09 | 12.18 | 0.50 | 6.17764E-09 | 0.80 | 0.65 | 0.94 |
| cg19651694 | 11 | PHOX2A | 5.40 | 14.97 | 0.36 | 1.27784E-18 | 0.80 | 0.65 | 0.94 |
| cg23413809 | 2 | SIX2 | 4.13 | 22.22 | 0.19 | 1.40809E-30 | 0.80 | 0.65 | 0.94 |
| cg19391966 | 17 | TNK1 | 3.90 | 13.72 | 0.28 | 1.20881E-21 | 0.80 | 0.65 | 0.94 |
| cg00381233 | 7 | VOPP1 | 7.99 | 23.05 | 0.35 | 2.64118E-31 | 0.80 | 0.65 | 0.94 |
| cg06444282 | 1 | VWA5B1 | 7.86 | 16.24 | 0.48 | 7.51673E-13 | 0.80 | 0.65 | 0.94 |
| cg06675190 | 15 | ACAN | 3.07 | 10.25 | 0.30 | 1.44917E-14 | 0.79 | 0.64 | 0.94 |
| cg20779757 | 15 | ANPEP | 7.14 | 16.13 | 0.44 | 5.42639E-15 | 0.79 | 0.64 | 0.94 |
| cg04263436 | 6 | B3GALT4 | 2.67 | 9.94 | 0.27 | 2.26722E-15 | 0.79 | 0.64 | 0.94 |
| cg04510788 | 1 | GRIK3 | 3.65 | 10.65 | 0.34 | 2.54762E-13 | 0.79 | 0.64 | 0.94 |
| cg25643819 | 6 | HLA-L | 2.34 | 5.33 | 0.44 | 0.000272499 | 0.79 | 0.64 | 0.94 |
| cg06460568 | 11 | IGF2AS; INS-IGF2; IGF2 | 3.91 | 10.69 | 0.37 | 1.97523E-12 | 0.79 | 0.64 | 0.94 |
| cg14085715 | 7 | MACC1 | 6.20 | 16.43 | 0.38 | 1.79412E-19 | 0.79 | 0.64 | 0.94 |
| cg14373499 | 2 | ACTR3 | 2.27 | 5.03 | 0.45 | 0.000740078 | 0.79 | 0.64 | 0.94 |
| cg08923160 | 16 | APOB48R | 10.98 | 25.10 | 0.44 | 1.51052E-24 | 0.79 | 0.64 | 0.94 |
| ch.10.1562909R | 10 | CCDC109A | 5.12 | 10.75 | 0.48 | 1.64879E-08 | 0.79 | 0.64 | 0.94 |
| cg00166343 | 17 | CRLF3 | 13.49 | 27.64 | 0.49 | 3.47496E-22 | 0.79 | 0.64 | 0.94 |
| cg21215767 | 2 | EN1 | 8.21 | 17.05 | 0.48 | 1.17226E-13 | 0.79 | 0.64 | 0.94 |
| cg05109049 | 17 | EVI2B; NF1 | 9.38 | 26.66 | 0.35 | 8.78206E-31 | 0.79 | 0.64 | 0.94 |
| cg25720793 | 1 | F11R | 4.11 | 12.80 | 0.32 | 9.75525E-18 | 0.79 | 0.64 | 0.94 |
| cg23474501 | 10 | GPR123 | 3.28 | 12.97 | 0.25 | 2.66714E-22 | 0.79 | 0.64 | 0.94 |
| cg00983904 | 12 | IFFO1 | 10.23 | 24.83 | 0.41 | 8.58091E-27 | 0.79 | 0.64 | 0.94 |
| ch.8.1136903F | 8 | SNTG1 | 3.41 | 8.49 | 0.40 | 1.94795E-08 | 0.79 | 0.64 | 0.94 |
| cg10143426 | 1 | TP73; WDR8 | 4.24 | 13.34 | 0.32 | 7.8074E-19 | 0.79 | 0.64 | 0.94 |
| cg16016319 | 1 | TRIM63 | 6.48 | 19.98 | 0.32 | 6.157E-29 | 0.79 | 0.64 | 0.94 |
| cg26693584 | 16 | WWOX | 7.18 | 25.13 | 0.29 | 1.30206E-30 | 0.79 | 0.64 | 0.94 |
| cg23729050 | 2 | KLF7 | 1.52 | 3.15 | 0.48 | 0.040426451 | 0.79 | 0.64 | 0.94 |
| cg11753540 | 11 | ADM | 3.59 | 12.71 | 0.28 | 6.93513E-20 | 0.79 | 0.64 | 0.94 |
| cg04052466 | 19 | AMH | 10.56 | 21.13 | 0.50 | 7.11424E-16 | 0.79 | 0.64 | 0.94 |
| cg13785898 | 16 | CKLF-CMTM1; CKLF; TK2 | 5.33 | 11.29 | 0.47 | 3.72082E-09 | 0.79 | 0.64 | 0.94 |
| cg01974370 | 1 | NBPF20 | 5.30 | 15.55 | 0.34 | 9.20672E-21 | 0.79 | 0.64 | 0.94 |
| cg13916762 | 6 | NHSL1 | 8.17 | 16.77 | 0.49 | 4.03382E-13 | 0.79 | 0.64 | 0.94 |
| cg13795063 | 17 | RARA | 3.96 | 10.21 | 0.39 | 6.1149E-11 | 0.79 | 0.64 | 0.94 |
| cg11686792 | 13 | RASA3 | 5.21 | 17.79 | 0.29 | 2.88503E-28 | 0.79 | 0.64 | 0.94 |
| cg12881222 | 7 | STEAP1B | 9.85 | 22.39 | 0.44 | 1.47903E-21 | 0.79 | 0.64 | 0.94 |
| cg02253612 | 7 | STX1A | 3.57 | 16.07 | 0.22 | 2.45427E-31 | 0.79 | 0.64 | 0.94 |
| cg01307939 | 7 | TMEM130 | 1.01 | 4.19 | 0.24 | 2.28342E-05 | 0.79 | 0.64 | 0.94 |
| cg01636080 | 1 | WASF2 | 10.58 | 23.94 | 0.44 | 6.13893E-23 | 0.79 | 0.64 | 0.94 |
| cg19934381 | 17 | B3GNTL1 | 6.51 | 14.75 | 0.44 | 1.13733E-13 | 0.78 | 0.63 | 0.94 |
| cg20305095 | 2 | CUL3 | 13.55 | 30.11 | 0.45 | 1.73681E-28 | 0.78 | 0.63 | 0.94 |
| cg10109500 | 3 | GHSR | 7.68 | 17.43 | 0.44 | 1.89253E-16 | 0.78 | 0.63 | 0.94 |
| cg18752527 | 2 | HECW2 | 9.50 | 21.94 | 0.43 | 1.15181E-21 | 0.78 | 0.63 | 0.94 |
| cg00091953 | 4 | INPP4B | 4.42 | 9.43 | 0.47 | 1.43101E-07 | 0.78 | 0.63 | 0.94 |
| cg11572340 | 10 | KCNIP2 | 5.67 | 12.03 | 0.47 | 8.15716E-10 | 0.78 | 0.63 | 0.94 |
| cg15531403 | 8 | NPBWR1 | 3.34 | 8.44 | 0.40 | 1.5969E-08 | 0.78 | 0.63 | 0.94 |

TABLE 2-continued

Differentially methylated 412 genes with Target ID, Gene ID, chromosome location, % methylation change (compared to controls), and FDR p-value for each gene identified in the analysis

| TargetID | CHR | Gene ID | % Methylation Cases | % Methylation Control | Fold change | FDR p-Val | AUC | CI_lower | CI_upper |
|---|---|---|---|---|---|---|---|---|---|
| cg19793962 | 1 | PIK3CD | 10.19 | 21.29 | 0.48 | 1.71644E-17 | 0.78 | 0.63 | 0.94 |
| cg27166718 | 6 | PLN | 11.58 | 27.41 | 0.42 | 1.2683E-28 | 0.78 | 0.63 | 0.94 |
| cg14999168 | 11 | PPFIA1 | 9.10 | 25.51 | 0.36 | 5.2131E-31 | 0.78 | 0.63 | 0.94 |
| cg18954401 | 4 | PRDM8 | 11.72 | 24.72 | 0.47 | 7.33058E-21 | 0.78 | 0.63 | 0.94 |
| cg05694921 | 1 | PTPRU | 9.79 | 27.08 | 0.36 | 8.81648E-31 | 0.78 | 0.63 | 0.94 |
| cg12691994 | 1 | RASSF5 | 8.35 | 17.15 | 0.49 | 1.88136E-13 | 0.78 | 0.63 | 0.94 |
| cg00249511 | 11 | SCT | 4.29 | 18.70 | 0.23 | 1.54523E-31 | 0.78 | 0.63 | 0.94 |
| cg19588399 | 1 | SYTL1 | 1.76 | 4.48 | 0.39 | 0.00056829 | 0.78 | 0.63 | 0.94 |
| cg25552416 | 17 | ZFP3 | 5.65 | 12.35 | 0.46 | 1.2184E-10 | 0.78 | 0.63 | 0.94 |
| cg05433448 | 3 | ATP2C1 | 4.93 | 11.83 | 0.42 | 9.58211E-12 | 0.78 | 0.63 | 0.93 |
| cg23906261 | 10 | GFRA1 | 6.12 | 16.17 | 0.38 | 4.40045E-19 | 0.78 | 0.63 | 0.93 |
| cg21217024 | 11 | GRIA4 | 4.09 | 15.45 | 0.26 | 2.3205E-26 | 0.78 | 0.63 | 0.93 |
| cg15731655 | 12 | HOTAIR | 5.51 | 13.32 | 0.41 | 1.58554E-13 | 0.78 | 0.63 | 0.93 |
| cg06203744 | 2 | KIAA2012 | 12.08 | 27.57 | 0.44 | 3.98819E-27 | 0.78 | 0.63 | 0.93 |
| cg17213699 | 12 | LAG3 | 4.31 | 19.17 | 0.22 | 2.04164E-31 | 0.78 | 0.63 | 0.93 |
| cg11041734 | 7 | LIMK1 | 4.57 | 9.32 | 0.49 | 6.73342E-07 | 0.78 | 0.63 | 0.93 |
| cg03887163 | 1 | LMX1A | 6.33 | 14.41 | 0.44 | 2.00385E-13 | 0.78 | 0.63 | 0.93 |
| cg19677607 | 8 | NEFM | 2.66 | 10.76 | 0.25 | 4.54039E-18 | 0.78 | 0.63 | 0.93 |
| cg14104842 | 7 | NRCAM | 12.99 | 27.28 | 0.48 | 5.62531E-23 | 0.78 | 0.63 | 0.93 |
| cg16709110 | 11 | SLC25A22 | 3.42 | 7.52 | 0.46 | 4.02408E-06 | 0.78 | 0.63 | 0.93 |
| cg12610471 | 10 | SPAG6 | 11.74 | 24.84 | 0.47 | 4.11033E-21 | 0.78 | 0.63 | 0.93 |
| cg06147863 | 11 | SPI1 | 11.94 | 25.19 | 0.47 | 2.7185E-21 | 0.78 | 0.63 | 0.93 |
| cg00799539 | 12 | ASCL1 | 8.16 | 19.23 | 0.42 | 1.81578E-19 | 0.78 | 0.62 | 0.93 |
| cg27234340 | 17 | ASGR1 | 5.63 | 13.35 | 0.42 | 3.53071E-13 | 0.78 | 0.62 | 0.93 |
| cg13073773 | 14 | GSC | 3.91 | 15.26 | 0.26 | 1.17705E-26 | 0.78 | 0.62 | 0.93 |
| cg16931416 | 10 | INPP5A | 4.00 | 13.77 | 0.29 | 2.40886E-21 | 0.78 | 0.62 | 0.93 |
| cg08972954 | 5 | ITK | 5.77 | 18.05 | 0.32 | 2.54951E-26 | 0.78 | 0.62 | 0.93 |
| cg26082690 | 10 | KIAA1279 | 2.73 | 6.35 | 0.43 | 1.95375E-05 | 0.78 | 0.62 | 0.93 |
| cg21340223 | 19 | LAIR1 | 7.08 | 19.68 | 0.36 | 3.02029E-25 | 0.78 | 0.62 | 0.93 |
| cg03521113 | 12 | LRMP | 2.88 | 12.95 | 0.22 | 2.36372E-24 | 0.78 | 0.62 | 0.93 |
| cg26668608 | 2 | PSD4 | 5.35 | 21.43 | 0.25 | 4.29128E-31 | 0.78 | 0.62 | 0.93 |
| cg16902746 | 19 | PTPRS | 7.44 | 18.94 | 0.39 | 1.59183E-21 | 0.78 | 0.62 | 0.93 |
| cg11696165 | 12 | PXN | 12.82 | 26.42 | 0.49 | 2.18201E-21 | 0.78 | 0.62 | 0.93 |
| cg18024479 | 7 | TFPI2 | 7.89 | 16.13 | 0.49 | 1.68159E-12 | 0.78 | 0.62 | 0.93 |
| cg12798338 | 17 | TMC8; TMC6 | 4.09 | 17.86 | 0.23 | 1.03499E-31 | 0.78 | 0.62 | 0.93 |
| cg23724557 | 3 | ZBTB20 | 9.65 | 20.97 | 0.46 | 1.5603E-18 | 0.78 | 0.62 | 0.93 |
| cg13121699 | 2 | ZNF804A | 3.13 | 7.44 | 0.42 | 9.38151E-07 | 0.78 | 0.62 | 0.93 |
| cg05070626 | 16 | SYT17 | 3.65 | 10.52 | 0.35 | 6.01618E-13 | 0.78 | 0.62 | 0.93 |
| cg11085070 | 9 | TTF1 | 8.85 | 23.59 | 0.38 | 5.00196E-29 | 0.78 | 0.62 | 0.93 |
| cg26182487 | 5 | ABLIM3 | 3.84 | 11.55 | 0.33 | 3.89261E-15 | 0.77 | 0.62 | 0.93 |
| cg04889100 | 17 | ARSG | 3.49 | 20.75 | 0.17 | 8.71941E-31 | 0.77 | 0.62 | 0.93 |
| cg09870066 | 2 | CNRIP1 | 6.28 | 15.03 | 0.42 | 3.02651E-15 | 0.77 | 0.62 | 0.93 |
| cg25614907 | 5 | CTD-2194D22.4; IRX4 | 10.73 | 21.53 | 0.50 | 2.88755E-16 | 0.77 | 0.62 | 0.93 |
| cg06086267 | 7 | CUX1 | 5.84 | 21.94 | 0.27 | 4.32444E-31 | 0.77 | 0.62 | 0.93 |
| cg26961808 | 7 | FLNC | 4.40 | 16.05 | 0.27 | 1.01563E-26 | 0.77 | 0.62 | 0.93 |
| cg19485539 | 10 | GFRA1 | 3.96 | 10.72 | 0.37 | 2.50302E-12 | 0.77 | 0.62 | 0.93 |
| cg09092089 | 7 | GIMAP7 | 7.30 | 24.42 | 0.30 | 7.94332E-31 | 0.77 | 0.62 | 0.93 |
| cg27210998 | 17 | GRB2 | 8.17 | 23.11 | 0.35 | 1.14086E-30 | 0.77 | 0.62 | 0.93 |
| cg17736443 | 6 | HIST1H2AJ | 5.89 | 13.52 | 0.44 | 1.00813E-12 | 0.77 | 0.62 | 0.93 |
| cg02694427 | 2 | HOXD12 | 10.67 | 22.86 | 0.47 | 8.71401E-20 | 0.77 | 0.62 | 0.93 |
| cg26902581 | 2 | ITGA6 | 8.88 | 21.29 | 0.42 | 2.81476E-22 | 0.77 | 0.62 | 0.93 |
| cg23807071 | 7 | MAD1L1 | 6.73 | 17.61 | 0.38 | 1.10289E-20 | 0.77 | 0.62 | 0.93 |
| cg07998137 | 3 | MAGI1 | 8.87 | 20.81 | 0.43 | 5.05621E-21 | 0.77 | 0.62 | 0.93 |
| cg18348337 | 5 | MCC | 4.86 | 11.30 | 0.43 | 1.2342E-10 | 0.77 | 0.62 | 0.93 |
| cg07272395 | 4 | MGAT4D | 6.28 | 14.75 | 0.43 | 1.7309E-14 | 0.77 | 0.62 | 0.93 |
| cg11257728 | 22 | PARVG | 6.20 | 12.97 | 0.48 | 2.10096E-10 | 0.77 | 0.62 | 0.93 |
| cg01599770 | 1 | PDE4B | 10.20 | 22.27 | 0.46 | 5.81819E-20 | 0.77 | 0.62 | 0.93 |
| cg03656996 | 15 | PLCB2 | 3.97 | 15.69 | 0.25 | 8.93827E-28 | 0.77 | 0.62 | 0.93 |
| cg05021267 | 20 | POFUT1 | 12.33 | 28.61 | 0.43 | 5.05413E-29 | 0.77 | 0.62 | 0.93 |
| cg20684253 | 16 | PRKCB | 5.70 | 13.96 | 0.41 | 1.54928E-14 | 0.77 | 0.62 | 0.93 |
| cg27634876 | 14 | PTGDR | 3.43 | 12.55 | 0.27 | 3.6212E-20 | 0.77 | 0.62 | 0.93 |
| cg02353184 | 10 | SFMBT2 | 4.11 | 9.75 | 0.42 | 2.81805E-09 | 0.77 | 0.62 | 0.93 |
| cg24211504 | 6 | SIM1 | 7.71 | 17.94 | 0.43 | 1.11055E-17 | 0.77 | 0.62 | 0.93 |
| cg13320626 | 5 | ST8SIA4 | 4.41 | 9.00 | 0.49 | 1.2438E-06 | 0.77 | 0.62 | 0.93 |
| cg09085842 | 6 | HSPA1A; HSPA1L | 1.47 | 5.98 | 0.25 | 1.53597E-08 | 0.77 | 0.62 | 0.93 |
| cg15917517 | 12 | APPL2 | 13.48 | 28.17 | 0.48 | 1.44843E-23 | 0.77 | 0.62 | 0.93 |
| cg17680773 | 16 | ATF7IP2 | 4.20 | 9.93 | 0.42 | 1.99543E-09 | 0.77 | 0.62 | 0.93 |
| cg17669121 | 12 | ATP6V0A2 | 15.43 | 31.30 | 0.49 | 6.70897E-25 | 0.77 | 0.62 | 0.93 |
| cg01555705 | 16 | CX3CL1 | 8.33 | 23.17 | 0.36 | 4.34559E-30 | 0.77 | 0.62 | 0.93 |
| cg06085985 | 11 | EFCAB4A | 10.13 | 20.66 | 0.49 | 3.87875E-16 | 0.77 | 0.62 | 0.93 |
| cg00037681 | 12 | FAM113B | 5.96 | 23.59 | 0.25 | 1.07984E-30 | 0.77 | 0.62 | 0.93 |
| cg25975712 | 22 | FAM19A5 | 2.57 | 8.60 | 0.30 | 9.34854E-12 | 0.77 | 0.62 | 0.93 |
| cg12079322 | 2 | GALNT13 | 2.17 | 10.63 | 0.20 | 3.84937E-20 | 0.77 | 0.62 | 0.93 |

TABLE 2-continued

Differentially methylated 412 genes with Target ID, Gene ID, chromosome location, % methylation change (compared to controls), and FDR p-value for each gene identified in the analysis

| TargetID | CHR | Gene ID | % Methylation Cases | % Methylation Control | Fold change | FDR p-Val | AUC | CI_lower | CI_upper |
|---|---|---|---|---|---|---|---|---|---|
| cg03852144 | 5 | GLRX | 9.86 | 21.67 | 0.45 | 1.32248E-19 | 0.77 | 0.62 | 0.93 |
| cg05040232 | 3 | GP5 | 6.11 | 16.24 | 0.38 | 2.70631E-19 | 0.77 | 0.62 | 0.93 |
| cg23849169 | 6 | HCG4 | 7.23 | 16.76 | 0.43 | 2.40464E-16 | 0.77 | 0.62 | 0.93 |
| cg18122874 | 22 | IL17RA | 6.01 | 21.26 | 0.28 | 2.59595E-31 | 0.77 | 0.62 | 0.93 |
| cg04167833 | 5 | LCP2 | 2.82 | 9.17 | 0.31 | 2.10401E-12 | 0.77 | 0.62 | 0.93 |
| cg17608171 | 14 | LINC01599 | 5.77 | 15.27 | 0.38 | 6.14739E-18 | 0.77 | 0.62 | 0.93 |
| cg10821845 | 8 | LY6H | 3.70 | 12.00 | 0.31 | 3.84598E-17 | 0.77 | 0.62 | 0.93 |
| cg27071460 | 5 | PTGER4 | 2.63 | 14.56 | 0.18 | 1.55329E-31 | 0.77 | 0.62 | 0.93 |
| cg02970551 | 1 | RUNX3 | 5.40 | 11.41 | 0.47 | 3.29817E-09 | 0.77 | 0.62 | 0.93 |
| cg05555207 | 12 | TBX5 | 6.39 | 13.12 | 0.49 | 3.65195E-10 | 0.77 | 0.62 | 0.93 |
| cg11852643 | 6 | TCP11 | 2.61 | 16.52 | 0.16 | 1.13579E-31 | 0.77 | 0.62 | 0.93 |
| cg07836142 | 6 | ZSCAN23 | 4.82 | 12.72 | 0.38 | 1.69033E-14 | 0.77 | 0.62 | 0.93 |
| cg03094728 | 7 | AKAP9 | 11.40 | 24.54 | 0.46 | 1.63217E-21 | 0.77 | 0.61 | 0.92 |
| cg19977280 | 22 | APOBEC3D | 4.86 | 14.80 | 0.33 | 1.78762E-20 | 0.77 | 0.61 | 0.92 |
| cg23953831 | 1 | CD101 | 6.80 | 22.82 | 0.30 | 4.13588E-31 | 0.77 | 0.61 | 0.92 |
| cg26754426 | 3 | CD200R1 | 9.07 | 25.03 | 0.36 | 3.99339E-31 | 0.77 | 0.61 | 0.92 |
| cg10098353 | 2 | CD28 | 8.64 | 24.90 | 0.35 | 4.771E-31 | 0.77 | 0.61 | 0.92 |
| cg16732780 | 5 | CDHR2 | 9.15 | 26.91 | 0.34 | 1.15971E-30 | 0.77 | 0.61 | 0.92 |
| cg09142829 | 12 | CLEC4A | 13.52 | 27.38 | 0.49 | 2.00105E-21 | 0.77 | 0.61 | 0.92 |
| cg13409544 | 14 | ERO1A | 4.91 | 12.70 | 0.39 | 4.43689E-14 | 0.77 | 0.61 | 0.92 |
| cg27134386 | 4 | GABRA2 | 4.42 | 9.95 | 0.44 | 9.34098E-09 | 0.77 | 0.61 | 0.92 |
| cg00347757 | 13 | GJB2 | 3.32 | 13.07 | 0.25 | 2.02329E-22 | 0.77 | 0.61 | 0.92 |
| cg11083422 | 6 | GLP1R | 3.27 | 8.10 | 0.40 | 6.4454E-08 | 0.77 | 0.61 | 0.92 |
| cg15508761 | 6 | HIVEP2 | 8.15 | 16.96 | 0.48 | 1.2972E-13 | 0.77 | 0.61 | 0.92 |
| cg07625529 | 2 | HOXD10 | 10.64 | 22.81 | 0.47 | 9.24092E-20 | 0.77 | 0.61 | 0.92 |
| cg12690996 | 1 | KLHL21 | 10.76 | 25.69 | 0.42 | 4.52576E-27 | 0.77 | 0.61 | 0.92 |
| cg03309253 | 19 | LTBP4 | 4.27 | 14.05 | 0.30 | 6.35646E-21 | 0.77 | 0.61 | 0.92 |
| cg06157602 | 5 | PCDHGA1; PCDHGA2; PCDHGA3; PCDHGB4; PCDHGB5; PCDHGA6; PCDHGA7; PCDHGA8; PCDHGA9; | 9.75 | 19.76 | 0.49 | 3.31189E-15 | 0.77 | 0.61 | 0.92 |
| cg26070834 | 5 | POLK | 12.44 | 26.28 | 0.47 | 2.30562E-22 | 0.77 | 0.61 | 0.92 |
| cg19113326 | 7 | POU6F2 | 1.50 | 6.18 | 0.24 | 5.37024E-09 | 0.77 | 0.61 | 0.92 |
| cg01782826 | 1 | RCSD1 | 7.48 | 23.67 | 0.32 | 4.59035E-31 | 0.77 | 0.61 | 0.92 |
| cg02996471 | 19 | S1PR4 | 5.81 | 14.86 | 0.39 | 1.36125E-16 | 0.77 | 0.61 | 0.92 |
| cg14287565 | 9 | ARPC5L | 2.96 | 6.39 | 0.46 | 6.22169E-05 | 0.77 | 0.61 | 0.92 |
| cg09980176 | 19 | CCDC151 | 7.25 | 20.34 | 0.36 | 1.81845E-26 | 0.77 | 0.61 | 0.92 |
| cg00579036 | 6 | CMAH | 3.92 | 13.33 | 0.29 | 2.47604E-20 | 0.77 | 0.61 | 0.92 |
| cg10926336 | 10 | DCLRE1A | 14.23 | 29.99 | 0.47 | 1.0936E-25 | 0.77 | 0.61 | 0.92 |
| cg17848763 | 2 | GYPC | 4.33 | 15.39 | 0.28 | 6.33248E-25 | 0.77 | 0.61 | 0.92 |
| cg01178680 | 15 | ISLR2 | 7.73 | 26.26 | 0.29 | 1.82601E-30 | 0.77 | 0.61 | 0.92 |
| cg19814116 | 1 | KCNAB2 | 3.42 | 11.97 | 0.29 | 2.36749E-18 | 0.77 | 0.61 | 0.92 |
| cg21455600 | 7 | KCTD7 | 3.50 | 19.61 | 0.18 | 4.3641E-31 | 0.77 | 0.61 | 0.92 |
| cg18025430 | 11 | MS4A4A | 8.95 | 26.21 | 0.34 | 8.70399E-31 | 0.77 | 0.61 | 0.92 |
| cg12011642 | 17 | MSI2 | 13.35 | 29.49 | 0.45 | 1.46855E-27 | 0.77 | 0.61 | 0.92 |
| cg16046444 | 1 | NR5A2 | 5.41 | 11.62 | 0.47 | 1.1876E-09 | 0.77 | 0.61 | 0.92 |
| cg22060611 | 5 | NRG2 | 4.97 | 10.56 | 0.47 | 1.57662E-08 | 0.77 | 0.61 | 0.92 |
| cg21990556 | 11 | OSBPL5 | 4.54 | 10.24 | 0.44 | 4.06009E-09 | 0.77 | 0.61 | 0.92 |
| cg02147055 | 1 | PTPRC | 9.09 | 27.85 | 0.33 | 2.07274E-30 | 0.77 | 0.61 | 0.92 |
| cg16514615 | 5 | RASGEF1C | 7.21 | 18.21 | 0.40 | 2.18228E-20 | 0.77 | 0.61 | 0.92 |
| cg21720679 | 20 | RBL1 | 14.39 | 31.49 | 0.46 | 3.96069E-29 | 0.77 | 0.61 | 0.92 |
| cg17665121 | 4 | TBC1D1 | 3.43 | 11.78 | 0.29 | 1.15573E-17 | 0.77 | 0.61 | 0.92 |
| cg06786153 | 15 | TBC1D2B | 2.04 | 5.99 | 0.34 | 1.25749E-06 | 0.77 | 0.61 | 0.92 |
| cg04869854 | 11 | ATPGD1 | 10.56 | 23.44 | 0.45 | 1.06167E-21 | 0.76 | 0.60 | 0.92 |
| cg20804072 | 17 | CCL4L1 | 11.07 | 24.63 | 0.45 | 5.6851E-23 | 0.76 | 0.60 | 0.92 |
| cg26433975 | 7 | COM2 | 5.55 | 21.01 | 0.26 | 2.95218E-31 | 0.76 | 0.60 | 0.92 |
| cg17929951 | 20 | CD40 | 4.01 | 10.12 | 0.40 | 1.50857E-10 | 0.76 | 0.60 | 0.92 |
| cg22499994 | 10 | CUBN | 8.15 | 20.21 | 0.40 | 3.44865E-22 | 0.76 | 0.60 | 0.92 |
| cg19047707 | 2 | ECEL1 | 3.29 | 13.62 | 0.24 | 1.76233E-24 | 0.76 | 0.60 | 0.92 |
| cg22504849 | 5 | FBXW11 | 6.78 | 16.53 | 0.41 | 2.05529E-17 | 0.76 | 0.60 | 0.92 |
| cg16732077 | 6 | FYN | 7.62 | 15.43 | 0.49 | 9.96105E-12 | 0.76 | 0.60 | 0.92 |
| cg12751305 | 1 | KCNN3 | 5.48 | 12.93 | 0.42 | 1.28352E-12 | 0.76 | 0.60 | 0.92 |
| cg00231422 | 16 | NOL3 | 5.01 | 11.87 | 0.42 | 1.37135E-11 | 0.76 | 0.60 | 0.92 |
| cg25206113 | 1 | RORC | 7.29 | 23.22 | 0.31 | 3.91138E-31 | 0.76 | 0.60 | 0.92 |
| cg23543318 | 4 | SPON2 | 4.60 | 17.69 | 0.26 | 3.86033E-31 | 0.76 | 0.60 | 0.92 |
| cg11824639 | 1 | TCTEX1D1 | 4.85 | 15.01 | 0.32 | 3.5484E-21 | 0.76 | 0.60 | 0.92 |
| cg22707438 | 11 | DGKZ | 8.75 | 21.63 | 0.40 | 9.09571E-24 | 0.76 | 0.60 | 0.92 |
| cg04207218 | 21 | ERG | 6.79 | 16.78 | 0.40 | 4.73122E-18 | 0.76 | 0.60 | 0.92 |
| cg08596591 | 9 | FGD3 | 2.78 | 16.29 | 0.17 | 8.80088E-32 | 0.76 | 0.60 | 0.92 |
| cg07223253 | 7 | GIMAP8 | 4.16 | 15.12 | 0.27 | 6.29657E-25 | 0.76 | 0.60 | 0.92 |
| cg01185682 | 17 | HLF | 1.75 | 4.34 | 0.40 | 0.000994576 | 0.76 | 0.60 | 0.92 |
| cg05420790 | 12 | HOXC10; HOXC-AS3 | 4.44 | 10.74 | 0.41 | 1.17153E-10 | 0.76 | 0.60 | 0.92 |
| cg15930596 | 12 | KCNA1 | 5.97 | 11.96 | 0.50 | 8.85939E-09 | 0.76 | 0.60 | 0.92 |

TABLE 2-continued

Differentially methylated 412 genes with Target ID, Gene ID, chromosome location, % methylation change (compared to controls), and FDR p-value for each gene identified in the analysis

| TargetID | CHR | Gene ID | % Methylation Cases | % Methylation Control | Fold change | FDR p-Val | AUC | CI_lower | CI_upper |
|---|---|---|---|---|---|---|---|---|---|
| cg06345712 | 11 | MAML2 | 11.01 | 24.27 | 0.45 | 3.23856E−22 | 0.76 | 0.60 | 0.92 |
| cg15278646 | 15 | OCA2 | 1.65 | 4.78 | 0.35 | 6.80447E−05 | 0.76 | 0.60 | 0.92 |
| cg12823387 | 1 | PTPN14 | 14.14 | 32.45 | 0.44 | 1.60559E−30 | 0.76 | 0.60 | 0.92 |
| cg13431464 | 18 | PTPN2 | 12.45 | 26.92 | 0.46 | 5.44044E−24 | 0.76 | 0.60 | 0.92 |
| cg17051560 | 12 | SOCS2 | 3.87 | 9.25 | 0.42 | 8.13509E−09 | 0.76 | 0.60 | 0.92 |
| cg23340017 | 10 | TLX1 | 7.57 | 20.60 | 0.37 | 8.53257E−26 | 0.76 | 0.60 | 0.92 |
| cg23882019 | 8 | TNFRSF10A | 4.48 | 12.29 | 0.36 | 1.17991E−14 | 0.76 | 0.60 | 0.92 |
| cg18058230 | 3 | TNIK | 7.83 | 20.49 | 0.38 | 2.28813E−24 | 0.76 | 0.60 | 0.92 |
| cg19413693 | 1 | VAV3 | 10.51 | 24.11 | 0.44 | 1.13911E−23 | 0.76 | 0.60 | 0.92 |
| cg04136610 | 5 | ADAMTS16 | 7.03 | 16.02 | 0.44 | 4.06145E−15 | 0.76 | 0.60 | 0.92 |
| cg07703495 | 5 | ADCY2 | 6.38 | 13.92 | 0.46 | 4.38412E−12 | 0.76 | 0.60 | 0.92 |
| cg11905061 | 2 | AGAP1 | 13.81 | 28.10 | 0.49 | 3.00947E−22 | 0.76 | 0.60 | 0.92 |
| cg07117012 | 12 | AQP2 | 10.88 | 24.78 | 0.44 | 4.40563E−24 | 0.76 | 0.60 | 0.92 |
| cg08493294 | 2 | DNMT3A | 8.63 | 19.41 | 0.44 | 3.65131E−18 | 0.76 | 0.60 | 0.92 |
| cg24644188 | 5 | FYB | 8.86 | 21.72 | 0.41 | 1.41616E−23 | 0.76 | 0.60 | 0.92 |
| cg14307443 | 4 | GALNTL6 | 2.47 | 9.70 | 0.25 | 1.44757E−15 | 0.76 | 0.60 | 0.92 |
| cg06951565 | 5 | GRM6 | 9.16 | 24.42 | 0.37 | 3.85776E−30 | 0.76 | 0.60 | 0.92 |
| cg11284811 | 1 | HENMT1 | 2.57 | 5.65 | 0.45 | 0.000219182 | 0.76 | 0.60 | 0.92 |
| cg18172877 | 5 | IRX4 | 9.51 | 20.24 | 0.47 | 3.70197E−17 | 0.76 | 0.60 | 0.92 |
| cg21448352 | 2 | KLHL29 | 11.22 | 26.80 | 0.42 | 2.47599E−28 | 0.76 | 0.60 | 0.92 |
| cg12374834 | 1 | LAPTM5 | 7.40 | 24.42 | 0.30 | 7.54815E−31 | 0.76 | 0.60 | 0.92 |
| cg26778001 | 19 | LILRB1 | 6.03 | 13.96 | 0.43 | 2.44007E−13 | 0.76 | 0.60 | 0.92 |
| cg17527798 | 3 | LTF | 9.71 | 20.68 | 0.47 | 1.33291E−17 | 0.76 | 0.60 | 0.92 |
| cg05364588 | 3 | MECOM | 7.86 | 19.20 | 0.41 | 1.45702E−20 | 0.76 | 0.60 | 0.92 |
| cg06499262 | 16 | NFAT5 | 11.06 | 23.09 | 0.48 | 5.16126E−19 | 0.76 | 0.60 | 0.92 |
| cg06252985 | 11 | PC | 3.61 | 8.92 | 0.40 | 7.59572E−09 | 0.76 | 0.60 | 0.92 |
| cg13549444 | 12 | PTPN6 | 4.24 | 18.78 | 0.23 | 1.68008E−31 | 0.76 | 0.60 | 0.92 |
| cg03050022 | 15 | RAB27A | 11.92 | 25.74 | 0.46 | 8.58867E−23 | 0.76 | 0.60 | 0.92 |
| cg25747192 | 3 | RASSF1 | 6.44 | 16.57 | 0.39 | 6.72405E−19 | 0.76 | 0.60 | 0.92 |
| cg05767930 | 12 | RHOF | 3.34 | 17.03 | 0.20 | 9.87378E−32 | 0.76 | 0.60 | 0.92 |
| cg13329322 | 2 | SGPP2 | 12.56 | 30.41 | 0.41 | 1.22587E−30 | 0.76 | 0.60 | 0.92 |
| cg23141934 | 19 | SWSAP1 | 8.05 | 21.61 | 0.37 | 1.07227E−26 | 0.76 | 0.60 | 0.92 |
| cg21201099 | 17 | TBX2 | 8.55 | 19.82 | 0.43 | 1.47177E−19 | 0.76 | 0.60 | 0.92 |
| cg15615160 | 17 | TEKT1 | 1.98 | 4.39 | 0.45 | 0.002541547 | 0.76 | 0.60 | 0.92 |
| cg27641628 | 7 | TMEM140 | 3.38 | 9.01 | 0.37 | 7.21132E−10 | 0.76 | 0.60 | 0.92 |
| cg09474331 | 19 | TTYH1 | 2.77 | 12.76 | 0.22 | 2.59257E−24 | 0.76 | 0.60 | 0.92 |
| cg08112940 | 6 | ADGB | 3.71 | 14.35 | 0.26 | 1.0642E−24 | 0.75 | 0.59 | 0.91 |
| cg16909402 | 1 | CD48 | 11.07 | 24.05 | 0.46 | 1.96713E−21 | 0.75 | 0.59 | 0.91 |
| cg00339488 | 4 | DCHS2 | 5.42 | 15.30 | 0.35 | 1.66422E−19 | 0.75 | 0.59 | 0.91 |
| cg23338503 | 5 | DOCK2 | 7.26 | 14.88 | 0.49 | 1.47167E−11 | 0.75 | 0.59 | 0.91 |
| cg20132609 | 13 | DOCK9 | 3.48 | 13.63 | 0.26 | 1.67637E−23 | 0.75 | 0.59 | 0.91 |
| cg08288130 | 8 | DOK2 | 10.76 | 26.21 | 0.41 | 1.50612E−28 | 0.75 | 0.59 | 0.91 |
| cg10977770 | 1 | ESRRG | 12.17 | 25.21 | 0.48 | 1.44257E−20 | 0.75 | 0.59 | 0.91 |
| cg16441238 | 14 | EVL | 9.39 | 21.02 | 0.45 | 1.30735E−19 | 0.75 | 0.59 | 0.91 |
| cg07106633 | 8 | FABP5 | 3.17 | 6.80 | 0.47 | 3.04945E−05 | 0.75 | 0.59 | 0.91 |
| cg14065576 | 1 | GSTM2 | 2.45 | 6.50 | 0.38 | 1.39644E−06 | 0.75 | 0.59 | 0.91 |
| cg22715094 | 6 | HSPA1A | 5.31 | 10.69 | 0.50 | 7.73312E−08 | 0.75 | 0.59 | 0.91 |
| cg03822198 | 12 | MAP1LC3B2 | 3.26 | 14.42 | 0.23 | 2.22382E−27 | 0.75 | 0.59 | 0.91 |
| cg14201424 | 4 | MGC45800 | 2.92 | 15.81 | 0.18 | 5.93887E−32 | 0.75 | 0.59 | 0.91 |
| cg07637516 | 10 | MXI1 | 7.48 | 15.65 | 0.48 | 1.16087E−12 | 0.75 | 0.59 | 0.91 |
| cg18150439 | 2 | NXPH2 | 2.18 | 11.68 | 0.19 | 8.33465E−24 | 0.75 | 0.59 | 0.91 |
| cg26256223 | 8 | OPLAH | 4.17 | 15.97 | 0.26 | 1.06488E−27 | 0.75 | 0.59 | 0.91 |
| cg06604289 | 1 | PRDM2 | 7.47 | 16.11 | 0.46 | 8.5933E−14 | 0.75 | 0.59 | 0.91 |
| cg21899942 | 14 | RGS6 | 6.37 | 13.74 | 0.46 | 1.1226E−11 | 0.75 | 0.59 | 0.91 |
| cg09762242 | 11 | SIPA1 | 7.31 | 24.02 | 0.30 | 6.27891E−31 | 0.75 | 0.59 | 0.91 |
| cg14015044 | 8 | TNFRSF10C | 0.92 | 10.12 | 0.09 | 1.18898E−25 | 0.75 | 0.59 | 0.91 |
| cg26413174 | 1 | TTC22 | 3.58 | 10.27 | 0.35 | 1.5995E−12 | 0.75 | 0.59 | 0.91 |
| cg26470340 | 10 | ARHGAP21 | 3.87 | 1.87 | 2.07 | 0.010553676 | 0.75 | 0.59 | 0.91 |
| cg14025053 | 8 | BAALC | 6.02 | 15.66 | 0.38 | 5.28266E−18 | 0.75 | 0.59 | 0.91 |
| cg03167496 | 11 | BDNF | 6.20 | 13.42 | 0.46 | 2.00111E−11 | 0.75 | 0.59 | 0.91 |
| cg24674189 | 13 | BRCA2 | 11.86 | 26.00 | 0.46 | 1.05213E−23 | 0.75 | 0.59 | 0.91 |
| cg06159486 | 10 | CACNB2 | 2.36 | 6.06 | 0.39 | 8.16641E−06 | 0.75 | 0.59 | 0.91 |
| cg01729827 | 20 | CBLN4 | 7.16 | 16.46 | 0.44 | 9.04134E−16 | 0.75 | 0.59 | 0.91 |
| cg18507129 | 3 | CHST2 | 3.35 | 6.97 | 0.48 | 3.90766E−05 | 0.75 | 0.59 | 0.91 |
| cg04207385 | 6 | CNR1 | 4.23 | 10.75 | 0.39 | 2.07021E−11 | 0.75 | 0.59 | 0.91 |
| cg22019177 | 11 | DIXDC1 | 4.78 | 14.94 | 0.32 | 2.83692E−21 | 0.75 | 0.59 | 0.91 |
| cg03606646 | 6 | GFOD1 | 9.24 | 18.88 | 0.49 | 9.55987E−15 | 0.75 | 0.59 | 0.91 |
| cg21726846 | 3 | KALRN | 5.63 | 16.14 | 0.35 | 4.6619E−21 | 0.75 | 0.59 | 0.91 |
| cg21696827 | 17 | KIAA0753 | 12.78 | 27.51 | 0.46 | 2.47093E−24 | 0.75 | 0.59 | 0.91 |
| cg26663686 | 8 | LY6H | 4.23 | 8.50 | 0.50 | 4.5937E−06 | 0.75 | 0.59 | 0.91 |
| cg07200038 | 16 | MMP25 | 9.66 | 25.60 | 0.38 | 3.94704E−31 | 0.75 | 0.59 | 0.91 |
| cg01151966 | 10 | NRG3 | 4.74 | 11.87 | 0.40 | 1.64223E−12 | 0.75 | 0.59 | 0.91 |
| cg10235355 | 17 | PITPNM3 | 10.07 | 22.08 | 0.46 | 6.57834E−20 | 0.75 | 0.59 | 0.91 |
| cg01364478 | 1 | PRRX1 | 8.97 | 18.25 | 0.49 | 4.31121E−14 | 0.75 | 0.59 | 0.91 |

TABLE 2-continued

Differentially methylated 412 genes with Target ID, Gene ID, chromosome location, % methylation change (compared to controls), and FDR p-value for each gene identified in the analysis

| TargetID | CHR | Gene ID | % Methylation Cases | % Methylation Control | Fold change | FDR p-Val | AUC | CI_lower | CI_upper |
|---|---|---|---|---|---|---|---|---|---|
| cg19239041 | 20 | RASSF2 | 7.22 | 20.38 | 0.35 | 1.0008E−26 | 0.75 | 0.59 | 0.91 |
| cg15480817 | 5 | TMEM171 | 3.67 | 13.63 | 0.27 | 1.70455E−22 | 0.75 | 0.59 | 0.91 |
| cg14426999 | 20 | TOX2 | 2.61 | 6.46 | 0.40 | 5.11798E−06 | 0.75 | 0.59 | 0.91 |
| cg24107270 | 7 | WDR86 | 9.85 | 24.07 | 0.41 | 3.49563E−26 | 0.75 | 0.59 | 0.91 |
| ch.15.814613R | 15 | MYO1E | 3.01 | 6.59 | 0.46 | 3.25211E−05 | 0.75 | 0.59 | 0.91 |
| cg13655635 | 9 | NR4A3 | 7.33 | 23.11 | 0.32 | 3.57028E−31 | 0.75 | 0.59 | 0.91 |
| cg07529534 | 8 | ANK1 | 1.70 | 3.40 | 0.50 | 0.034049193 | 0.75 | 0.58 | 0.91 |
| cg08024887 | 11 | CCDC88B | 4.34 | 18.33 | 0.24 | 1.19111E−31 | 0.75 | 0.58 | 0.91 |
| cg16862641 | 6 | COL9A1 | 2.44 | 5.07 | 0.48 | 0.001453983 | 0.75 | 0.58 | 0.91 |
| cg27003782 | 10 | CPXM2 | 4.61 | 11.14 | 0.41 | 4.41099E−11 | 0.75 | 0.58 | 0.91 |
| cg16373526 | 11 | CTTN | 11.92 | 28.48 | 0.42 | 2.58821E−30 | 0.75 | 0.58 | 0.91 |
| cg10788355 | 13 | ELF1 | 6.84 | 14.62 | 0.47 | 2.93979E−12 | 0.75 | 0.58 | 0.91 |
| cg22796507 | 1 | FOXE3 | 3.93 | 10.70 | 0.37 | 2.26228E−12 | 0.75 | 0.58 | 0.91 |
| cg08159065 | 5 | GABRB2 | 9.05 | 18.68 | 0.48 | 7.60104E−15 | 0.75 | 0.58 | 0.91 |
| cg25781595 | 19 | GRIN2D | 7.87 | 16.93 | 0.46 | 1.76271E−14 | 0.75 | 0.58 | 0.91 |
| cg02326386 | 19 | MOBKL2A | 6.86 | 22.46 | 0.31 | 3.20421E−31 | 0.75 | 0.58 | 0.91 |
| cg04961466 | 4 | NPY5R | 5.62 | 15.55 | 0.36 | 2.33102E−19 | 0.75 | 0.58 | 0.91 |
| cg17480467 | 10 | PAX2 | 4.16 | 10.60 | 0.39 | 2.77998E−11 | 0.75 | 0.58 | 0.91 |
| cg17336584 | 6 | PHACTR1 | 4.47 | 10.28 | 0.44 | 2.12568E−09 | 0.75 | 0.58 | 0.91 |
| cg26723002 | 8 | PLAG1; CHCHD7 | 6.41 | 15.26 | 0.42 | 2.24233E−15 | 0.75 | 0.58 | 0.91 |
| cg15978357 | 4 | RHOH | 3.07 | 14.33 | 0.21 | 4.12129E−28 | 0.75 | 0.58 | 0.91 |
| cg04228935 | 21 | RUNX1 | 3.95 | 13.03 | 0.30 | 3.5543E−19 | 0.75 | 0.58 | 0.91 |
| cg03055966 | 11 | SBF2 | 6.11 | 14.76 | 0.41 | 3.77574E−15 | 0.75 | 0.58 | 0.91 |
| cg13221285 | 2 | SH3RF3 | 12.95 | 29.35 | 0.44 | 1.11974E−28 | 0.75 | 0.58 | 0.91 |
| cg12795959 | 20 | SIRPB1 | 4.79 | 14.79 | 0.32 | 8.73007E−21 | 0.75 | 0.58 | 0.91 |
| cg02737619 | 1 | SKI | 3.40 | 10.92 | 0.31 | 4.04536E−15 | 0.75 | 0.58 | 0.91 |
| cg20956278 | 22 | SLC16A8 | 4.68 | 10.76 | 0.44 | 6.81788E−10 | 0.75 | 0.58 | 0.91 |
| cg23192776 | 21 | TIAM1 | 3.27 | 15.62 | 0.21 | 1.64984E−31 | 0.75 | 0.58 | 0.91 |
| cg26309194 | 21 | TMPRSS2 | 8.37 | 17.15 | 0.49 | 2.30126E−13 | 0.75 | 0.58 | 0.91 |
| cg09158314 | 13 | TNFSF13B | 4.91 | 11.23 | 0.44 | 2.66146E−10 | 0.75 | 0.58 | 0.91 |
| cg23724711 | 12 | WIBG | 5.94 | 17.03 | 0.35 | 2.09182E−22 | 0.75 | 0.58 | 0.91 |
| cg02017282 | 17 | WNT3 | 6.25 | 14.00 | 0.45 | 1.10829E−12 | 0.75 | 0.58 | 0.91 |
| cg00622863 | 9 | PRPF4; CDC26 | 1.66 | 4.73 | 0.35 | 8.7017E−05 | 0.75 | 0.58 | 0.91 |

SUPPLEMENTARY TABLE S1

Differentially Methylated microRNAs in mTBI.

| TargetID | CHR | microRNA ID | FDR p-Val | Fold chance | % Methylation Cases | % Methylation Control | AUC | CI_lower | CI_upper |
|---|---|---|---|---|---|---|---|---|---|
| cg08528170 | 19 | MIR24-2 | 7.36464E−14 | 0.412 | 5.568 | 13.530 | 0.843 | 0.711 | 0.975 |
| cg11432250 | 13 | MIR548AS | 9.38502E−17 | 0.484 | 10.114 | 20.893 | 0.824 | 0.685 | 0.963 |
| cg09918657 | 16 | MIR193B | 8.42165E−16 | 0.399 | 5.834 | 14.610 | 0.809 | 0.664 | 0.953 |
| cg04293733 | 1 | MIR137 | 1.02473E−07 | 0.350 | 2.427 | 6.925 | 0.802 | 0.656 | 0.949 |
| cg22388260 | 16 | MIR365-1 | 3.81667E−31 | 0.273 | 5.969 | 21.855 | 0.787 | 0.636 | 0.938 |
| cg08528170 | 19 | MIR23A | 7.36464E−14 | 0.412 | 5.568 | 13.530 | 0.843 | 0.711 | 0.975 |
| cg08528170 | 19 | MIR27A | 7.36464E−14 | 0.412 | 5.568 | 13.530 | 0.843 | 0.711 | 0.975 |

SUPPLEMENTARY TABLE S2

Differentially Methylated 12 ORF genes.

| TargetID | CHR | ORF | FDR p-Val | Fold chance | % Methylation Cases | % Methylation Control | AUC | CI_lower | CI_upper |
|---|---|---|---|---|---|---|---|---|---|
| cg11252953 | 17 | C17orf101 | 4.75647E−31 | 0.320 | 7.660 | 23.911 | 0.747 | 0.585 | 0.909 |
| cg03081691 | 1 | C1orf55 | 8.99759E−32 | 0.271 | 5.036 | 18.579 | 0.864 | 0.741 | 0.987 |
| cg27166718 | 6 | C6orf204 | 1.2683E−28 | 0.422 | 11.581 | 27.410 | 0.784 | 0.632 | 0.936 |
| cg11337945 | 5 | C5orf38 | 3.85929E−09 | 0.436 | 4.378 | 10.047 | 0.778 | 0.624 | 0.931 |
| cg10883375 | 14 | C14orf43 | 1.58015E−30 | 0.311 | 6.265 | 20.145 | 0.775 | 0.620 | 0.929 |
| cg10050900 | 1 | C1orf200 | 1.6683E−14 | 0.402 | 5.486 | 13.653 | 0.765 | 0.608 | 0.923 |
| cg03846926 | 10 | C10orf40 | 1.48757E−05 | 0.439 | 2.910 | 6.623 | 0.759 | 0.600 | 0.918 |
| cg14826711 | 1 | C1orf114 | 2.3089E−16 | 0.366 | 4.958 | 13.563 | 0.756 | 0.597 | 0.916 |
| cg21542248 | 14 | C14orf23 | 4.07572E−09 | 0.331 | 2.503 | 7.561 | 0.756 | 0.597 | 0.916 |
| cg06499647 | 2 | C2orf40 | 9.50633E−06 | 0.472 | 3.536 | 7.489 | 0.750 | 0.589 | 0.911 |

SUPPLEMENTARY TABLE S2-continued

Differentially Methylated 12 ORF genes.

| TargetID | CHR | ORF | FDR p-Val | Fold chance | % Methylation Cases | % Methylation Control | AUC | CI_lower | CI_upper |
|---|---|---|---|---|---|---|---|---|---|
| cg12860686 | 5 | C5orf38 | 2.48351E−18 | 0.335 | 4.590 | 13.694 | 0.775 | 0.620 | 0.929 |
| cg14025053 | 8 | C8orf56 | 5.28266E−18 | 0.385 | 6.025 | 15.664 | 0.750 | 0.589 | 0.911 |

SUPPLEMENTARY TABLE S3

Differentially Methylated 18 LOC genes.

| TargetID | CHR | LOC Genes | FDR p-Val | Fold chance | % Methylation Cases | % Methylation Control | AUC | CI_lower | CI_upper |
|---|---|---|---|---|---|---|---|---|---|
| cg24956533 | 15 | LOC145845 | 3.14447E−29 | 0.475 | 16.051 | 33.762 | 0.877 | 0.759 | 0.994 |
| cg14536682 | 3 | LOC339862 | 4.77947E−30 | 0.457 | 14.799 | 32.383 | 0.753 | 0.593 | 0.913 |
| cg23307878 | 10 | LOC105376360 | 1.31813E−30 | 0.450 | 14.710 | 32.683 | 0.765 | 0.608 | 0.923 |
| cg12608247 | 2 | LOC643387 | 2.14417E−14 | 0.478 | 8.447 | 17.678 | 0.765 | 0.608 | 0.923 |
| cg12608247 | 2 | LOC151174 | 2.14417E−14 | 0.478 | 8.447 | 17.678 | 0.765 | 0.608 | 0.923 |
| cg24662666 | 10 | LOC282997 | 3.46333E−31 | 0.325 | 7.573 | 23.298 | 0.787 | 0.636 | 0.938 |
| cg24603047 | 2 | LOC101927156 | 8.26506E−31 | 0.279 | 6.652 | 23.830 | 0.818 | 0.677 | 0.959 |
| cg05908371 | 20 | LOC284798 | 4.12897E−14 | 0.439 | 6.617 | 15.071 | 0.784 | 0.632 | 0.936 |
| cg07044757 | 15 | LOC145845 | 3.68152E−17 | 0.401 | 6.325 | 15.794 | 0.855 | 0.728 | 0.982 |
| cg00037681 | 12 | LOC100233209 | 1.07984E−30 | 0.253 | 5.962 | 23.595 | 0.772 | 0.616 | 0.927 |
| cg20585676 | 2 | LOC100132215 | 1.29385E−25 | 0.326 | 5.862 | 17.966 | 0.756 | 0.597 | 0.916 |
| cg12309653 | 15 | LOC145845 | 2.25346E−31 | 0.280 | 5.848 | 20.868 | 0.784 | 0.632 | 0.936 |
| cg26668608 | 2 | LOC440839 | 4.29128E−31 | 0.250 | 5.355 | 21.435 | 0.778 | 0.624 | 0.931 |
| cg11860632 | 1 | LOC100506022 | 5.40048E−31 | 0.224 | 4.754 | 21.216 | 0.753 | 0.593 | 0.913 |
| cg00764796 | 16 | LOC100134368 | 1.92945E−15 | 0.362 | 4.625 | 12.771 | 0.762 | 0.604 | 0.920 |
| cg23543318 | 4 | LOC100130872 | 3.86033E−31 | 0.260 | 4.602 | 17.691 | 0.762 | 0.604 | 0.920 |
| cg11724135 | 20 | LOC284798 | 2.36872E−19 | 0.314 | 4.239 | 13.508 | 0.765 | 0.608 | 0.923 |
| cg12393318 | 5 | LOC645323 | 3.8141E−22 | 0.275 | 3.750 | 13.644 | 0.806 | 0.660 | 0.951 |

TABLE 3

Metabolomics Results.

| Name | Mean (SD) of 0 | Mean (SD) of 1 | p-value | q-value (FDR) | Fold Change 0/1 | | p.value.origin |
|---|---|---|---|---|---|---|---|
| C0 | 35.280 (8.181) | 37.300 (10.120) | 0.8901 | 0.9129 | −1.01 | Down | 0.89015 |
| C10 | 0.171 (0.096) | 0.195 (0.084) | 0.2862 (W) | 0.7245 | −1.1 | Down | 0.28615 |
| C101 | 0.365 (0.091) | 0.341 (0.041) | 0.1335 | 0.7614 | 1.11 | Up | 0.13352 |
| C102 | 0.034 (0.011) | 0.034 (0.007) | 0.9563 (W) | 0.9129 | 1.04 | Up | 0.95633 |
| C12 | 0.083 (0.036) | 0.098 (0.042) | 0.2705 | 0.7245 | −1.15 | Down | 0.27049 |
| C12—DC | 0.049 (0.004) | 0.048 (0.003) | 0.3384 | 0.8593 | 1.06 | Up | 0.33839 |
| C121 | 0.293 (0.064) | 0.299 (0.039) | 0.8011 (W) | 0.9248 | 1.02 | Up | 0.80109 |
| C14 | 0.033 (0.013) | 0.036 (0.015) | 0.7014 (W) | 0.9129 | −1.09 | Down | 0.70135 |
| C141 | 0.085 (0.024) | 0.093 (0.033) | 0.5326 | 0.9129 | −1.06 | Down | 0.53262 |
| C141—OH | 0.011 (0.004) | 0.012 (0.005) | 0.5082 | 0.9129 | −1.08 | Down | 0.50821 |
| C142 | 0.034 (0.025) | 0.035 (0.022) | 0.6532 (W) | 0.9129 | −1.02 | Down | 0.6532 |
| C142—OH | 0.006 (0.003) | 0.006 (0.002) | 0.8351 (W) | 0.9129 | −1.05 | Down | 0.83514 |
| C16 | 0.087 (0.025) | 0.099 (0.034) | 0.5612 (W) | 0.9129 | −1.09 | Down | 0.56116 |
| C16—OH | 0.005 (0.001) | 0.005 (0.003) | 0.6637 | 0.9746 | −1.07 | Down | 0.66367 |
| C161 | 0.018 (0.010) | 0.021 (0.012) | 0.6532 (W) | 0.9129 | −1.14 | Down | 0.6532 |
| C161—OH | 0.009 (0.003) | 0.011 (0.006) | 0.6532 (W) | 0.9129 | −1.19 | Down | 0.6532 |
| C162 | 0.009 (0.004) | 0.010 (0.004) | 0.9563 (W) | 0.9511 | 1 | Up | 0.95633 |
| C162—OH | 0.013 (0.002) | 0.013 (0.002) | 0.4103 (W) | 0.9746 | 1.03 | Up | 0.41032 |
| C18 | 0.033 (0.010) | 0.041 (0.030) | 0.7341 (W) | 0.9746 | −1.22 | Down | 0.73413 |
| C181 | 0.079 (0.030) | 0.086 (0.036) | 0.7341 (W) | 0.9189 | −1.04 | Down | 0.73413 |
| C181—OH | 0.006 (0.003) | 0.007 (0.007) | 0.5612 (W) | 0.9453 | −1.25 | Down | 0.56116 |
| C182 | 0.045 (0.024) | 0.040 (0.015) | 0.7507 (W) | 0.9262 | 1.18 | Up | 0.75071 |
| C2 | 5.758 (3.916) | 6.891 (3.873) | 0.2666 (W) | 0.7245 | −1.18 | Down | 0.26658 |
| C3 | 0.453 (0.154) | 0.409 (0.163) | 0.2453 | 0.9129 | 1.17 | Up | 0.24527 |
| C3—OH | 0.007 (0.002) | 0.007 (0.003) | 0.7461 | 0.9074 | −1.04 | Down | 0.74606 |
| C31 | 0.010 (0.004) | 0.009 (0.003) | 0.1547 (W) | 0.9129 | 1.17 | Up | 0.15473 |
| C4 | 0.222 (0.161) | 0.157 (0.052) | 0.2302 (W) | 0.9129 | 1.46 | Up | 0.2302 |
| C3—DC C4—OH | 0.044 (0.040) | 0.052 (0.055) | 0.9563 (W) | 0.9746 | −1.17 | Down | 0.95633 |
| C41 | 0.014 (0.005) | 0.013 (0.003) | 0.1247 (W) | 0.7614 | 1.11 | Up | 0.12474 |
| C5 | 0.149 (0.047) | 0.147 (0.078) | 0.2666 (W) | 0.9129 | 1.1 | Up | 0.26658 |
| C5—M—DC | 0.014 (0.005) | 0.016 (0.003) | 0.4489 (W) | 0.7614 | −1.07 | Down | 0.44894 |
| C5—OH C3—DC—M | 0.029 (0.009) | 0.027 (0.006) | 0.3979 (W) | 0.9129 | 1.15 | Up | 0.39789 |

TABLE 3-continued

Metabolomics Results.

| Name | Mean (SD) of 0 | Mean (SD) of 1 | p-value | q-value (FDR) | Fold Change | 0/1 | p.value.origin |
|---|---|---|---|---|---|---|---|
| C51 | 0.015 (0.004) | 0.015 (0.007) | 0.8695 (W) | 0.9987 | 1.08 | Up | 0.86951 |
| C51—DC | 0.008 (0.004) | 0.009 (0.004) | 0.8579 | 0.9189 | −1.02 | Down | 0.85793 |
| C6 C41—DC | 0.048 (0.019) | 0.050 (0.013) | 0.7448 | 0.9129 | −1.04 | Down | 0.74479 |
| C5—DC C6—OH | 0.014 (0.006) | 0.014 (0.005) | 0.7014 (W) | 0.9831 | 1.03 | Up | 0.70135 |
| C61 | 0.012 (0.003) | 0.011 (0.003) | 0.3172 (W) | 0.9982 | 1.06 | Up | 0.31725 |
| C7—DC | 0.023 (0.013) | 0.031 (0.015) | 0.0641 (W) | 0.7245 | −1.33 | Down | 0.06408 |
| C8 | 0.113 (0.045) | 0.126 (0.038) | 0.3619 (W) | 0.7245 | −1.06 | Down | 0.36195 |
| C9 | 0.017 (0.005) | 0.017 (0.006) | 0.7144 | 0.9829 | 1.04 | Up | 0.71444 |
| lysoPC a C140 | 2.798 (0.555) | 2.871 (0.961) | 0.3737 (W) | 0.9189 | 1.02 | Up | 0.3737 |
| lysoPC a C160 | 74.220 (27.205) | 76.882 (54.845) | 0.2571 (W) | 0.9129 | 1 | Up | 0.25714 |
| lysoPC a C161 | 1.842 (0.804) | 2.099 (1.918) | 0.5034 (W) | 0.9792 | −1.08 | Down | 0.50343 |
| lysoPC a C170 | 1.298 (0.574) | 1.550 (1.076) | 0.8181 (W) | 0.9511 | −1.15 | Down | 0.81808 |
| lysoPC a C180 | 23.206 (8.058) | 22.434 (14.789) | 0.1247 (W) | 0.7245 | 1.07 | Up | 0.12474 |
| lysoPC a C181 | 13.246 (5.032) | 13.999 (8.181) | 0.6532 (W) | 0.9746 | −1.02 | Down | 0.6532 |
| lysoPC a C182 | 31.394 (15.117) | 25.829 (9.775) | 0.1213 | 0.7245 | 1.26 | Up | 0.12132 |
| lysoPC a C203 | 1.630 (0.795) | 1.681 (1.146) | 0.7177 (W) | 0.9982 | 1.03 | Up | 0.71768 |
| lysoPC a C204 | 4.642 (1.905) | 4.579 (1.792) | 0.6374 (W) | 0.9831 | 1.05 | Up | 0.63744 |
| lysoPC a C240 | 0.109 (0.024) | 0.107 (0.020) | 0.8011 (W) | 0.9746 | 1.07 | Up | 0.80109 |
| lysoPC a C260 | 0.133 (0.040) | 0.128 (0.033) | 0.7014 (W) | 0.9453 | 1.12 | Up | 0.70135 |
| lysoPC a C261 | 0.057 (0.014) | 0.058 (0.013) | 0.7073 | 0.9746 | 1.03 | Up | 0.70729 |
| lysoPC a C280 | 0.142 (0.035) | 0.132 (0.023) | 0.3857 (W) | 0.9129 | 1.15 | Up | 0.38568 |
| lysoPC a C281 | 0.146 (0.045) | 0.148 (0.029) | 0.6532 (W) | 0.9129 | 1.05 | Up | 0.6532 |
| PC aa C240 | 0.091 (0.026) | 0.078 (0.019) | 0.0994 (W) | 0.7245 | 1.22 | Up | 0.0994 |
| PC aa C260 | 0.645 (0.076) | 0.606 (0.061) | 0.045 | 0.7245 | 1.11 | Up | 0.05505 |
| PC aa C281 | 1.605 (0.527) | 1.554 (0.490) | 0.3391 (W) | 0.9129 | 1.09 | Up | 0.33914 |
| PC aa C300 | 2.328 (0.902) | 2.281 (0.667) | 0.4203 | 0.9453 | 1.08 | Up | 0.42028 |
| PC aa C320 | 11.359 (2.299) | 12.204 (2.842) | 0.5553 | 0.8301 | −1.04 | Down | 0.5553 |
| PC aa C321 | 7.265 (5.627) | 6.839 (3.743) | 0.9738 (W) | 0.9511 | 1.13 | Up | 0.97379 |
| PC aa C322 | 2.464 (1.414) | 2.092 (0.778) | 0.0427 | 0.8116 | 1.26 | Up | 0.09271 |
| PC aa C323 | 0.264 (0.065) | 0.262 (0.063) | 0.7177 (W) | 0.9829 | 1.05 | Up | 0.71768 |
| PC aa C341 | 142.817 (46.079) | 152.600 (48.488) | 0.7867 | 0.9129 | −1.03 | Down | 0.78673 |
| PC aa C342 | 385.200 (67.808) | 354.294 (51.684) | 0.0484 | 0.7245 | 1.12 | Up | 0.05837 |
| PC aa C343 | 6.376 (2.404) | 5.949 (1.490) | 0.2032 | 0.9129 | 1.13 | Up | 0.20323 |
| PC aa C344 | 0.725 (0.364) | 0.669 (0.196) | 0.2557 | 0.9189 | 1.14 | Up | 0.25568 |
| PC aa C360 | 2.943 (0.883) | 2.840 (0.771) | 0.433 | 0.9129 | 1.09 | Up | 0.43296 |
| PC aa C361 | 29.867 (9.379) | 29.682 (12.012) | 0.5176 (W) | 0.9189 | 1.05 | Up | 0.51757 |
| PC aa C362 | 233.697 (64.646) | 198.588 (46.993) | 0.0267 | 0.7245 | 1.22 | Up | 0.02665 |
| PC aa C363 | 91.330 (28.542) | 87.335 (23.025) | 0.3495 | 0.9829 | 1.09 | Up | 0.34947 |
| PC aa C364 | 143.720 (38.415) | 140.759 (34.059) | 0.5596 | 0.9745 | 1.05 | Up | 0.5596 |
| PC aa C365 | 4.723 (2.940) | 4.967 (2.387) | 0.7014 (W) | 0.9189 | −1.01 | Down | 0.70135 |
| PC aa C366 | 0.210 (0.115) | 0.200 (0.076) | 0.7842 (W) | 1 | 1.12 | Up | 0.78419 |
| PC aa C380 | 1.972 (0.642) | 2.074 (0.619) | 0.4489 (W) | 0.9129 | −1 | Down | 0.44894 |
| PC aa C383 | 38.973 (14.699) | 37.900 (12.591) | 0.8523 (W) | 0.9746 | 1.09 | Up | 0.85229 |
| PC aa C384 | 94.383 (27.573) | 94.335 (27.926) | 0.7379 | 0.9562 | 1.03 | Up | 0.73789 |
| PC aa C385 | 24.430 (7.747) | 27.212 (7.970) | 0.4939 | 0.7245 | −1.07 | Down | 0.4939 |
| PC aa C386 | 42.193 (12.534) | 43.606 (15.396) | 0.9409 | 0.9829 | 1.01 | Up | 0.94091 |
| PC aa C401 | 0.282 (0.064) | 0.268 (0.048) | 0.6218 (W) | 0.9129 | 1.1 | Up | 0.62185 |
| PC aa C402 | 0.243 (0.074) | 0.243 (0.082) | 0.7341 (W) | 0.9189 | 1.04 | Up | 0.73413 |
| PC aa C403 | 0.357 (0.085) | 0.381 (0.083) | 0.8028 | 0.9129 | −1.02 | Down | 0.80279 |
| PC aa C404 | 4.444 (1.614) | 4.581 (1.756) | 0.9563 (W) | 0.9189 | 1.02 | Up | 0.95633 |
| PC aa C405 | 6.391 (2.411) | 6.812 (2.560) | 0.5761 (W) | 0.9129 | −1.02 | Down | 0.57607 |
| PC aa C406 | 17.207 (6.186) | 16.210 (6.170) | 0.5464 (W) | 0.9129 | 1.11 | Up | 0.54644 |
| PC aa C420 | 0.486 (0.155) | 0.525 (0.121) | 0.2302 (W) | 0.7245 | −1.04 | Down | 0.2302 |
| PC aa C421 | 0.232 (0.079) | 0.252 (0.058) | 0.2390 (W) | 0.7245 | −1.05 | Down | 0.23895 |
| PC aa C422 | 0.165 (0.046) | 0.172 (0.034) | 0.6691 (W) | 0.9189 | 1.01 | Up | 0.6691 |
| PC aa C424 | 0.180 (0.036) | 0.201 (0.051) | 0.4213 | 0.7245 | −1.07 | Down | 0.42132 |
| PC aa C425 | 0.202 (0.056) | 0.226 (0.066) | 0.2479 (W) | 0.7245 | −1.07 | Down | 0.24793 |
| PC aa C426 | 0.294 (0.074) | 0.340 (0.087) | 0.274 | 0.7245 | −1.11 | Down | 0.27401 |
| PC ae C300 | 0.256 (0.069) | 0.274 (0.094) | 0.8868 (W) | 0.9189 | −1 | Down | 0.88678 |
| PC ae C301 | 0.006 (0.018) | 0.002 (0.004) | 0.6852 (W) | 0.9189 | 3.72 | Up | 0.68516 |
| PC ae C302 | 0.051 (0.011) | 0.050 (0.013) | 0.4358 (W) | 0.9129 | 1.09 | Up | 0.43585 |
| PC ae C321 | 1.888 (0.387) | 2.071 (0.446) | 0.6532 (W) | 0.828 | −1.04 | Down | 0.6532 |
| PC ae C322 | 0.412 (0.085) | 0.443 (0.115) | 0.9215 (W) | 0.9129 | −1.02 | Down | 0.92148 |
| PC ae C340 | 1.158 (0.413) | 1.361 (0.494) | 0.2134 (W) | 0.7245 | −1.13 | Down | 0.21336 |
| PC ae C341 | 6.838 (1.733) | 7.685 (2.408) | 0.4364 | 0.9074 | −1.07 | Down | 0.43642 |
| PC ae C342 | 9.013 (2.529) | 9.212 (2.840) | 0.7341 (W) | 0.9746 | 1.03 | Up | 0.73413 |
| PC ae C343 | 6.554 (2.061) | 6.909 (1.932) | 0.9563 | 0.9189 | −1.01 | Down | 0.95631 |
| PC ae C360 | 0.468 (0.081) | 0.489 (0.112) | 0.9271 | 0.9189 | −1.01 | Down | 0.92713 |
| PC ae C361 | 13.453 (4.681) | 15.581 (5.774) | 0.2134 (W) | 0.7245 | −1.1 | Down | 0.21336 |
| PC ae C362 | 12.136 (3.814) | 12.836 (4.462) | 0.9586 | 0.9189 | −1 | Down | 0.95859 |
| PC ae C363 | 5.191 (1.378) | 5.453 (1.593) | 0.9507 | 0.9189 | 1.01 | Up | 0.95071 |
| PC ae C364 | 13.570 (2.901) | 14.298 (2.850) | 0.9065 | 0.9129 | −1.01 | Down | 0.90653 |
| PC ae C365 | 7.690 (1.873) | 8.233 (1.490) | 0.7423 | 0.879 | −1.03 | Down | 0.74228 |
| PC ae C380 | 0.655 (0.243) | 0.677 (0.227) | 0.7842 (W) | 0.9745 | 1.02 | Up | 0.78419 |
| PC ae C382 | 1.181 (0.555) | 0.894 (0.426) | 0.0221 (W) | 0.7245 | 1.37 | Up | 0.02213 |

TABLE 3-continued

Metabolomics Results.

| Name | Mean (SD) of 0 | Mean (SD) of 1 | p-value | q-value (FDR) | Fold Change | 0/1 | p.value.origin |
|---|---|---|---|---|---|---|---|
| PC ae C383 | 4.999 (1.851) | 5.779 (1.971) | 0.1422 (W) | 0.7245 | −1.09 | Down | 0.14215 |
| PC ae C384 | 9.813 (2.634) | 11.356 (2.870) | 0.0405 (W) | 0.7245 | −1.11 | Down | 0.09047 |
| PC ae C385 | 11.105 (1.914) | 12.041 (2.232) | 0.5887 | 0.8622 | −1.04 | Down | 0.58867 |
| PC ae C386 | 3.256 (0.824) | 3.437 (0.845) | 0.5176 (W) | 0.9129 | −1.01 | Down | 0.51757 |
| PC ae C401 | 0.997 (0.332) | 0.984 (0.273) | 0.6704 | 0.9829 | 1.05 | Up | 0.6704 |
| PC ae C402 | 1.226 (0.296) | 1.338 (0.478) | 0.6713 | 0.9129 | −1.04 | Down | 0.67132 |
| PC ae C403 | 1.273 (0.276) | 1.422 (0.367) | 0.4532 | 0.7245 | −1.06 | Down | 0.45323 |
| PC ae C404 | 1.972 (0.415) | 2.288 (0.539) | 0.1536 | 0.7245 | −1.11 | Down | 0.15364 |
| PC ae C405 | 3.228 (0.619) | 3.708 (0.900) | 0.1904 | 0.7245 | −1.1 | Down | 0.19036 |
| PC ae C406 | 2.726 (0.746) | 3.147 (0.919) | 0.2743 | 0.7245 | −1.1 | Down | 0.27431 |
| PC ae C420 | 0.735 (0.096) | 0.772 (0.092) | 0.8673 | 0.7245 | −1.01 | Down | 0.86732 |
| PC ae C421 | 0.355 (0.077) | 0.396 (0.100) | 0.4189 | 0.7245 | −1.07 | Down | 0.41893 |
| PC ae C422 | 0.373 (0.075) | 0.416 (0.114) | 0.4417 | 0.7245 | −1.06 | Down | 0.44174 |
| PC ae C423 | 0.636 (0.133) | 0.708 (0.189) | 0.4328 | 0.7245 | −1.06 | Down | 0.43281 |
| PC ae C424 | 0.745 (0.142) | 0.830 (0.239) | 0.4521 | 0.7398 | −1.06 | Down | 0.45205 |
| PC ae C425 | 1.676 (0.294) | 1.898 (0.406) | 0.2091 | 0.7245 | −1.09 | Down | 0.20914 |
| PC ae C443 | 0.097 (0.014) | 0.110 (0.025) | 0.2863 | 0.7245 | −1.07 | Down | 0.28632 |
| PC ae C444 | 0.287 (0.045) | 0.341 (0.109) | 0.2053 (W) | 0.7245 | −1.13 | Down | 0.20528 |
| PC ae C445 | 1.181 (0.264) | 1.352 (0.372) | 0.2571 (W) | 0.7245 | −1.09 | Down | 0.25714 |
| PC ae C446 | 0.968 (0.306) | 1.014 (0.215) | 0.3857 (W) | 0.9189 | −1.01 | Down | 0.38568 |
| SM OH C141 | 4.490 (1.402) | 4.811 (1.696) | 0.8868 (W) | 0.9189 | −1.02 | Down | 0.88678 |
| SM OH C161 | 2.891 (0.762) | 3.179 (1.219) | 0.7507 (W) | 0.9511 | −1.05 | Down | 0.75071 |
| SM OH C221 | 11.656 (3.594) | 12.166 (4.092) | 0.9041 (W) | 0.9453 | −1 | Down | 0.90411 |
| SM OH C222 | 8.762 (2.381) | 9.531 (2.938) | 0.6061 | 0.9129 | −1.04 | Down | 0.6061 |
| SM OH C241 | 1.046 (0.327) | 1.133 (0.415) | 0.6691 (W) | 0.9189 | −1.03 | Down | 0.6691 |
| SM C160 | 106.500 (21.081) | 111.465 (25.262) | 0.8846 | 0.9129 | −1.01 | Down | 0.88462 |
| SM C161 | 15.843 (3.016) | 15.894 (3.646) | 0.5988 | 0.9745 | 1.04 | Up | 0.59877 |
| SM C180 | 18.380 (4.183) | 18.462 (6.535) | 0.6852 (W) | 0.9189 | 1.03 | Up | 0.68516 |
| SM C181 | 10.944 (2.185) | 11.138 (3.700) | 0.7989 | 0.9189 | 1.02 | Up | 0.7989 |
| SM C202 | 0.413 (0.095) | 0.414 (0.103) | 0.7674 (W) | 0.9982 | 1.03 | Up | 0.7674 |
| SM C240 | 17.760 (4.551) | 18.454 (5.819) | 0.9563 (W) | 0.9746 | 1 | Up | 0.95633 |
| SM C241 | 45.860 (9.098) | 48.735 (12.026) | 0.7599 | 0.9129 | −1.02 | Down | 0.75989 |
| SM C260 | 0.124 (0.032) | 0.143 (0.052) | 0.5912 (W) | 0.7245 | −1.1 | Down | 0.59115 |
| SM C261 | 0.269 (0.061) | 0.289 (0.080) | 0.754 | 0.9129 | −1.03 | Down | 0.75399 |
| H1 | 5315.467 (1690.441) | 5522.882 (1050.247) | 0.5386 | 0.7614 | −1.03 | Down | 0.53863 |
| H1.1 | 5315.467 (1690.441) | 5522.882 (1050.247) | 0.5386 | 0.7614 | −1.03 | Down | 0.53863 |
| Alanine | 287.550 (70.919) | 298.638 (96.610) | 0.9236 | 0.9189 | 1.01 | Up | 0.92363 |
| Arginine | 27.645 (23.076) | 28.809 (26.274) | 0.9913 (W) | 0.9982 | 1.03 | Up | 0.99126 |
| Asparagine | 20.273 (10.938) | 33.126 (10.015) | 0.0021 | 0.0374 | −1.57 | Down | 0.00206 |
| Aspartic acid | 20.527 (9.413) | 21.719 (8.363) | 0.6374 (W) | 0.9129 | 1.02 | Up | 0.63744 |
| Citrulline | 26.417 (7.343) | 26.376 (5.970) | 0.7093 | 0.9982 | 1.04 | Up | 0.70934 |
| Glutamine | 445.505 (86.359) | 498.468 (95.100) | 0.313 | 0.7245 | −1.07 | Down | 0.31298 |
| Glutamic acid | 99.755 (36.716) | 93.141 (43.596) | 0.2449 | 0.9129 | 1.15 | Up | 0.24492 |
| Glycine | 141.457 (29.459) | 150.685 (28.755) | 0.7676 | 0.8673 | −1.02 | Down | 0.76763 |
| Histidine | 61.410 (26.653) | 59.035 (26.294) | 0.5612 (W) | 0.9746 | 1.05 | Up | 0.56116 |
| Isoleucine | 62.187 (18.714) | 66.182 (24.791) | 0.6691 (W) | 0.9829 | −1.02 | Down | 0.6691 |
| Leucine | 109.205 (23.924) | 118.444 (31.529) | 0.6708 | 0.828 | −1.04 | Down | 0.67084 |
| Lysine | 117.148 (38.711) | 116.418 (30.150) | 0.4726 | 0.9189 | 1.07 | Up | 0.47258 |
| Methionine | 24.807 (8.681) | 23.532 (8.243) | 0.4895 (W) | 0.9129 | 1.11 | Up | 0.4895 |
| Ornithine | 48.653 (19.369) | 42.959 (13.872) | 0.2053 (W) | 0.8593 | 1.19 | Up | 0.20528 |
| Phenylalanine | 65.265 (16.435) | 66.344 (17.001) | 0.7373 | 0.9746 | 1.03 | Up | 0.7373 |
| Proline | 171.545 (51.768) | 165.574 (61.802) | 0.4819 | 0.9453 | 1.08 | Up | 0.48193 |
| Serine | 72.725 (16.671) | 74.715 (12.075) | 0.8339 | 0.9189 | 1.02 | Up | 0.83385 |
| Threonine | 94.887 (49.068) | 103.465 (33.760) | 0.4103 (W) | 0.7245 | −1.03 | Down | 0.41032 |
| Tryptophan | 35.870 (9.353) | 35.959 (7.606) | 0.6387 | 0.9982 | 1.05 | Up | 0.63866 |
| Tyrosine | 43.460 (11.569) | 37.150 (9.233) | 0.0339 | 0.7245 | 1.21 | Up | 0.06393 |
| Valine | 207.080 (42.484) | 206.341 (55.723) | 0.5682 | 0.9982 | 1.05 | Up | 0.56825 |
| Ac-Orn | 1.169 (1.892) | 0.978 (0.867) | 0.9913 (W) | 0.9189 | 1.19 | Up | 0.99126 |
| ADMA | 0.376 (0.106) | 0.428 (0.105) | 0.1681 (W) | 0.7245 | −1.11 | Down | 0.16812 |
| alpha-AAA | 1.153 (0.187) | 1.048 (0.106) | 0.0264 | 0.7245 | 1.15 | Up | 0.0264 |
| Creatinine | 56.743 (17.846) | 56.706 (14.700) | 0.6284 | 0.9987 | 1.05 | Up | 0.6284 |
| DOPA | 0.161 (0.013) | 0.165 (0.016) | 0.8447 | 0.9189 | 1.01 | Up | 0.84468 |
| Dopamine | 0.115 (0.281) | 0.173 (0.316) | 0.3737 (W) | 0.8583 | −1.44 | Down | 0.3737 |
| Histamine | 0.068 (0.012) | 0.066 (0.015) | 0.1547 (W) | 0.7245 | 1.07 | Up | 0.15473 |
| Kynurenine | 2.194 (0.596) | 2.071 (0.336) | 0.4758 (W) | 0.9129 | 1.1 | Up | 0.47577 |
| Met-SO | 0.508 (0.404) | 0.357 (0.408) | 0.1362 (W) | 0.7245 | 1.45 | Up | 0.13616 |
| Nitro-Tyr | 0.202 (0.022) | 0.197 (0.025) | 0.308 | 0.9129 | 1.07 | Up | 0.30801 |
| Putrescine | 0.135 (0.041) | 0.120 (0.029) | 0.2763 (W) | 0.8883 | 1.16 | Up | 0.27625 |
| Sarcosine | 12.290 (2.676) | 12.996 (5.494) | 0.6691 (W) | 0.9829 | −1.02 | Down | 0.6691 |
| Serotonin | 1.232 (0.495) | 1.181 (0.490) | 0.6623 | 0.9792 | 1.05 | Up | 0.66228 |
| Spermidine | 0.277 (0.227) | 0.204 (0.040) | 0.0316 (W) | 0.7245 | 1.51 | Up | 0.03161 |
| Spermine | 1.324 (3.663) | 0.522 (0.202) | 0.1483 (W) | 0.7245 | 2.51 | Up | 0.14834 |
| t4-OH-Pro | 16.407 (7.380) | 16.120 (4.228) | 0.9389 (W) | 0.9189 | 1.05 | Up | 0.93889 |
| Taurine | 125.740 (37.343) | 124.565 (35.055) | 0.8868 (W) | 0.9746 | 1.05 | Up | 0.88678 |
| SDMA | 0.216 (0.107) | 0.248 (0.075) | 0.1613 (W) | 0.7245 | −1.13 | Down | 0.16133 |

TABLE 3-continued

Metabolomics Results.

| Name | Mean (SD) of 0 | Mean (SD) of 1 | p-value | q-value (FDR) | Fold Change | 0/1 | p.value.origin |
|---|---|---|---|---|---|---|---|
| 1-Methylhistidine | 154.667 (50.069) | 181.571 (48.374) | 0.1751 (W) | 0.7245 | −1.12 | Down | 0.17513 |
| 2-Hydroxybutyric acid | 64.977 (37.246) | 68.006 (46.699) | 0.7842 (W) | 0.9982 | −1.02 | Down | 0.78419 |
| Acetic acid | 13.997 (5.134) | 16.035 (7.507) | 0.6532 (W) | 0.9129 | −1.12 | Down | 0.6532 |
| Betaine | 41.463 (16.827) | 41.106 (14.206) | 0.5871 | 0.991 | 1.07 | Up | 0.58708 |
| Acetoacetate | 54.227 (97.636) | 85.965 (104.382) | 0.1193 (W) | 0.7245 | −1.67 | Down | 0.11932 |
| Carnitine | 25.397 (9.455) | 26.588 (7.999) | 0.8158 | 0.9189 | 1.02 | Up | 0.81585 |
| Creatine | 31.447 (22.327) | 31.682 (19.176) | 0.6532 (W) | 0.9453 | 1.07 | Up | 0.6532 |
| Dimethylamine | 1.643 (0.673) | 1.759 (0.924) | 0.9255 | 0.9189 | −1.01 | Down | 0.92547 |
| Dimethylglycine | 2.867 (1.372) | 3.000 (1.343) | 0.9631 | 0.9189 | 1.01 | Up | 0.96308 |
| Citric acid | 97.550 (33.781) | 115.165 (47.955) | 0.1804 | 0.8116 | −1.14 | Down | 0.18042 |
| Choline | 3.530 (2.397) | 2.735 (2.884) | 0.2053 (W) | 0.7245 | 1.31 | Up | 0.20528 |
| Ethanol | 21.760 (27.914) | 50.924 (73.463) | 0.1681 (W) | 0.7245 | −2.26 | Down | 0.16812 |
| D-Glucose | 3974.270 (1450.672) | 4472.647 (1317.128) | 0.0475 | 0.7614 | −1.11 | Down | 0.07499 |
| Glycerol | 238.673 (70.880) | 220.771 (64.519) | 0.5761 (W) | 0.9129 | 1.12 | Up | 0.57607 |
| Fumaric acid | 1.860 (0.662) | 1.894 (0.673) | 0.7526 | 0.9792 | 1.03 | Up | 0.75265 |
| Formate | 50.980 (25.335) | 49.029 (29.597) | 0.4489 (W) | 0.9189 | 1.07 | Up | 0.44894 |
| Hypoxanthine | 0.310 (0.339) | 0.177 (0.144) | 0.0483 (W) | 0.7245 | 1.88 | Up | 0.07827 |
| Mannose | 38.153 (25.137) | 52.635 (32.662) | 0.171 | 0.7245 | −1.26 | Down | 0.17104 |
| L-Lactic acid | 3001.200 (1571.159) | 2394.912 (1210.903) | 0.1304 (W) | 0.7614 | 1.32 | Up | 0.13036 |
| Myo-inositol | 62.160 (53.566) | 63.818 (44.875) | 0.6374 (W) | 0.9453 | 1.04 | Up | 0.63744 |
| Pyruvic acid | 92.173 (68.259) | 88.612 (49.830) | 0.7245 | 0.9746 | 1.07 | Up | 0.72453 |
| Succinate | 23.917 (8.492) | 27.588 (6.867) | 0.2453 | 0.7245 | −1.12 | Down | 0.24531 |
| Pyroglutamic acid | 51.727 (12.572) | 62.388 (14.322) | 0.046 | 0.7245 | −1.14 | Down | 0.0846 |
| Xanthine | 1.220 (0.502) | 1.300 (0.486) | 0.8931 | 0.9189 | −1.02 | Down | 0.89306 |
| Urea | 208.897 (101.155) | 204.171 (67.970) | 0.6532 (W) | 0.9453 | 1.04 | Up | 0.6532 |
| 3-Hydroxybutyric acid | 127.210 (294.130) | 204.571 (316.922) | 0.3281 (W) | 0.8593 | −1.75 | Down | 0.32807 |
| 3-Methylhistidine | 70.197 (31.398) | 60.194 (21.672) | 0.1696 | 0.8116 | 1.21 | Up | 0.16961 |
| Creatinine.1 | 36.427 (31.009) | 34.529 (12.540) | 0.5761 (W) | 0.9129 | 1.1 | Up | 0.57607 |
| Malonate | 6.987 (2.627) | 7.253 (2.473) | 0.9676 | 0.9453 | −1.01 | Down | 0.96757 |
| Hippuric acid | 3.547 (0.890) | 3.576 (1.056) | 0.6802 | 0.9829 | 1.04 | Up | 0.68025 |
| Isovaleric acid | 9.320 (6.241) | 13.424 (10.315) | 0.1613 (W) | 0.7245 | −1.41 | Down | 0.16133 |
| 3-Hydroxyisovaleric acid | 0.737 (0.697) | 0.612 (0.778) | 0.4358 (W) | 0.9129 | 1.34 | Up | 0.43585 |
| Isopropyl alcohol | 13.637 (29.294) | 3.600 (2.320) | 0.0058 (W) | 0.7245 | 3.89 | Up | 0.00579 |
| Acetone | 37.537 (73.771) | 38.776 (48.500) | 0.1304 (W) | 0.7245 | −1.1 | Down | 0.13036 |
| Isobutyric acid | 7.903 (3.819) | 7.088 (3.426) | 0.3172 (W) | 0.9129 | 1.2 | Up | 0.31725 |
| Methanol | 755.943 (289.816) | 771.694 (301.412) | 0.9738 (W) | 0.9746 | 1.02 | Up | 0.97379 |
| Propylene glycol | 0.780 (0.419) | 0.794 (0.396) | 0.9871 | 0.9829 | 1 | Up | 0.9871 |
| Dimethyl sulfone | 4.317 (2.635) | 3.871 (2.838) | 0.3619 (W) | 0.9129 | 1.13 | Up | 0.36195 |

Univariate analysis result for each metabolite.
P-value is calculated with t-test as a default.
P-value with (W) is calculated by the Wilcoxon Mann Whitney test.

TABLE 4

Results of Concussion Prediction: Epigenetic Markers only (total of 390 evaluated).

| | SVM | GLM | PAM | RF | LDA | DL |
|---|---|---|---|---|---|---|
| AUC 95% CI | 0.9433 (0.6660-1) | 0.9822 (0.8020-1) | 0.9528 (0.7950-1) | 0.9377 (0.6660-1) | 0.9889 (0.8020-1) | 0.9889 (0.8030-1) |
| SENSITIVITY | 0.9000 | 0.9500 | 0.6670 | 0.8500 | 0.8000 | 0.9500 |
| SPEC | 0.8500 | 0.9050 | 0.9000 | 0.9500 | 0.9300 | 0.9120 |

Significant predictors in descending order of accuracy for each ML approach:
SVM: cg00611535, cg20569893, cg06393885, cg24402518, cg20601481
GLM: cg05138188, cg27384352, cg24684739, cg00611535, ch.8.1136903F
PAM: cg06393885, cg13528854, cg05138188, cg20601481, cg24104241
RF: cg06393885, cg24684739, cg18419977, cg07077221, cg03957481
LDA: cg06393885, cg19470964, cg06233996, cg05138188, cg24742298
DL: cg00611535, cg05138188, cg27384352, cg15531403, cg16117781

TABLE 5

Results of Concussion Prediction with Epigenetic Markers (total of 390 evaluated) plus Clinical Characteristics.

|  | SVM | GLM | PAM | RF | LDA | DL |
|---|---|---|---|---|---|---|
| AUC 95% CI | 0.9722 (0.7737-1) | 0.9988 (0.7975-1) | 0.9988 (0.7915-1) | 0.9255 (0.7213-1) | 0.9955 (0.7728-1) | 0.9888 (0.8095-1) |
| SENSITIVITY | 0.9000 | 0.8000 | 0.6753 | 0.8000 | 0.8670 | 0.9774 |
| SPEC | 0.9500 | 0.9800 | 0.9862 | 0.9500 | 0.9333 | 0.9500 |

Significant predictors in descending order of accuracy for each ML approach:
SVM: SAC, cg07077221, cg19470964, cg06393885, cg20569893
GLM: cg05138188, cg27384352, SAC, cg00611535, cg24684739
PAM: SAC, cg20569893, cg20891481, cg06393885, cg24402518
RF: SAC, cg06393885, cg24104241, cg05138188, cg20569893
LDA: SAC, cg06393885, cg00611535, cg05138188, cg16882751
DL: SAC, cg05138188, cg24684739, cg00611535, Loss of consciousness

TABLE 6

Concussion Prediction Based on Combined Epigenetic (390 markers) Plus Metabolomics Markers.

|  | SVM | GLM | PAM | RF | LDA | DL |
|---|---|---|---|---|---|---|
| AUC 95% CI | 0.8888 (0.7660-1) | 0.9221 (0.8020-1) | 0.8016 (0.6950-1) | 0.9418 (0.7660-1) | 0.8617 (0.7020-1) | 0.9557 (0.8030-1) |
| SENSITIVITY | 0.8000 | 0.8500 | 0.7000 | 0.8500 | 0.7333 | 0.9000 |
| SPEC | 0.7500 | 0.9500 | 0.8500 | 0.9000 | 0.8000 | 0.9170 |

Significant predictors in descending order of accuracy for each ML approach:
SVM: cg00611535, cg20569893, cg06393885, cg24402518, cg05138188
GLM: C3.1, cg05138188, cg27384352, cg24684739, cg00611535, C16.2.OH
PAM: cg06393885, cg13528854, cg05138188, cg20601481, cg24104241
RF: cg06393885, cg24684739, Asparagine, cg18419977, cg07077221
LDA: cg00611535, cg20569893, cg24742298, cg06393885, cg19470964
DL: cg05138188, cg27384352, alpha.AAA, cg00611535, cg07801620

TABLE 7

Combined Epigenetic and Metabolomic Markers Plus Clinical Characteristics for Prediction of Concussion.

|  | SVM | GLM | PAM | RF | LDA | DL |
|---|---|---|---|---|---|---|
| AUC 95% CI | 0.8466 (0.6737-1) | 0.9933 (0.7975-1) | 0.9628 (0.7915-1) | 0.9222 (0.7213-1) | 0.8853 (0.7728-1) | 0.9704 (0.8095-1) |
| SENSITIVITY | 0.8000 | 0.8500 | 0.8753 | 0.8200 | 0.8670 | 0.9000 |
| SPEC | 0.9500 | 0.9800 | 0.9862 | 0.9000 | 0.9333 | 0.9500 |

Significant predictors in descending order of accuracy for each ML approach:
SVM: SAC, cg06393885, cg05138188, cg24402518, cg20569893
GLM: C3.1, cg05138188, cg27384352, cg00611535, C16.2.OH
PAM: cg07801620, cg16882751, cg00611535, cg00832555, cg24402518
RF: SAC, cg03957481, cg24684739, cg25997979, cg00611535
LDA: SAC, cg06393885, cg13528854, cg16882751, cg00611535
DL: SAC, cg05138188, cg07801620, cg16117781, cg27384352

TABLE 8

Combined Metabolomic Markers Plus Clinical Characteristics for Concussion Prediction.

|  | SVM | GLM | PAM | RF | LDA | DL |
|---|---|---|---|---|---|---|
| AUC 95% CI | 0.7430 (0.5660-0.9200) | 0.9811 (0.8020-1) | 0.9789 (0.7950-1) | 0.9911 (0.7660-1) | 0.7464 (0.5650-0.9278) | 0.9814 (0.8030-1) |
| SENSITIVITY | 0.7000 | 0.9250 | 0.9770 | 0.9500 | 0.7000 | 0.9380 |
| SPEC | 0.6000 | 0.8500 | 0.9100 | 0.9500 | 0.6000 | 0.8120 |

Significant predictors in descending order of accuracy for each ML approach:
SVM: SAC, Asparagine, PC.aa.C24.0, alpha.AAA, Isopropyl.alcohol
GLM: SAC, Loss.of.consciousness, alpha.AAA, Asparagine, lysoPC.a.C18.2
PAM: SAC, Asparagine, PC.aa.C24.0, PC.ae.C38.2, alpha.AAA
RF: SAC, Asparagine, PC.aa.C24.0, Histamine, C3
LDA: SAC, PC.aa.C24.0, Asparagine, alpha.AAA, Histamine
DL: SAC, Asparagine, alpha.AAA, PC.ae.C32.1, lysoPC.a.C18.2

SUPPLEMENTAL TABLE S4

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg10464462 | 17 | RFFL | -31.352 | 4.44216E-32 | 0.196 | -0.708 | -0.708 | 3.026 | 15.459 | 0.799 | 0.652 | 0.947 |
| cg14201424 | 4 | MGC45800 | -31.226 | 5.9388 7E-32 | 0.185 | -0.733 | -0.733 | 2.921 | 15.809 | 0.753 | 0.593 | 0.913 |
| cg08596591 | 9 | FGD3 | -31.055 | 8.80088E-32 | 0.171 | -0.768 | -0.768 | 2.781 | 16.289 | 0.759 | 0.600 | 0.918 |
| cg05767930 | 12 | RHOF | -31.006 | 9.87378E-32 | 0.196 | -0.707 | -0.707 | 3.340 | 17.031 | 0.756 | 0.597 | 0.916 |
| cg16795850 | 6 | LST1 | -30.988 | 1.02775E-31 | 0.237 | -0.625 | -0.625 | 4.281 | 18.036 | 0.815 | 0.673 | 0.957 |
| cg12798338 | 17 | TMC8; TMC6 | -30.985 | 1.03499E-31 | 0.229 | -0.640 | -0.640 | 4.093 | 17.859 | 0.778 | 0.624 | 0.931 |
| cg11852643 | 6 | TCP11 | -30.945 | 1.13579E-31 | 0.158 | -0.802 | -0.802 | 2.608 | 16.523 | 0.772 | 0.616 | 0.927 |
| cg08024887 | 11 | CCDC88B | -30.924 | 1.19111E-31 | 0.237 | -0.625 | -0.625 | 4.344 | 18.335 | 0.747 | 0.585 | 0.909 |
| cg05651417 | 7 | SNX10 | -30.881 | 1.31649E-31 | 0.301 | -0.521 | -0.521 | 6.098 | 20.249 | 0.802 | 0.656 | 0.949 |
| cg02049511 | 11 | SCT | -30.811 | 1.54523E-31 | 0.229 | -0.639 | -0.639 | 4.289 | 18.698 | 0.784 | 0.632 | 0.936 |
| cg27071460 | 5 | PTGER4 | -30.809 | 1.55329E-31 | 0.181 | -0.743 | -0.743 | 2.628 | 14.555 | 0.772 | 0.616 | 0.927 |
| cg25526061 | 10 | ADAM8 | -30.791 | 1.6176E-31 | 0.249 | -0.604 | -0.604 | 4.803 | 19.286 | 0.799 | 0.652 | 0.947 |
| cg06233996 | 18 | NEDD4L | -30.789 | 1.62449E-31 | 0.238 | -0.624 | -0.624 | 4.517 | 19.007 | 0.892 | 0.782 | 1.000 |
| cg23192776 | 21 | TIAM1 | -30.783 | 1.64984E-31 | 0.209 | -0.679 | -0.679 | 3.268 | 15.617 | 0.747 | 0.585 | 0.909 |
| cg13549444 | 12 | PTPN6 | -30.775 | 1.68008E-31 | 0.226 | -0.646 | -0.646 | 4.241 | 18.785 | 0.756 | 0.597 | 0.916 |
| cg17213699 | 12 | LAG3 | -30.690 | 2.04164E-31 | 0.225 | -0.648 | -0.648 | 4.313 | 19.172 | 0.781 | 0.628 | 0.934 |
| cg02253612 | 7 | STX1A | -30.610 | 2.45427E-31 | 0.222 | -0.653 | -0.653 | 3.575 | 16.074 | 0.787 | 0.636 | 0.938 |
| cg26720543 | 2 | INPP5D | -30.607 | 2.4696E-31 | 0.233 | -0.632 | -0.632 | 4.611 | 19.781 | 0.806 | 0.660 | 0.951 |
| cg18122874 | 22 | IL17RA | -30.586 | 2.59595E-31 | 0.283 | -0.549 | -0.549 | 6.012 | 21.264 | 0.772 | 0.616 | 0.927 |
| cg00381233 | 17 | VOPP1 | -30.578 | 2.64118E-31 | 0.347 | -0.460 | -0.460 | 7.992 | 23.053 | 0.796 | 0.648 | 0.944 |
| cg09243716 | 8 | DLC1 | -30.556 | 2.77884E-31 | 0.313 | -0.499 | -0.499 | 7.135 | 22.498 | 0.806 | 0.660 | 0.951 |
| cg26433975 | 7 | COM2 | -30.530 | 2.95218E-31 | 0.317 | -0.498 | -0.498 | 7.333 | 23.109 | 0.762 | 0.604 | 0.920 |
| cg14503399 | 8 | CPQ | -30.521 | 3.01444E-31 | 0.264 | -0.578 | -0.578 | 5.550 | 21.012 | 0.824 | 0.685 | 0.963 |
| cg02326386 | 19 | MOBKL2A | -30.494 | 3.20421E-31 | 0.287 | -0.542 | -0.542 | 6.250 | 21.747 | 0.772 | 0.604 | 0.909 |
| cg05851250 | 3 | ANO10 | -30.470 | 3.38947E-31 | 0.306 | -0.515 | -0.515 | 6.861 | 22.458 | 0.747 | 0.585 | 0.920 |
| cg13655635 | 9 | NR4A3 | -30.447 | 3.57028E-31 | 0.314 | -0.505 | -0.505 | 7.147 | 22.837 | 0.806 | 0.660 | 0.951 |
| cg07498879 | 22 | OSM | -30.420 | 3.79848E-31 | 0.230 | -0.639 | -0.639 | 4.735 | 20.613 | 0.748 | 0.587 | 0.910 |
| cg23543318 | 4 | SPON2 | -30.413 | 3.86033E-31 | 0.260 | -0.585 | -0.585 | 4.602 | 17.691 | 0.815 | 0.673 | 0.957 |
| cg25206113 | 1 | RORC | -30.408 | 3.91138E-31 | 0.314 | -0.503 | -0.503 | 7.291 | 23.217 | 0.762 | 0.604 | 0.920 |
| cg07200038 | 16 | MMP25 | -30.404 | 3.94704E-31 | 0.377 | -0.423 | -0.423 | 9.659 | 25.600 | 0.750 | 0.589 | 0.911 |
| cg24402518 | 10 | PIK3AP1 | -30.402 | 3.95878E-31 | 0.361 | -0.443 | -0.443 | 8.668 | 24.017 | 0.886 | 0.772 | 0.999 |
| cg26754426 | 3 | CD200R1 | -30.399 | 3.99339E-31 | 0.362 | -0.441 | -0.441 | 9.073 | 25.033 | 0.769 | 0.612 | 0.925 |
| cg23953831 | 1 | CD101 | -30.383 | 4.13588E-31 | 0.298 | -0.526 | -0.526 | 6.800 | 22.819 | 0.769 | 0.612 | 0.925 |
| cg26668608 | 2 | PSD4 | -30.367 | 4.29128E-31 | 0.250 | -0.602 | -0.602 | 5.355 | 21.435 | 0.778 | 0.624 | 0.931 |
| cg06086267 | 7 | CUX1 | -30.364 | 4.32444E-31 | 0.266 | -0.574 | -0.574 | 5.844 | 21.937 | 0.775 | 0.620 | 0.929 |
| cg21455600 | 7 | KCTD7 | -30.360 | 4.3641E-31 | 0.179 | -0.748 | -0.748 | 3.504 | 19.612 | 0.765 | 0.608 | 0.923 |
| cg05601847 | 1 | RCSD1 | -30.338 | 4.59305E-31 | 0.316 | -0.500 | -0.500 | 7.483 | 23.675 | 0.769 | 0.612 | 0.925 |
| cg10098353 | 2 | CD28 | -30.321 | 4.771E-31 | 0.347 | -0.460 | -0.460 | 8.642 | 24.898 | 0.769 | 0.612 | 0.925 |
| cg14999168 | 11 | PPFIA1 | -30.283 | 5.2131E-31 | 0.357 | -0.447 | -0.447 | 9.104 | 25.508 | 0.784 | 0.632 | 0.936 |
| cg26921036 | 4 | TEC | -30.262 | 5.47344E-31 | 0.321 | -0.494 | -0.494 | 7.780 | 24.266 | 0.815 | 0.673 | 0.957 |
| cg09762242 | 4 | THAP9 | -30.230 | 5.88866E-31 | 0.365 | -0.438 | -0.438 | 9.552 | 26.159 | 0.812 | 0.669 | 0.955 |
| cg09762242 | 11 | SIPA1 | -30.202 | 6.27891E-31 | 0.304 | -0.517 | -0.517 | 7.310 | 24.025 | 0.753 | 0.593 | 0.913 |
| cg18490792 | 16 | PLCG2 | -30.183 | 6.55642E-31 | 0.282 | -0.549 | -0.549 | 6.603 | 23.391 | 0.830 | 0.694 | 0.967 |
| cg04184297 | 17 | SLC16A3 | -30.179 | 6.61457E-31 | 0.139 | -0.858 | -0.858 | 2.704 | 19.507 | 0.799 | 0.652 | 0.947 |
| cg03343063 | 1 | PLEKHM2 | -30.136 | 7.31143E-31 | 0.294 | -0.532 | -0.532 | 5.687 | 19.340 | 0.843 | 0.711 | 0.975 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg12374834 | 1 | LAPTM5 | −30.122 | 7.54815E-31 | 0.303 | −0.519 | −0.519 | 7.397 | 24.422 | 0.756 | 0.597 | 0.916 |
| cg09092089 | 7 | GIMAP7 | −30.100 | 7.94332E-31 | 0.299 | −0.524 | −0.524 | 7.304 | 24.415 | 0.775 | 0.620 | 0.929 |
| cg03286855 | 7 | RAPGEF5 | −30.094 | 8.04544E-31 | 0.418 | −0.379 | −0.379 | 12.312 | 29.445 | 0.802 | 0.656 | 0.949 |
| cg18025430 | 11 | MS4A4A | −30.060 | 8.70399E-31 | 0.341 | −0.467 | −0.467 | 8.947 | 26.213 | 0.765 | 0.608 | 0.923 |
| cg04889100 | 17 | ARSG | −30.060 | 8.71941E-31 | 0.168 | −0.775 | −0.775 | 3.485 | 20.754 | 0.775 | 0.620 | 0.929 |
| cg05109049 | 17 | EVI2B; NF1 | −30.056 | 8.78206E-31 | 0.352 | −0.454 | −0.454 | 9.381 | 26.662 | 0.790 | 0.640 | 0.940 |
| cg05694921 | 1 | PTPRU | −30.055 | 8.81648E-31 | 0.362 | −0.442 | −0.442 | 9.793 | 27.081 | 0.784 | 0.632 | 0.936 |
| cg10303411 | 6 | FAM65B | −30.009 | 9.79114E-31 | 0.231 | −0.637 | −0.637 | 5.235 | 22.701 | 0.806 | 0.660 | 0.951 |
| cg00037681 | 12 | FAM113B | −29.967 | 1.07984E-30 | 0.253 | −0.597 | −0.597 | 5.962 | 23.595 | 0.772 | 0.616 | 0.927 |
| cg27210998 | 17 | GRB2 | −29.943 | 1.14086E-30 | 0.353 | −0.452 | −0.452 | 8.168 | 23.112 | 0.775 | 0.620 | 0.929 |
| cg16732780 | 5 | CDHR2 | −29.936 | 1.15971E-30 | 0.340 | −0.468 | −0.468 | 9.152 | 26.906 | 0.769 | 0.612 | 0.925 |
| cg04104119 | 5 | LNPEP | −29.920 | 1.2027E-30 | 0.370 | −0.432 | −0.432 | 10.459 | 28.275 | 0.809 | 0.664 | 0.953 |
| cg13329322 | 2 | SGPP2 | −29.912 | 1.22587E-30 | 0.413 | −0.384 | −0.384 | 12.562 | 30.411 | 0.756 | 0.597 | 0.916 |
| cg26693584 | 16 | WWOX | −29.885 | 1.30206E-30 | 0.286 | −0.544 | −0.544 | 7.177 | 25.129 | 0.790 | 0.640 | 0.940 |
| cg24742298 | 17 | SEZ6 | −29.884 | 1.3047E-30 | 0.261 | −0.583 | −0.583 | 6.357 | 24.313 | 0.892 | 0.782 | 1.000 |
| cg23413809 | 2 | SIX2 | −29.851 | 1.40809E-30 | 0.186 | −0.730 | −0.730 | 4.135 | 22.221 | 0.796 | 0.648 | 0.944 |
| cg12823387 | 1 | PTPN14 | −29.794 | 1.60559E-30 | 0.436 | −0.361 | −0.361 | 14.142 | 32.455 | 0.759 | 0.600 | 0.918 |
| cg17836354 | 22 | MKL1 | −29.773 | 1.68483E-30 | 0.263 | −0.580 | −0.580 | 6.573 | 24.968 | 0.833 | 0.698 | 0.969 |
| cg03647767 | 10 | JMJD1C | −29.755 | 1.75723E-30 | 0.274 | −0.562 | −0.562 | 6.982 | 25.451 | 0.796 | 0.648 | 0.944 |
| cg16478871 | 16 | XPO6 | −29.751 | 1.77311E-30 | 0.386 | −0.413 | −0.413 | 11.629 | 30.113 | 0.799 | 0.652 | 0.947 |
| cg01778680 | 15 | ISLR2 | −29.738 | 1.82601E-30 | 0.294 | −0.531 | −0.531 | 7.725 | 26.260 | 0.765 | 0.608 | 0.923 |
| cg02147055 | 1 | PTPRC | −29.683 | 2.07274E-30 | 0.326 | −0.486 | −0.486 | 9.091 | 27.846 | 0.765 | 0.608 | 0.923 |
| cg27531206 | 1 | UCK2 | −29.630 | 2.34644E-30 | 0.285 | −0.545 | −0.545 | 7.573 | 26.544 | 0.799 | 0.652 | 0.947 |
| cg01967102 | 3 | KAT2B | −29.613 | 2.43888E-30 | 0.433 | −0.364 | −0.364 | 14.510 | 33.548 | 0.843 | 0.711 | 0.975 |
| cg16373526 | 11 | CTTN | −29.587 | 2.58821E-30 | 0.418 | −0.378 | −0.378 | 11.915 | 28.479 | 0.747 | 0.585 | 0.909 |
| cg02093777 | 4 | HPGDS | −29.475 | 3.35181E-30 | 0.313 | −0.504 | −0.504 | 6.280 | 20.066 | 0.802 | 0.656 | 0.949 |
| cg06951565 | 5 | GRM6 | −29.414 | 3.85776E-30 | 0.375 | −0.426 | −0.426 | 9.156 | 24.417 | 0.756 | 0.597 | 0.916 |
| cg01555705 | 16 | CX3CL1 | −29.362 | 4.34559E-30 | 0.360 | −0.444 | −0.444 | 8.334 | 23.173 | 0.772 | 0.616 | 0.927 |
| cg16882751 | 1 | FCMR | −28.887 | 1.29837E-29 | 0.415 | −0.382 | −0.382 | 15.642 | 37.672 | 0.895 | 0.786 | 1.000 |
| cg21115691 | 1 | FCAMR | −28.869 | 1.35261E-29 | 0.226 | −0.646 | −0.646 | 3.486 | 15.429 | 0.855 | 0.728 | 0.982 |
| cg21720679 | 20 | RBL1 | −28.402 | 3.96069E-29 | 0.457 | −0.340 | −0.340 | 14.386 | 31.488 | 0.765 | 0.608 | 0.923 |
| cg11085070 | 9 | TTF1 | −28.301 | 5.00196E-29 | 0.375 | −0.426 | −0.426 | 8.848 | 23.586 | 0.776 | 0.622 | 0.930 |
| cg05021267 | 20 | POFUT1 | −28.296 | 5.05413E-29 | 0.431 | −0.366 | −0.366 | 12.327 | 28.605 | 0.775 | 0.620 | 0.929 |
| cg16016319 | 1 | TRIM63 | −28.211 | 6.157E-29 | 0.324 | −0.489 | −0.489 | 6.484 | 19.982 | 0.790 | 0.640 | 0.940 |
| cg22761241 | 1 | LINC01225 | −28.116 | 7.66047E-29 | 0.422 | −0.374 | −0.374 | 11.653 | 27.590 | 0.799 | 0.652 | 0.947 |
| cg13221285 | 2 | SH3RF3 | −27.951 | 1.11974E-28 | 0.441 | −0.355 | −0.355 | 12.953 | 29.355 | 0.747 | 0.585 | 0.909 |
| cg07077221 | 3 | HESRG | −27.902 | 1.252E-28 | 0.357 | −0.447 | −0.447 | 7.833 | 21.938 | 0.855 | 0.728 | 0.982 |
| cg27166718 | 6 | PLN | −27.897 | 1.2683E-28 | 0.422 | −0.374 | −0.374 | 11.581 | 27.410 | 0.784 | 0.632 | 0.936 |
| cg08288130 | 8 | DOK2 | −27.822 | 1.50612E-28 | 0.410 | −0.387 | −0.387 | 10.761 | 26.214 | 0.753 | 0.593 | 0.913 |
| cg00231338 | 12 | PLBD1 | −27.778 | 1.6683E-28 | 0.418 | −0.379 | −0.379 | 11.222 | 26.859 | 0.806 | 0.660 | 0.951 |
| cg02305095 | 2 | CUL3 | −27.760 | 1.73681E-28 | 0.450 | −0.347 | −0.347 | 13.547 | 30.107 | 0.784 | 0.632 | 0.936 |
| cg21448352 | 2 | KLHL29 | −27.606 | 2.47599E-28 | 0.419 | −0.378 | −0.378 | 11.222 | 26.798 | 0.756 | 0.597 | 0.916 |
| cg11686792 | 13 | RASA3 | −27.540 | 2.88503E-28 | 0.293 | −0.533 | −0.533 | 5.208 | 17.787 | 0.787 | 0.636 | 0.938 |
| cg04192740 | 5 | STK10 | −27.515 | 3.05439E-28 | 0.315 | −0.502 | −0.502 | 5.975 | 18.975 | 0.809 | 0.664 | 0.953 |
| cg15978357 | 4 | RHOH | −27.385 | 4.12129E-28 | 0.214 | −0.669 | −0.669 | 3.074 | 14.332 | 0.747 | 0.585 | 0.909 |
| cg24954861 | 15 | IGF1R | −27.365 | 4.31675E-28 | 0.442 | −0.355 | −0.355 | 12.744 | 28.853 | 0.830 | 0.694 | 0.967 |
| cg03656996 | 15 | PLCB2 | −27.049 | 8.93827E-28 | 0.253 | −0.596 | −0.596 | 3.974 | 15.685 | 0.775 | 0.620 | 0.929 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg06648277 | 10 | NKX6-2 | −27.006 | 9.86624E-28 | 0.244 | −0.612 | −0.612 | 3.737 | 15.294 | 0.799 | 0.652 | 0.947 |
| cg26256223 | 8 | OPLAH | −26.973 | 1.06488E-27 | 0.261 | −0.583 | −0.583 | 4.168 | 15.972 | 0.753 | 0.593 | 0.913 |
| cg12011642 | 17 | MSI2 | −26.833 | 1.46855E-27 | 0.453 | −0.344 | −0.344 | 13.345 | 29.491 | 0.765 | 0.608 | 0.923 |
| cg17078116 | 8 | NEFM | −26.655 | 2.21457E-27 | 0.279 | −0.554 | −0.554 | 4.650 | 16.640 | 0.836 | 0.702 | 0.971 |
| cg03822198 | 12 | MAP1LC3B2 | −26.653 | 2.22338E-27 | 0.226 | −0.646 | −0.646 | 3.259 | 14.423 | 0.753 | 0.593 | 0.913 |
| cg06203744 | 2 | KIAA2012 | −26.399 | 3.98819E-27 | 0.438 | −0.359 | −0.359 | 12.077 | 27.573 | 0.781 | 0.628 | 0.934 |
| cg12690996 | 1 | KLHL21 | −26.344 | 4.52576E-27 | 0.419 | −0.378 | −0.378 | 10.761 | 25.693 | 0.769 | 0.612 | 0.925 |
| cg22836191 | 8 | CHRNA6 | −26.334 | 4.63598E-27 | 0.308 | −0.511 | −0.511 | 5.513 | 17.887 | 0.830 | 0.694 | 0.967 |
| cg04385966 | 3 | KLHL6 | −26.313 | 4.86807E-27 | 0.277 | −0.557 | −0.557 | 4.537 | 16.356 | 0.821 | 0.681 | 0.961 |
| cg00983904 | 12 | IFFO1 | −26.066 | 8.58091E-27 | 0.412 | −0.385 | −0.385 | 10.227 | 24.830 | 0.790 | 0.640 | 0.940 |
| cg16117781 | 1 | TNFRSF9 | −26.033 | 9.26684E-27 | 0.489 | −0.311 | −0.311 | 16.060 | 32.847 | 0.806 | 0.660 | 0.951 |
| cg19239041 | 20 | RASSF2 | −26.000 | 1.0008E-26 | 0.354 | −0.451 | −0.451 | 7.216 | 20.381 | 0.750 | 0.589 | 0.911 |
| cg26961808 | 7 | FLNC | −25.993 | 1.01563E-26 | 0.274 | −0.562 | −0.562 | 4.402 | 16.047 | 0.775 | 0.620 | 0.929 |
| cg23141934 | 19 | SWSAP1 | −25.970 | 1.07227E-26 | 0.372 | −0.429 | −0.429 | 8.048 | 21.614 | 0.756 | 0.597 | 0.916 |
| cg13073773 | 14 | GSC | −25.929 | 1.17705E-26 | 0.257 | −0.591 | −0.591 | 3.914 | 15.257 | 0.778 | 0.624 | 0.931 |
| cg09980176 | 19 | CCDC151 | −25.740 | 1.81845E-26 | 0.356 | −0.448 | −0.448 | 7.248 | 20.343 | 0.765 | 0.608 | 0.923 |
| cg12217024 | 11 | GRIA4 | −25.634 | 2.3205E-26 | 0.265 | −0.577 | −0.577 | 4.094 | 15.454 | 0.781 | 0.628 | 0.934 |
| cg08972954 | 5 | ITK | −25.594 | 2.54951E-26 | 0.320 | −0.495 | −0.495 | 5.771 | 18.052 | 0.778 | 0.624 | 0.931 |
| cg24107270 | 7 | WDR86 | −25.456 | 3.49563E-26 | 0.409 | −0.388 | −0.388 | 9.851 | 24.074 | 0.750 | 0.589 | 0.911 |
| cg23340017 | 10 | TLX1 | −25.069 | 8.53257E-26 | 0.367 | −0.435 | −0.435 | 7.568 | 20.597 | 0.759 | 0.600 | 0.918 |
| cg10926336 | 10 | DCLRE1A | −24.961 | 1.0936E-25 | 0.474 | −0.324 | −0.324 | 14.228 | 29.994 | 0.765 | 0.608 | 0.923 |
| cg14015044 | 8 | TNFRSF10C | −24.925 | 1.18898E-25 | 0.091 | −1.043 | −1.043 | 0.916 | 10.123 | 0.753 | 0.593 | 0.913 |
| cg15665792 | 7 | ELMO1 | −24.617 | 2.4182E-25 | 0.489 | −0.311 | −0.311 | 15.320 | 31.324 | 0.818 | 0.677 | 0.959 |
| cg21340223 | 19 | LAIR1 | −24.520 | 3.02029E-25 | 0.360 | −0.444 | −0.444 | 7.076 | 19.679 | 0.778 | 0.624 | 0.931 |
| cg07223253 | 7 | GIMAP8 | −24.201 | 6.29657E-25 | 0.275 | −0.561 | −0.561 | 4.155 | 15.118 | 0.759 | 0.600 | 0.918 |
| cg17848763 | 2 | GYPC | −24.198 | 6.33248E-25 | 0.281 | −0.551 | −0.551 | 4.332 | 15.392 | 0.765 | 0.608 | 0.923 |
| cg17669121 | 12 | ATP6V0A2 | −24.173 | 6.70897E-25 | 0.493 | −0.307 | −0.307 | 15.430 | 31.298 | 0.772 | 0.616 | 0.927 |
| cg12378187 | 3 | FEZF2 | −24.161 | 6.90954E-25 | 0.401 | −0.397 | −0.397 | 8.957 | 22.326 | 0.806 | 0.660 | 0.951 |
| cg08112940 | 6 | ADGB | −23.973 | 1.0642E-24 | 0.258 | −0.588 | −0.588 | 3.708 | 14.349 | 0.753 | 0.593 | 0.913 |
| cg08923160 | 16 | APOB48R | −23.821 | 1.51052E-24 | 0.438 | −0.359 | −0.359 | 10.983 | 25.096 | 0.790 | 0.640 | 0.940 |
| cg19047707 | 2 | ECEL1 | −23.754 | 1.76235E-24 | 0.241 | −0.617 | −0.617 | 3.287 | 13.623 | 0.762 | 0.604 | 0.920 |
| cg18058230 | 3 | TNIK | −23.641 | 2.28813E-24 | 0.382 | −0.418 | −0.418 | 7.825 | 20.492 | 0.759 | 0.600 | 0.918 |
| cg03521113 | 12 | LRMP | −23.626 | 2.36372E-24 | 0.223 | −0.652 | −0.652 | 2.882 | 12.946 | 0.778 | 0.624 | 0.931 |
| cg21696827 | 17 | KIAA0753 | −23.607 | 2.47093E-24 | 0.464 | −0.333 | −0.333 | 12.776 | 27.505 | 0.750 | 0.589 | 0.911 |
| cg09474331 | 19 | TTYH1 | −23.586 | 2.59257E-24 | 0.217 | −0.663 | −0.663 | 2.774 | 12.764 | 0.756 | 0.597 | 0.916 |
| cg07117012 | 12 | AQP2 | −23.356 | 4.40563E-24 | 0.439 | −0.357 | −0.357 | 10.882 | 24.783 | 0.756 | 0.597 | 0.916 |
| cg13431464 | 18 | PTPN2 | −23.264 | 5.44044E-24 | 0.462 | −0.335 | −0.335 | 12.448 | 26.925 | 0.759 | 0.600 | 0.918 |
| cg18150439 | 2 | NXPH2 | −23.079 | 8.33465E-24 | 0.187 | −0.729 | −0.729 | 2.182 | 11.678 | 0.753 | 0.593 | 0.913 |
| cg22707438 | 11 | DGKZ | −23.041 | 9.09571E-24 | 0.405 | −0.393 | −0.393 | 8.750 | 21.631 | 0.759 | 0.600 | 0.918 |
| cg24674189 | 13 | BRCA2 | −22.978 | 1.05213E-23 | 0.456 | −0.341 | −0.341 | 11.859 | 26.005 | 0.750 | 0.589 | 0.911 |
| cg19413693 | 1 | VAV3 | −22.943 | 1.13911E-23 | 0.436 | −0.361 | −0.361 | 10.508 | 24.106 | 0.759 | 0.600 | 0.918 |
| cg24644188 | 5 | FYB | −22.849 | 1.41616E-23 | 0.408 | −0.389 | −0.389 | 8.860 | 21.721 | 0.756 | 0.597 | 0.916 |
| cg25769852 | 12 | CD69 | −22.845 | 1.43041E-23 | 0.424 | −0.373 | −0.373 | 9.751 | 22.997 | 0.812 | 0.669 | 0.955 |
| cg15917517 | 12 | APPL2 | −22.839 | 1.44843E-23 | 0.479 | −0.320 | −0.320 | 13.479 | 28.167 | 0.772 | 0.616 | 0.927 |
| cg20132609 | 13 | DOCK9 | −22.776 | 1.67637E-23 | 0.255 | −0.593 | −0.593 | 3.475 | 13.628 | 0.753 | 0.593 | 0.913 |
| cg14104842 | 7 | NRCAM | −22.250 | 5.62531 E-23 | 0.476 | −0.322 | −0.322 | 12.995 | 27.282 | 0.781 | 0.628 | 0.934 |
| cg20804072 | 17 | CCL4L1 | −22.245 | 5.6851 E-23 | 0.449 | −0.347 | −0.347 | 11.067 | 24.629 | 0.762 | 0.604 | 0.920 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg01636080 | 1 | WASF2 | −22.212 | 6.13893E-23 | 0.442 | −0.355 | −0.355 | 10.580 | 23.935 | 0.787 | 0.636 | 0.938 |
| cg19071452 | 2 | NMI | −22.198 | 6.33629E-23 | 0.362 | −0.441 | −0.441 | 6.574 | 18.154 | 0.846 | 0.715 | 0.977 |
| cg03050022 | 15 | RAB27A | −22.066 | 8.58867E-23 | 0.463 | −0.334 | −0.334 | 11.916 | 25.737 | 0.756 | 0.597 | 0.916 |
| cg24129356 | 6 | HLA-DMA | −22.021 | 9.53863E-23 | 0.430 | −0.366 | −0.366 | 9.799 | 22.764 | 0.861 | 0.737 | 0.986 |
| cg00832555 | 3 | LRRC34 | −21.978 | 1.05316E-22 | 0.416 | −0.381 | −0.381 | 8.969 | 21.566 | 0.867 | 0.745 | 0.989 |
| cg12386061 | 3 | CTDSPL | −21.797 | 1.59598E-22 | 0.375 | −0.426 | −0.426 | 6.987 | 18.628 | 0.821 | 0.681 | 0.961 |
| cg15480817 | 5 | TMEM171 | −21.768 | 1.70455E-22 | 0.269 | −0.570 | −0.570 | 3.671 | 13.629 | 0.750 | 0.589 | 0.911 |
| cg16049690 | 5 | BTNL9 | −21.728 | 1.87114E-22 | 0.442 | −0.354 | −0.354 | 10.396 | 23.497 | 0.815 | 0.673 | 0.957 |
| cg03477757 | 13 | GJB2 | −21.694 | 2.02329E-22 | 0.254 | −0.595 | −0.595 | 3.321 | 13.066 | 0.769 | 0.612 | 0.925 |
| cg23724711 | 12 | WIBG | −21.679 | 2.09182E-22 | 0.349 | −0.458 | −0.458 | 5.936 | 17.033 | 0.747 | 0.585 | 0.909 |
| cg26070834 | 5 | POLK | −21.637 | 2.30562E-22 | 0.473 | −0.325 | −0.325 | 12.436 | 26.284 | 0.769 | 0.612 | 0.925 |
| cg23474501 | 10 | GPR123 | −21.574 | 2.66714E-22 | 0.253 | −0.597 | −0.597 | 3.284 | 12.972 | 0.790 | 0.640 | 0.940 |
| cg22026423 | 10 | BUB3 | −21.564 | 2.73084E-22 | 0.359 | −0.445 | −0.445 | 6.278 | 17.502 | 0.846 | 0.715 | 0.977 |
| cg26902581 | 2 | ITGA6 | −21.551 | 2.81476E-22 | 0.417 | −0.380 | −0.380 | 8.884 | 21.290 | 0.775 | 0.620 | 0.929 |
| cg11905061 | 2 | AGAP1 | −21.522 | 3.00947E-22 | 0.492 | −0.308 | −0.308 | 13.811 | 28.096 | 0.756 | 0.597 | 0.916 |
| cg06345712 | 11 | MAML2 | −21.490 | 3.23856E-22 | 0.454 | −0.343 | −0.343 | 11.015 | 24.271 | 0.759 | 0.600 | 0.918 |
| cg22499994 | 10 | CUBN | −21.462 | 3.44865E-22 | 0.403 | −0.394 | −0.394 | 8.154 | 20.211 | 0.762 | 0.604 | 0.920 |
| cg00166343 | 17 | CRLF3 | −21.459 | 3.47496E-22 | 0.488 | −0.312 | −0.312 | 13.493 | 27.645 | 0.790 | 0.640 | 0.940 |
| cg25997979 | 10 | ZMIZ1 | −21.432 | 3.69783E-22 | 0.233 | −0.633 | −0.633 | 2.858 | 12.269 | 0.815 | 0.673 | 0.957 |
| cg13620034 | 8 | MSC | −21.366 | 4.30693E-22 | 0.345 | −0.463 | −0.463 | 5.724 | 16.612 | 0.812 | 0.669 | 0.955 |
| cg07801620 | 11 | CAT | −21.259 | 5.50739E-22 | 0.495 | −0.306 | −0.306 | 13.911 | 28.126 | 0.843 | 0.711 | 0.975 |
| cg06393885 | 5 | GALNT10 | −21.039 | 9.13705E-22 | 0.366 | −0.437 | −0.437 | 6.400 | 17.505 | 0.920 | 0.824 | 1.000 |
| cg20569893 | 17 | FLOT2 | −21.007 | 9.8486E-22 | 0.393 | −0.406 | −0.406 | 7.497 | 19.099 | 0.904 | 0.800 | 1.000 |
| cg04869854 | 11 | ATPGD1 | −20.974 | 1.06167E-21 | 0.450 | −0.346 | −0.346 | 10.557 | 23.438 | 0.762 | 0.604 | 0.920 |
| cg18752527 | 2 | HECW2 | −20.939 | 1.15181E-21 | 0.433 | −0.364 | −0.364 | 9.501 | 21.944 | 0.784 | 0.632 | 0.936 |
| cg19391966 | 17 | TNK1 | −20.918 | 1.20881E-21 | 0.284 | −0.546 | −0.546 | 3.898 | 13.716 | 0.796 | 0.648 | 0.944 |
| cg12881222 | 7 | STEAP1B | −20.830 | 1.47903E-21 | 0.440 | −0.357 | −0.357 | 9.845 | 22.388 | 0.787 | 0.636 | 0.938 |
| cg16902746 | 19 | PTPRS | −20.798 | 1.59183E-21 | 0.393 | −0.406 | −0.406 | 7.435 | 18.936 | 0.778 | 0.624 | 0.931 |
| cg03094728 | 7 | AKAP9 | −20.787 | 1.63217E-21 | 0.465 | −0.333 | −0.333 | 11.401 | 24.536 | 0.769 | 0.612 | 0.925 |
| cg22407154 | 17 | CCL4L1; CCL4L2 | −20.721 | 1.90004E-21 | 0.474 | −0.324 | −0.324 | 12.017 | 25.355 | 0.861 | 0.737 | 0.986 |
| cg16909402 | 1 | CD48 | −20.706 | 1.96713E-21 | 0.460 | −0.337 | −0.337 | 11.070 | 24.048 | 0.753 | 0.593 | 0.913 |
| cg25563256 | 17 | FGF11 | −20.700 | 1.99317E-21 | 0.479 | −0.320 | −0.320 | 12.369 | 25.826 | 0.806 | 0.660 | 0.951 |
| cg09142829 | 12 | CLEC4A | −20.699 | 2.00105E-21 | 0.494 | −0.306 | −0.306 | 13.522 | 27.381 | 0.769 | 0.612 | 0.925 |
| cg11696165 | 12 | PXN | −20.661 | 2.18201E-21 | 0.485 | −0.314 | −0.314 | 12.817 | 26.417 | 0.778 | 0.624 | 0.931 |
| cg16931416 | 10 | INPP5A | −20.618 | 2.40886E-21 | 0.290 | −0.537 | −0.537 | 3.995 | 13.771 | 0.778 | 0.624 | 0.931 |
| cg06147863 | 11 | SPI1 | −20.566 | 2.7185E-21 | 0.474 | −0.324 | −0.324 | 11.942 | 25.192 | 0.781 | 0.628 | 0.934 |
| cg22019177 | 11 | DIXDC1 | −20.547 | 2.83692E-21 | 0.320 | −0.495 | −0.495 | 4.784 | 14.939 | 0.750 | 0.589 | 0.911 |
| cg11824639 | 1 | TCTEX1D1 | −20.450 | 3.54841E-21 | 0.323 | −0.490 | −0.490 | 4.855 | 15.014 | 0.762 | 0.604 | 0.920 |
| cg12610471 | 10 | SPAG6 | −20.386 | 4.11033E-21 | 0.473 | −0.326 | −0.326 | 11.740 | 24.845 | 0.781 | 0.628 | 0.934 |
| cg21726846 | 3 | KALRN | −20.331 | 4.6619E-21 | 0.349 | −0.457 | −0.457 | 5.634 | 16.136 | 0.750 | 0.589 | 0.911 |
| cg19446512 | 9 | RNF38 | −20.322 | 4.76089E-21 | 0.405 | −0.393 | −0.393 | 7.828 | 19.335 | 0.821 | 0.681 | 0.961 |
| cg07998137 | 3 | MAGI1 | −20.296 | 5.05621E-21 | 0.426 | −0.370 | −0.370 | 8.868 | 20.812 | 0.775 | 0.620 | 0.929 |
| cg03309253 | 19 | LTBP4 | −20.197 | 6.35646E-21 | 0.304 | −0.518 | −0.518 | 4.266 | 14.048 | 0.769 | 0.620 | 0.925 |
| cg18954401 | 4 | PRDM8 | −20.135 | 7.33058E-21 | 0.474 | −0.324 | −0.324 | 11.717 | 24.716 | 0.784 | 0.632 | 0.936 |
| cg12795959 | 20 | SIRPB1 | −20.059 | 8.73007E-21 | 0.324 | −0.490 | −0.490 | 4.788 | 14.788 | 0.747 | 0.585 | 0.909 |
| cg01974370 | 1 | NBPF20 | −20.036 | 9.20672E-21 | 0.341 | −0.467 | −0.467 | 5.302 | 15.546 | 0.787 | 0.636 | 0.938 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg19823803 | 4 | KIT | −20.006 | 9.86694E-21 | 0.398 | −0.400 | −0.400 | 7.426 | 18.644 | 0.824 | 0.685 | 0.963 |
| cg23807071 | 7 | MAD1L1 | −19.957 | 1.10289E-20 | 0.382 | −0.418 | −0.418 | 6.727 | 17.613 | 0.775 | 0.620 | 0.929 |
| cg10977770 | 1 | ESRRG | −19.841 | 1.44257E-20 | 0.483 | −0.316 | −0.316 | 12.166 | 25.210 | 0.753 | 0.593 | 0.913 |
| cg05364588 | 3 | MECOM | −19.837 | 1.45702E-20 | 0.409 | −0.388 | −0.388 | 7.858 | 19.204 | 0.756 | 0.597 | 0.916 |
| cg27510024 | 2 | RFX8 | −19.762 | 1.72808E-20 | 0.478 | −0.320 | −0.320 | 11.818 | 24.707 | 0.806 | 0.660 | 0.951 |
| cg19977280 | 22 | APOBEC3D | −19.748 | 1.78762E-20 | 0.329 | −0.483 | −0.483 | 4.861 | 14.795 | 0.769 | 0.612 | 0.925 |
| cg16514615 | 5 | RASGEF1C | −19.661 | 2.18228E-20 | 0.396 | −0.402 | −0.402 | 7.207 | 18.206 | 0.765 | 0.608 | 0.923 |
| cg00579036 | 6 | CMAH | −19.606 | 2.47604E-20 | 0.294 | −0.532 | −0.532 | 3.916 | 13.335 | 0.765 | 0.608 | 0.923 |
| cg27634876 | 14 | PTGDR | −19.441 | 3.6212E-20 | 0.273 | −0.563 | −0.563 | 3.432 | 12.554 | 0.775 | 0.620 | 0.929 |
| cg12079322 | 2 | GALNT13 | −19.415 | 3.84937E-20 | 0.205 | −0.689 | −0.689 | 2.174 | 10.626 | 0.772 | 0.616 | 0.927 |
| cg01599770 | 1 | PDE4B | −19.235 | 5.81819E-20 | 0.458 | −0.339 | −0.339 | 10.197 | 22.275 | 0.775 | 0.620 | 0.929 |
| cg10355355 | 17 | PITPNM3 | −19.182 | 6.57334E-20 | 0.456 | −0.341 | −0.341 | 10.074 | 22.084 | 0.750 | 0.589 | 0.911 |
| cg11753540 | 11 | ADM | −19.159 | 6.93513E-20 | 0.283 | −0.549 | −0.549 | 3.591 | 12.707 | 0.787 | 0.636 | 0.938 |
| cg02694427 | 2 | HOXD12 | −19.060 | 8.71401E-20 | 0.467 | −0.331 | −0.331 | 10.674 | 22.865 | 0.775 | 0.620 | 0.929 |
| cg07625529 | 2 | HOXD10 | −19.034 | 9.24092E-20 | 0.467 | −0.331 | −0.331 | 10.641 | 22.810 | 0.769 | 0.612 | 0.925 |
| cg16441238 | 14 | EVL | −18.884 | 1.30735E-19 | 0.447 | −0.350 | −0.350 | 9.393 | 21.022 | 0.753 | 0.593 | 0.913 |
| cg03852144 | 5 | GLRX | −18.879 | 1.32248E-19 | 0.455 | −0.342 | −0.342 | 9.858 | 21.668 | 0.772 | 0.616 | 0.927 |
| cg21201099 | 17 | TBX2 | −18.832 | 1.47177E-19 | 0.431 | −0.365 | −0.365 | 8.548 | 19.817 | 0.756 | 0.597 | 0.916 |
| cg00339488 | 4 | DCHS2 | −18.779 | 1.66422E-19 | 0.354 | −0.451 | −0.451 | 5.418 | 15.299 | 0.753 | 0.593 | 0.913 |
| cg14085715 | 7 | MACC1 | −18.746 | 1.79412E-19 | 0.377 | −0.423 | −0.423 | 6.198 | 16.426 | 0.792 | 0.642 | 0.941 |
| cg07799539 | 12 | ASCL1 | −18.741 | 1.81578E-19 | 0.424 | −0.373 | −0.373 | 8.155 | 19.229 | 0.778 | 0.624 | 0.931 |
| cg04961466 | 4 | NPY5R | −18.632 | 2.33102E-19 | 0.362 | −0.442 | −0.442 | 5.623 | 15.549 | 0.747 | 0.585 | 0.909 |
| cg14666113 | 8 | GATA4 | −18.613 | 2.43589E-19 | 0.288 | −0.540 | −0.540 | 3.634 | 12.601 | 0.821 | 0.681 | 0.961 |
| cg05040232 | 3 | GP5 | −18.568 | 2.70631E-19 | 0.376 | −0.424 | −0.424 | 6.111 | 16.237 | 0.772 | 0.616 | 0.927 |
| cg00663077 | 4 | ZFP42 | −18.476 | 3.33961E-19 | 0.461 | −0.336 | −0.336 | 10.046 | 21.772 | 0.809 | 0.664 | 0.953 |
| cg04228935 | 21 | RUNX1 | −18.449 | 3.5543E-19 | 0.303 | −0.518 | −0.518 | 3.953 | 13.026 | 0.747 | 0.585 | 0.909 |
| cg23906261 | 10 | GFRA1 | −18.357 | 4.40045E-19 | 0.378 | −0.422 | −0.422 | 6.118 | 16.174 | 0.781 | 0.628 | 0.934 |
| cg06499262 | 16 | NFAT5 | −18.287 | 5.16126E-19 | 0.479 | −0.320 | −0.320 | 11.060 | 23.088 | 0.756 | 0.597 | 0.916 |
| cg08067617 | 19 | F2RL3 | −18.211 | 6.14802E-19 | 0.372 | −0.429 | −0.429 | 5.863 | 15.755 | 0.815 | 0.673 | 0.957 |
| cg25747192 | 3 | RASSF1 | −18.172 | 6.72405E-19 | 0.388 | −0.411 | −0.411 | 6.437 | 16.571 | 0.799 | 0.652 | 0.947 |
| cg10143426 | 1 | TP73; WDR8 | −18.107 | 7.8074E-19 | 0.318 | −0.498 | −0.498 | 4.241 | 13.344 | 0.790 | 0.640 | 0.940 |
| cg08218360 | 6 | NUDT3 | −17.963 | 1.08889E-18 | 0.471 | −0.327 | −0.327 | 10.382 | 22.034 | 0.836 | 0.702 | 0.971 |
| cg19651694 | 11 | PHOX2A | −17.894 | 1.27784E-18 | 0.360 | −0.443 | −0.443 | 5.395 | 14.967 | 0.796 | 0.648 | 0.944 |
| cg16536329 | 5 | ZNF454 | −17.874 | 1.33747E-18 | 0.478 | −0.320 | −0.320 | 10.788 | 22.552 | 0.799 | 0.652 | 0.947 |
| cg23724557 | 3 | ZBTB20 | −17.807 | 1.5603E-18 | 0.460 | −0.337 | −0.337 | 9.650 | 20.966 | 0.778 | 0.624 | 0.931 |
| cg19814116 | 1 | KCNAB2 | −17.626 | 2.36749E-18 | 0.286 | −0.544 | −0.544 | 3.421 | 11.975 | 0.765 | 0.608 | 0.923 |
| cg03530294 | 22 | APOL3 | −17.445 | 3.59302E-18 | 0.351 | −0.455 | −0.455 | 4.989 | 14.223 | 0.821 | 0.681 | 0.961 |
| cg08493294 | 2 | DNMT3A | −17.438 | 3.65131E-18 | 0.445 | −0.352 | −0.352 | 8.629 | 19.408 | 0.756 | 0.597 | 0.916 |
| cg19677607 | 8 | NEFM | −17.343 | 4.54039E-18 | 0.248 | −0.606 | −0.606 | 2.662 | 10.756 | 0.781 | 0.628 | 0.934 |
| cg04207218 | 21 | ERG | −17.325 | 4.73122E-18 | 0.405 | −0.393 | −0.393 | 6.792 | 16.778 | 0.759 | 0.600 | 0.918 |
| cg14025053 | 8 | BAALC | −17.277 | 5.28266E-18 | 0.385 | −0.415 | −0.415 | 6.025 | 15.664 | 0.750 | 0.589 | 0.911 |
| cg17608171 | 14 | LINC01599 | −17.211 | 6.14739E-18 | 0.378 | −0.423 | −0.423 | 5.765 | 15.268 | 0.772 | 0.616 | 0.927 |
| cg24104241 | 1 | ACTA1 | −17.163 | 6.87272E-18 | 0.442 | −0.354 | −0.354 | 8.389 | 18.968 | 0.846 | 0.715 | 0.977 |
| cg03957481 | 22 | KLHDC7B | −17.107 | 7.81035E-18 | 0.200 | −0.699 | −0.699 | 1.911 | 9.558 | 0.855 | 0.728 | 0.982 |
| cg25720793 | 1 | F11R | −17.011 | 9.75525E-18 | 0.321 | −0.493 | −0.493 | 4.113 | 12.800 | 0.790 | 0.640 | 0.940 |
| cg24211504 | 6 | SIM1 | −16.954 | 1.11055E-17 | 0.430 | −0.367 | −0.367 | 7.713 | 17.944 | 0.775 | 0.620 | 0.929 |
| cg17665121 | 4 | TBC1D1 | −16.937 | 1.15573E-17 | 0.292 | −0.535 | −0.535 | 3.433 | 11.776 | 0.765 | 0.608 | 0.923 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg17527798 | 3 | LTF | -16.875 | 1.33291E-17 | 0.469 | -0.328 | -0.328 | 9.705 | 20.676 | 0.756 | 0.597 | 0.916 |
| cg19793962 | 1 | PIK3CD | -16.765 | 1.71644E-17 | 0.479 | -0.320 | -0.320 | 10.188 | 21.292 | 0.784 | 0.632 | 0.936 |
| cg22504849 | 5 | FBXW11 | -16.687 | 2.05529E-17 | 0.410 | -0.387 | -0.387 | 6.780 | 16.530 | 0.762 | 0.604 | 0.920 |
| cg03307717 | 21 | U2AF1 | -16.667 | 2.15156E-17 | 0.488 | -0.311 | -0.311 | 10.753 | 22.018 | 0.843 | 0.711 | 0.975 |
| cg05145609 | 11 | CRYAB; HSPB2 | -16.607 | 2.46986E-17 | 0.445 | -0.351 | -0.351 | 8.295 | 18.625 | 0.799 | 0.652 | 0.947 |
| cg13631572 | 14 | ADCY4 | -16.556 | 2.77797E-17 | 0.304 | -0.517 | -0.517 | 3.636 | 11.953 | 0.849 | 0.719 | 0.978 |
| cg18172877 | 5 | IRX4 | -16.432 | 3.70197E-17 | 0.470 | -0.328 | -0.328 | 9.513 | 20.237 | 0.756 | 0.597 | 0.916 |
| cg10821845 | 8 | LY6H | -16.415 | 3.84598E-17 | 0.308 | -0.511 | -0.511 | 3.700 | 12.002 | 0.772 | 0.616 | 0.927 |
| cg15762032 | 10 | GAD2 | -16.338 | 4.59479E-17 | 0.375 | -0.426 | -0.426 | 5.443 | 14.501 | 0.855 | 0.728 | 0.982 |
| cg04379606 | 16 | ZNF75A; TIGD7 | -16.316 | 4.82615E-17 | 0.314 | -0.503 | -0.503 | 3.806 | 12.126 | 0.809 | 0.664 | 0.953 |
| cg08097144 | 13 | ALOX5AP | -15.933 | 1.1661E-16 | 0.444 | -0.353 | -0.353 | 7.932 | 17.863 | 0.799 | 0.652 | 0.947 |
| cg02812947 | 8 | ADCY8 | -15.904 | 1.24617E-16 | 0.339 | -0.470 | -0.470 | 4.308 | 12.720 | 0.799 | 0.652 | 0.947 |
| cg02996471 | 19 | S1PR4 | -15.866 | 1.36125E-16 | 0.391 | -0.408 | -0.408 | 5.809 | 14.857 | 0.769 | 0.612 | 0.925 |
| cg23677243 | 15 | MEIS2 | -15.840 | 1.44489E-16 | 0.454 | -0.343 | -0.343 | 8.375 | 18.440 | 0.809 | 0.664 | 0.953 |
| cg10109500 | 3 | GHSR | -15.723 | 1.89253E-16 | 0.440 | -0.356 | -0.356 | 7.677 | 17.429 | 0.784 | 0.632 | 0.936 |
| cg00225623 | 13 | SPATA13 | -15.619 | 2.40298E-16 | 0.384 | -0.416 | -0.416 | 5.501 | 14.332 | 0.824 | 0.685 | 0.963 |
| cg23849169 | 6 | HCG4 | -15.619 | 2.40464E-16 | 0.431 | -0.365 | -0.365 | 7.228 | 16.765 | 0.772 | 0.616 | 0.927 |
| cg25614907 | 5 | IRX4 | -15.539 | 2.88755E-16 | 0.499 | -0.302 | -0.302 | 10.734 | 21.529 | 0.806 | 0.660 | 0.951 |
| cg18419977 | 11 | SLC22A18 | -15.459 | 3.47273E-16 | 0.404 | -0.393 | -0.393 | 6.135 | 15.172 | 0.806 | 0.660 | 0.951 |
| cg01698105 | 6 | LRRC16A | -15.451 | 3.53967E-16 | 0.394 | -0.405 | -0.405 | 5.770 | 14.654 | 0.823 | 0.683 | 0.962 |
| cg06085985 | 11 | EFCAB4A | -15.411 | 3.87875E-16 | 0.490 | -0.310 | -0.310 | 10.129 | 20.661 | 0.772 | 0.616 | 0.927 |
| cg17277890 | 11 | TRIM22 | -15.258 | 5.52092E-16 | 0.404 | -0.393 | -0.393 | 6.065 | 15.001 | 0.806 | 0.660 | 0.951 |
| cg24604213 | 2 | SP140L | -15.202 | 6.28074E-16 | 0.371 | -0.431 | -0.431 | 4.991 | 13.460 | 0.818 | 0.677 | 0.959 |
| cg04052466 | 19 | AMH | -15.148 | 7.11424E-16 | 0.500 | -0.301 | -0.301 | 10.560 | 21.132 | 0.787 | 0.636 | 0.938 |
| ch.3.1226245F | 3 | ERC2 | -15.134 | 7.34476E-16 | 0.279 | -0.554 | -0.554 | 2.924 | 10.461 | 0.830 | 0.694 | 0.967 |
| cg01729827 | 20 | CBLN4 | -15.044 | 9.04134E-16 | 0.435 | -0.361 | -0.361 | 7.164 | 16.459 | 0.750 | 0.589 | 0.911 |
| cg14307443 | 4 | GALNTL6 | -14.839 | 1.44757E-15 | 0.254 | -0.595 | -0.595 | 2.467 | 9.704 | 0.756 | 0.597 | 0.916 |
| cg07212778 | 2 | C1QL2 | -14.690 | 2.03981E-15 | 0.227 | -0.644 | -0.644 | 2.059 | 9.062 | 0.802 | 0.656 | 0.949 |
| cg26723002 | 8 | PLAG1 | -14.649 | 2.24235E-15 | 0.420 | -0.377 | -0.377 | 6.411 | 15.263 | 0.747 | 0.585 | 0.909 |
| cg04263436 | 6 | B3GALT4 | -14.645 | 2.26722E-15 | 0.269 | -0.571 | -0.571 | 2.669 | 9.936 | 0.793 | 0.644 | 0.942 |
| cg09870066 | 2 | CNRIP1 | -14.519 | 3.02651E-15 | 0.418 | -0.379 | -0.379 | 6.281 | 15.033 | 0.775 | 0.620 | 0.929 |
| cg06157602 | 5 | PCDHGA8 | -14.480 | 3.31189E-15 | 0.493 | -0.307 | -0.307 | 9.746 | 19.762 | 0.769 | 0.612 | 0.925 |
| cg27599271 | 14 | RIPK3 | -14.475 | 3.34965E-15 | 0.396 | -0.402 | -0.402 | 5.544 | 13.986 | 0.827 | 0.689 | 0.965 |
| cg03055966 | 11 | SBF2 | -14.423 | 3.77574E-15 | 0.414 | -0.383 | -0.383 | 5.709 | 14.758 | 0.747 | 0.585 | 0.909 |
| cg26182487 | 5 | ABLIM3 | -14.410 | 3.89261E-15 | 0.333 | -0.478 | -0.478 | 3.844 | 11.554 | 0.775 | 0.620 | 0.929 |
| cg02737619 | 1 | SKI | -14.393 | 4.04536E-15 | 0.312 | -0.506 | -0.506 | 3.403 | 10.915 | 0.747 | 0.585 | 0.909 |
| cg04136610 | 5 | ADAMTS16 | -14.391 | 4.06145E-15 | 0.439 | -0.358 | -0.358 | 7.026 | 16.020 | 0.756 | 0.597 | 0.916 |
| cg20779757 | 15 | ANPEP | -14.265 | 5.42639E-15 | 0.443 | -0.354 | -0.354 | 7.139 | 16.128 | 0.793 | 0.644 | 0.942 |
| cg08159065 | 5 | GABRB2 | -14.119 | 7.60104E-15 | 0.485 | -0.315 | -0.315 | 9.052 | 18.679 | 0.747 | 0.585 | 0.909 |
| cg03606646 | 6 | GFOD1 | -14.020 | 9.55987E-15 | 0.489 | -0.311 | -0.311 | 9.235 | 18.884 | 0.750 | 0.589 | 0.911 |
| cg17240760 | 1 | CD53 | -14.003 | 9.94145E-15 | 0.483 | -0.316 | -0.316 | 8.906 | 18.434 | 0.796 | 0.648 | 0.944 |
| cg25924217 | 17 | NPTX1 | -14.002 | 9.9582E-15 | 0.399 | -0.399 | -0.399 | 5.469 | 13.710 | 0.809 | 0.664 | 0.953 |
| cg23882019 | 8 | TNFRSF10A | -13.928 | 1.17991E-14 | 0.364 | -0.438 | -0.438 | 4.479 | 12.291 | 0.759 | 0.600 | 0.918 |
| cg13528854 | 4 | BST1 | -13.843 | 1.43407E-14 | 0.422 | -0.375 | -0.375 | 6.176 | 14.636 | 0.870 | 0.750 | 0.991 |
| cg06675190 | 15 | ACAN | -13.839 | 1.44917E-14 | 0.299 | -0.524 | -0.524 | 3.065 | 10.251 | 0.793 | 0.644 | 0.942 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg20684253 | 16 | PRKCB | −13.810 | 1.54928E-14 | 0.408 | −0.389 | −0.389 | 5.699 | 13.961 | 0.775 | 0.620 | 0.929 |
| cg07836142 | 6 | ZSCAN23 | −13.772 | 1.69033E-14 | 0.379 | −0.421 | −0.421 | 4.821 | 12.719 | 0.772 | 0.616 | 0.927 |
| cg07272395 | 4 | MGAT4D | −13.762 | 1.7309E-14 | 0.426 | −0.371 | −0.371 | 6.280 | 14.750 | 0.775 | 0.620 | 0.929 |
| cg25781595 | 19 | GRIN2D | −13.754 | 1.76271E-14 | 0.465 | −0.333 | −0.333 | 7.871 | 16.930 | 0.747 | 0.585 | 0.909 |
| cg26405376 | 5 | RNF44 | −13.569 | 2.69917E-14 | 0.408 | −0.390 | −0.390 | 5.598 | 13.731 | 0.821 | 0.681 | 0.961 |
| cg15596749 | 1 | BLACAT1 | −13.423 | 3.77171E-14 | 0.426 | −0.371 | −0.371 | 6.142 | 14.431 | 0.812 | 0.669 | 0.955 |
| cg01364478 | 1 | PRRX1 | −13.365 | 4.31121E-14 | 0.491 | −0.309 | −0.309 | 8.967 | 18.254 | 0.750 | 0.589 | 0.911 |
| cg13409544 | 14 | ERO1A | −13.353 | 4.43689E-14 | 0.387 | −0.412 | −0.412 | 4.911 | 12.696 | 0.769 | 0.612 | 0.925 |
| cg06470626 | 16 | CDR2 | −13.142 | 7.20618E-14 | 0.486 | −0.314 | −0.314 | 8.538 | 17.585 | 0.796 | 0.648 | 0.944 |
| cg06604289 | 1 | PRDM2 | −13.066 | 8.5935E-14 | 0.464 | −0.334 | −0.334 | 7.469 | 16.110 | 0.753 | 0.593 | 0.913 |
| cg19434381 | 17 | B3GNTL1 | −12.944 | 1.13733E-13 | 0.441 | −0.355 | −0.355 | 6.507 | 14.745 | 0.784 | 0.632 | 0.936 |
| cg21215767 | 2 | EN1 | −12.931 | 1.17226E-13 | 0.481 | −0.317 | −0.317 | 8.208 | 17.049 | 0.790 | 0.640 | 0.940 |
| cg15508761 | 6 | HIVEP2 | −12.887 | 1.2972E-13 | 0.481 | −0.318 | −0.318 | 8.153 | 16.956 | 0.769 | 0.612 | 0.925 |
| cg17579384 | 1 | GCSAML | −12.856 | 1.39399E-13 | 0.459 | −0.339 | −0.339 | 7.144 | 15.579 | 0.809 | 0.664 | 0.953 |
| cg20601481 | 11 | ANKRD13D | −12.841 | 1.4423E-13 | 0.316 | −0.500 | −0.500 | 3.198 | 10.104 | 0.849 | 0.719 | 0.978 |
| cg15731655 | 12 | HOTAIR | −12.800 | 1.58554E-13 | 0.414 | −0.383 | −0.383 | 5.511 | 13.319 | 0.781 | 0.628 | 0.934 |
| cg12691994 | 1 | RASSF5 | −12.726 | 1.88136E-13 | 0.487 | −0.313 | −0.313 | 8.350 | 17.154 | 0.784 | 0.632 | 0.936 |
| cg03887163 | 1 | LMX1A | −12.698 | 2.00385E-13 | 0.440 | −0.357 | −0.357 | 6.334 | 14.411 | 0.781 | 0.628 | 0.934 |
| cg26309194 | 21 | TMPRSS2 | −12.638 | 2.30126E-13 | 0.488 | −0.311 | −0.311 | 8.373 | 17.145 | 0.747 | 0.585 | 0.909 |
| cg00803453 | 2 | SPEG | −12.619 | 2.40505E-13 | 0.374 | −0.427 | −0.427 | 4.353 | 11.647 | 0.799 | 0.652 | 0.947 |
| cg26778001 | 19 | LILRB1 | −12.613 | 2.44007E-13 | 0.432 | −0.365 | −0.365 | 6.027 | 13.957 | 0.756 | 0.597 | 0.916 |
| cg04510788 | 1 | GRIK3 | −12.594 | 2.54762E-13 | 0.342 | −0.466 | −0.466 | 3.646 | 10.648 | 0.793 | 0.644 | 0.942 |
| cg16927040 | 3 | SST | −12.457 | 3.49497E-13 | 0.424 | −0.372 | −0.372 | 5.711 | 13.462 | 0.836 | 0.702 | 0.971 |
| cg27234340 | 17 | ASGR1 | −12.452 | 3.53071E-13 | 0.422 | −0.375 | −0.375 | 5.633 | 13.352 | 0.778 | 0.624 | 0.931 |
| cg03290752 | 3 | TBL1XR1 | −12.425 | 3.76048E-13 | 0.424 | −0.372 | −0.372 | 5.698 | 13.431 | 0.824 | 0.685 | 0.963 |
| cg13916762 | 6 | NHSL1 | −12.394 | 4.0382E-13 | 0.487 | −0.312 | −0.312 | 8.169 | 16.768 | 0.787 | 0.636 | 0.938 |
| cg12205413 | 6 | BACH2 | −12.303 | 4.98124E-13 | 0.455 | −0.342 | −0.342 | 6.745 | 14.810 | 0.818 | 0.677 | 0.959 |
| cg05070626 | 16 | SYT17 | −12.221 | 6.01618E-13 | 0.347 | −0.460 | −0.460 | 3.648 | 10.518 | 0.776 | 0.622 | 0.930 |
| cg19470964 | 15 | LINC01585 | −12.200 | 6.30559E-13 | 0.479 | −0.320 | −0.320 | 7.682 | 16.032 | 0.886 | 0.772 | 0.999 |
| cg06444282 | 1 | VWA5B1 | −12.124 | 7.51673E-13 | 0.484 | −0.315 | −0.315 | 7.863 | 16.242 | 0.796 | 0.648 | 0.944 |
| cg12181083 | 8 | SULF1 | −12.052 | 8.86432E-13 | 0.484 | −0.315 | −0.315 | 7.800 | 16.127 | 0.849 | 0.719 | 0.978 |
| cg14415885 | 1 | TBX15 | −12.043 | 9.05712E-13 | 0.290 | −0.537 | −0.537 | 2.618 | 9.013 | 0.802 | 0.656 | 0.949 |
| cg17736443 | 6 | HIST1H2AJ | −11.996 | 1.00813E-12 | 0.436 | −0.361 | −0.361 | 5.890 | 13.524 | 0.775 | 0.620 | 0.929 |
| cg02017282 | 17 | WNT3 | −11.955 | 1.10829E-12 | 0.447 | −0.350 | −0.350 | 6.253 | 14.000 | 0.747 | 0.585 | 0.909 |
| cg07637516 | 10 | MXI1 | −11.935 | 1.16087E-12 | 0.478 | −0.321 | −0.321 | 7.481 | 15.650 | 0.753 | 0.593 | 0.913 |
| cg21599974 | 4 | ARHGAP24 | −11.903 | 1.24889E-12 | 0.430 | −0.366 | −0.366 | 5.685 | 13.207 | 0.806 | 0.660 | 0.951 |
| cg12751305 | 1 | KCNN3 | −11.892 | 1.28352E-12 | 0.424 | −0.372 | −0.372 | 5.485 | 12.930 | 0.762 | 0.604 | 0.920 |
| cg00698595 | 11 | ETS1 | −11.831 | 1.4772E-12 | 0.473 | −0.325 | −0.325 | 7.223 | 15.258 | 0.833 | 0.698 | 0.969 |
| cg20891481 | 3 | FOXP1 | −11.804 | 1.57149E-12 | 0.455 | −0.342 | −0.342 | 6.503 | 14.278 | 0.799 | 0.652 | 0.947 |
| cg27035251 | 19 | JAK3 | −11.798 | 1.59087E-12 | 0.465 | −0.332 | −0.332 | 6.880 | 14.784 | 0.833 | 0.698 | 0.969 |
| cg26413174 | 1 | TTC22 | −11.796 | 1.5995E-12 | 0.349 | −0.458 | −0.458 | 3.581 | 10.272 | 0.753 | 0.593 | 0.913 |
| cg01151966 | 10 | NRG3 | −11.785 | 1.64223E-12 | 0.399 | −0.399 | −0.399 | 4.739 | 11.866 | 0.750 | 0.589 | 0.911 |
| cg05053923 | 5 | LINC00992 | −11.781 | 1.65627E-12 | 0.395 | −0.404 | −0.404 | 4.613 | 11.692 | 0.818 | 0.677 | 0.959 |
| cg18024479 | 7 | TFPI2 | −11.774 | 1.68159E-12 | 0.489 | −0.310 | −0.310 | 7.889 | 16.125 | 0.778 | 0.624 | 0.931 |
| cg06460568 | 11 | IGF2 | −11.704 | 1.97523E-12 | 0.366 | −0.437 | −0.437 | 3.909 | 10.693 | 0.793 | 0.644 | 0.942 |
| cg04167833 | 5 | LCP2 | −11.677 | 2.10401E-12 | 0.307 | −0.512 | −0.512 | 2.819 | 9.169 | 0.772 | 0.616 | 0.927 |
| cg22796507 | 1 | FOXE3 | −11.645 | 2.26228E-12 | 0.367 | −0.435 | −0.435 | 3.928 | 10.698 | 0.747 | 0.585 | 0.909 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CI_lower | CI_upper |
|---|---|---|---|---|---|---|---|---|---|---|---|---|
| cg19485539 | 10 | GFRA1 | -11.602 | 2.5030E-12 | 0.369 | -0.433 | -0.433 | 3.956 | 10.720 | 0.775 | 0.620 | 0.929 |
| cg10788355 | 13 | ELF1 | -11.532 | 2.9397E-12 | 0.468 | -0.330 | -0.330 | 6.838 | 14.615 | 0.747 | 0.585 | 0.909 |
| cg07703495 | 5 | ADCY2 | -11.358 | 4.3841E-12 | 0.458 | -0.339 | -0.339 | 6.376 | 13.923 | 0.756 | 0.597 | 0.916 |
| cg25975712 | 22 | FAM19A5 | -11.029 | 9.3485E-12 | 0.299 | -0.525 | -0.525 | 2.568 | 8.595 | 0.772 | 0.616 | 0.927 |
| cg05433448 | 3 | ATP2C1 | -11.019 | 9.5821E-12 | 0.417 | -0.380 | -0.380 | 4.926 | 11.827 | 0.782 | 0.630 | 0.935 |
| cg16732077 | 6 | FYN | -11.002 | 9.9610E-12 | 0.494 | -0.306 | -0.306 | 7.622 | 15.434 | 0.762 | 0.604 | 0.920 |
| cg21899942 | 14 | RGS6 | -10.950 | 1.1226E-11 | 0.463 | -0.334 | -0.334 | 6.365 | 13.738 | 0.753 | 0.593 | 0.913 |
| cg00231422 | 16 | NOL3 | -10.863 | 1.3714E-11 | 0.422 | -0.375 | -0.375 | 5.006 | 11.874 | 0.762 | 0.604 | 0.920 |
| cg23338503 | 5 | DOCK2 | -10.832 | 1.4717E-11 | 0.488 | -0.312 | -0.312 | 7.258 | 14.878 | 0.753 | 0.593 | 0.913 |
| cg03167496 | 11 | BDNF | -10.699 | 2.0011E-11 | 0.462 | -0.335 | -0.335 | 6.204 | 13.417 | 0.750 | 0.589 | 0.911 |
| cg04207385 | 6 | CNR1 | -10.684 | 2.0702E-11 | 0.393 | -0.405 | -0.405 | 4.231 | 10.752 | 0.750 | 0.589 | 0.911 |
| cg18351999 | 11 | SIGIRR | -10.679 | 2.0949E-11 | 0.465 | -0.333 | -0.333 | 6.276 | 13.505 | 0.806 | 0.660 | 0.951 |
| cg17480467 | 10 | PAX2 | -10.556 | 2.7799E-11 | 0.392 | -0.407 | -0.407 | 4.158 | 10.604 | 0.747 | 0.585 | 0.909 |
| cg27003782 | 10 | CPXM2 | -10.355 | 4.4109E-11 | 0.414 | -0.383 | -0.383 | 4.612 | 11.140 | 0.747 | 0.585 | 0.909 |
| cg13795063 | 17 | RARA | -10.214 | 6.1149E-11 | 0.388 | -0.411 | -0.411 | 3.960 | 10.205 | 0.787 | 0.636 | 0.938 |
| cg05420790 | 12 | HOXC10 | -9.931 | 1.1715E-10 | 0.413 | -0.384 | -0.384 | 4.436 | 10.737 | 0.759 | 0.600 | 0.918 |
| cg05138188 | 19 | KIRREL2 | 9.919 | 1.2045E-10 | 2.007 | 0.303 | 0.303 | 12.775 | 6.364 | 0.870 | 0.750 | 0.991 |
| cg25552416 | 17 | ZFP3 | -9.914 | 1.2184E-10 | 0.457 | -0.340 | -0.340 | 5.650 | 12.352 | 0.784 | 0.632 | 0.936 |
| cg18348337 | 5 | MCC | -9.909 | 1.2342E-10 | 0.430 | -0.366 | -0.366 | 4.860 | 11.296 | 0.775 | 0.620 | 0.929 |
| cg17929951 | 20 | PARVG | -9.821 | 1.5085E-10 | 0.396 | -0.402 | -0.402 | 4.010 | 10.122 | 0.762 | 0.604 | 0.920 |
| cg11257728 | 22 | CD40 | -9.678 | 2.1009E-10 | 0.478 | -0.321 | -0.321 | 6.197 | 12.975 | 0.775 | 0.620 | 0.929 |
| cg09158314 | 13 | TNFSF13B | -9.575 | 2.6614E-10 | 0.437 | -0.359 | -0.359 | 4.911 | 11.229 | 0.747 | 0.585 | 0.909 |
| cg18801599 | 17 | TMEM101 | -9.443 | 3.6086E-10 | 0.431 | -0.365 | -0.365 | 4.701 | 10.895 | 0.802 | 0.656 | 0.949 |
| cg05555207 | 12 | TBX5 | -9.437 | 3.6519E-10 | 0.487 | -0.313 | -0.313 | 6.386 | 13.120 | 0.772 | 0.616 | 0.927 |
| cg20956278 | 22 | SLC16A8 | -9.166 | 6.8178E-10 | 0.435 | -0.361 | -0.361 | 4.680 | 10.755 | 0.747 | 0.585 | 0.909 |
| cg27641628 | 7 | TMEM140 | -9.142 | 7.2113E-10 | 0.375 | -0.426 | -0.426 | 3.376 | 9.009 | 0.756 | 0.597 | 0.916 |
| cg11572340 | 10 | KCNIP2 | -9.088 | 8.1571E-10 | 0.471 | -0.327 | -0.327 | 5.669 | 12.026 | 0.784 | 0.632 | 0.936 |
| cg15685268 | 11 | IGSF9B | -8.997 | 1.0077E-09 | 0.459 | -0.338 | -0.338 | 5.262 | 11.454 | 0.821 | 0.681 | 0.961 |
| cg16046444 | 1 | NR5A2 | -8.925 | 1.1876E-09 | 0.466 | -0.332 | -0.332 | 5.412 | 11.620 | 0.765 | 0.608 | 0.923 |
| cg15444626 | 17 | SAMD14 | -8.845 | 1.4293E-09 | 0.484 | -0.315 | -0.315 | 5.946 | 12.284 | 0.799 | 0.652 | 0.947 |
| cg17680773 | 16 | ATF7IP2 | -8.700 | 1.9954E-09 | 0.423 | -0.374 | -0.374 | 4.198 | 9.928 | 0.772 | 0.616 | 0.927 |
| cg17336584 | 6 | PHACTR1 | -8.673 | 2.1256E-09 | 0.435 | -0.361 | -0.361 | 4.473 | 10.279 | 0.747 | 0.585 | 0.909 |
| cg02353184 | 10 | SFMBT2 | -8.550 | 2.8180E-09 | 0.421 | -0.375 | -0.375 | 4.109 | 9.749 | 0.775 | 0.620 | 0.929 |
| cg02970551 | 1 | RUNX3 | -8.482 | 3.2981E-09 | 0.473 | -0.325 | -0.325 | 5.401 | 11.414 | 0.772 | 0.616 | 0.927 |
| cg13785898 | 16 | CKLF; TK2 | -8.429 | 3.7208E-09 | 0.472 | -0.326 | -0.326 | 5.325 | 11.293 | 0.787 | 0.636 | 0.938 |
| cg21990556 | 11 | OSBPL5 | -8.391 | 4.0601E-09 | 0.443 | -0.354 | -0.354 | 4.535 | 10.244 | 0.765 | 0.608 | 0.923 |
| cg00611535 | 12 | RAB5B | -8.381 | 4.1629E-09 | 0.482 | -0.317 | -0.317 | 5.627 | 11.665 | 0.904 | 0.800 | 1.000 |
| cg19113326 | 7 | POU6F2 | -8.270 | 5.3702E-09 | 0.243 | -0.615 | -0.615 | 1.498 | 6.176 | 0.769 | 0.612 | 0.925 |
| cg09965733 | 14 | LRFN5 | -8.209 | 6.1776E-09 | 0.500 | -0.301 | -0.301 | 6.086 | 12.183 | 0.796 | 0.648 | 0.944 |
| cg06252985 | 11 | PC | -8.119 | 7.5957E-09 | 0.405 | -0.393 | -0.393 | 3.612 | 8.922 | 0.756 | 0.597 | 0.916 |
| cg17051560 | 12 | SOCS2 | -8.090 | 8.1350E-09 | 0.419 | -0.378 | -0.378 | 3.875 | 9.255 | 0.759 | 0.600 | 0.918 |
| cg15930596 | 12 | KCNA1 | -8.053 | 8.8593E-09 | 0.499 | -0.302 | -0.302 | 5.966 | 11.958 | 0.759 | 0.600 | 0.918 |
| cg27134386 | 4 | GABRA2 | -8.030 | 9.3409E-09 | 0.445 | -0.352 | -0.352 | 4.423 | 9.947 | 0.769 | 0.612 | 0.925 |
| cg05845319 | 3 | MLH1 | -7.871 | 1.3449E-08 | 0.483 | -0.316 | -0.316 | 5.350 | 11.081 | 0.809 | 0.664 | 0.953 |
| cg09085842 | 6 | HSPA1L | -7.814 | 1.5359E-08 | 0.246 | -0.609 | -0.609 | 1.471 | 5.979 | 0.773 | 0.618 | 0.928 |
| cg22060611 | 5 | NRG2 | -7.802 | 1.5766E-08 | 0.471 | -0.327 | -0.327 | 4.970 | 10.559 | 0.765 | 0.608 | 0.923 |
| cg15531403 | 8 | NPBWR1 | -7.797 | 1.5969E-08 | 0.396 | -0.402 | -0.402 | 3.343 | 8.439 | 0.784 | 0.632 | 0.936 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| ch.10.1562909R | 10 | CCDC109A | −7.783 | 1.64879E-08 | 0.477 | −0.322 | −0.322 | 5.122 | 10.747 | 0.790 | 0.640 | 0.940 |
| ch.8.1136903F | 8 | SNTG1 | −7.710 | 1.94795E-08 | 0.401 | −0.397 | −0.397 | 3.406 | 8.487 | 0.790 | 0.640 | 0.940 |
| cg24134845 | 10 | HPSE2 | −7.365 | 4.31193E-08 | 0.386 | −0.414 | −0.414 | 3.034 | 7.864 | 0.806 | 0.660 | 0.951 |
| cg11083422 | 6 | GLP1R | −7.191 | 6.44546E-08 | 0.404 | −0.394 | −0.394 | 3.270 | 8.099 | 0.769 | 0.612 | 0.925 |
| cg22715094 | 6 | HSPA1A | −7.112 | 7.73312E-08 | 0.497 | −0.304 | −0.304 | 5.311 | 10.689 | 0.753 | 0.593 | 0.913 |
| cg00091953 | 4 | INP4B | −6.844 | 1.43101E-07 | 0.469 | −0.329 | −0.329 | 4.417 | 9.426 | 0.784 | 0.632 | 0.936 |
| cg00157796 | 6 | FNDC1 | −6.273 | 5.33361E-07 | 0.288 | −0.541 | −0.541 | 1.610 | 5.591 | 0.799 | 0.652 | 0.947 |
| cg11041734 | 7 | LIMK1 | −6.172 | 6.73342E-07 | 0.490 | −0.309 | −0.309 | 4.569 | 9.316 | 0.781 | 0.628 | 0.934 |
| cg13121699 | 2 | ZNF804A | −6.028 | 9.38151E-07 | 0.421 | −0.375 | −0.375 | 3.134 | 7.437 | 0.778 | 0.624 | 0.931 |
| cg13320626 | 5 | ST8SIA4 | −5.905 | 1.24388E-06 | 0.491 | −0.309 | −0.309 | 4.412 | 8.995 | 0.775 | 0.620 | 0.929 |
| cg06786153 | 15 | TBC1D2B | −5.900 | 1.25749E-06 | 0.340 | −0.469 | −0.469 | 2.036 | 5.989 | 0.765 | 0.608 | 0.923 |
| cg14065576 | 1 | GSTM2 | −5.855 | 1.39644E-06 | 0.377 | −0.423 | −0.423 | 2.452 | 6.499 | 0.753 | 0.593 | 0.913 |
| cg16709110 | 11 | SLC25A22 | −5.395 | 4.02408E-06 | 0.455 | −0.342 | −0.342 | 3.424 | 7.522 | 0.781 | 0.628 | 0.934 |
| cg26663686 | 8 | LY6H | −5.338 | 4.5937E-06 | 0.498 | −0.303 | −0.303 | 4.228 | 8.497 | 0.750 | 0.589 | 0.911 |
| cg14426999 | 20 | TOX2 | −5.291 | 5.11798E-06 | 0.404 | −0.393 | −0.393 | 2.610 | 6.458 | 0.750 | 0.589 | 0.911 |
| cg24684739 | 11 | ZFP91 | −5.159 | 6.93862E-06 | 0.468 | −0.329 | −0.329 | 3.538 | 7.556 | 0.852 | 0.723 | 0.980 |
| cg27384352 | 7 | CDK5; SLC4A2 | −5.089 | 8.15584E-06 | 0.496 | −0.304 | −0.304 | 4.048 | 8.154 | 0.815 | 0.673 | 0.957 |
| cg06159486 | 10 | CACNB2 | −5.088 | 8.16641E-06 | 0.390 | −0.409 | −0.409 | 2.363 | 6.060 | 0.750 | 0.589 | 0.911 |
| cg26082690 | 10 | KIAA1279 | −4.709 | 1.95375E-05 | 0.430 | −0.366 | −0.366 | 2.735 | 6.353 | 0.778 | 0.624 | 0.931 |
| cg01307939 | 7 | TMEM130 | −4.641 | 2.28342E-05 | 0.242 | −0.617 | −0.617 | 1.012 | 4.187 | 0.787 | 0.636 | 0.938 |
| cg07106633 | 8 | FABP5 | −4.516 | 3.04945E-05 | 0.466 | −0.331 | −0.331 | 3.168 | 6.795 | 0.753 | 0.593 | 0.913 |
| ch.15.814613R | 15 | MYO1E | −4.488 | 3.25211E-05 | 0.457 | −0.340 | −0.340 | 3.014 | 6.593 | 0.748 | 0.587 | 0.910 |
| cg16709232 | 17 | KIF19 | −4.440 | 3.62932E-05 | 0.471 | −0.327 | −0.327 | 3.206 | 6.806 | 0.818 | 0.677 | 0.959 |
| cg18507129 | 3 | CHST2 | −4.408 | 3.90766E-05 | 0.481 | −0.318 | −0.318 | 3.353 | 6.971 | 0.750 | 0.589 | 0.911 |
| cg13565152 | 9 | HINT2 | 4.275 | 5.30759E-05 | 2.072 | 0.316 | 0.316 | 6.513 | 3.144 | 0.815 | 0.673 | 0.957 |
| cg14287565 | 9 | ARPC5L | −4.206 | 6.22169E-05 | 0.463 | −0.335 | −0.335 | 2.955 | 6.386 | 0.765 | 0.608 | 0.923 |
| cg15278646 | 15 | OCA2 | −4.167 | 6.80447E-05 | 0.346 | −0.461 | −0.461 | 1.652 | 4.775 | 0.759 | 0.600 | 0.918 |
| cg00622863 | 9 | PRPF4; CDC26 | −4.060 | 8.7017E-05 | 0.350 | −0.456 | −0.456 | 1.657 | 4.734 | 0.75 | 0.583 | 0.908 |
| cg11284811 | 1 | HENMT1 | −3.659 | 0.000219182 | 0.455 | −0.342 | −0.342 | 2.570 | 5.652 | 0.756 | 0.597 | 0.916 |
| cg25643819 | 6 | HLA-L | −3.565 | 0.000272499 | 0.439 | −0.357 | −0.357 | 2.339 | 5.327 | 0.793 | 0.644 | 0.942 |
| cg19588399 | 1 | SYTL1 | −3.245 | 0.00056829 | 0.393 | −0.405 | −0.405 | 1.760 | 4.476 | 0.784 | 0.632 | 0.936 |
| cg14373499 | 2 | ACTR3 | −3.131 | 0.000740078 | 0.452 | −0.345 | −0.345 | 2.275 | 5.031 | 0.790 | 0.640 | 0.940 |
| cg01185682 | 17 | HLF | −3.002 | 0.000994576 | 0.403 | −0.395 | −0.395 | 1.750 | 4.342 | 0.759 | 0.600 | 0.918 |
| cg16862641 | 6 | COL9A1 | −2.837 | 0.001453983 | 0.481 | −0.318 | −0.318 | 2.436 | 5.066 | 0.747 | 0.585 | 0.909 |
| cg15615160 | 17 | TEKT1 | −2.595 | 0.002541547 | 0.450 | −0.347 | −0.347 | 1.976 | 4.394 | 0.756 | 0.597 | 0.916 |
| cg18786479 | 1 | CD247 | −2.340 | 0.004573041 | 0.487 | −0.313 | −0.313 | 2.191 | 4.502 | 0.861 | 0.737 | 0.986 |
| cg26470340 | 10 | ARHGAP21 | 1.977 | 0.010553676 | 2.070 | 0.316 | 0.316 | 3.871 | 1.870 | 0.752 | 0.591 | 0.912 |
| cg13448968 | 2 | CHPF | −1.492 | 0.032177843 | 0.398 | −0.400 | −0.400 | 1.085 | 2.725 | 0.799 | 0.652 | 0.947 |
| cg07529534 | 8 | ANK1 | −1.468 | 0.034049193 | 0.500 | −0.301 | −0.301 | 1.698 | 3.399 | 0.747 | 0.585 | 0.909 |
| cg23729050 | 2 | KLF7 | −1.393 | 0.040426451 | 0.483 | −0.316 | −0.316 | 1.520 | 3.148 | 0.789 | 0.638 | 0.939 |
| cg25240468 | 2 | CCT4 | −1.376 | 0.042088096 | 0.308 | −0.512 | −0.512 | 0.672 | 2.186 | 0.818 | 0.677 | 0.959 |
| cg08528170 | 19 | MIR24-2 | −13.133 | 7.36464E-14 | 0.412 | −0.386 | −0.386 | 5.568 | 13.530 | 0.843 | 0.711 | 0.975 |
| cg11432250 | 13 | MIR548AS | −16.028 | 9.38502E-17 | 0.484 | −0.315 | −0.315 | 10.114 | 20.893 | 0.824 | 0.685 | 0.963 |
| cg09918657 | 16 | MIR193B | −15.075 | 8.42165E-16 | 0.399 | −0.399 | −0.399 | 5.834 | 14.610 | 0.809 | 0.664 | 0.953 |
| cg04293733 | 1 | MIR137 | −6.989 | 1.02473E-07 | 0.350 | −0.455 | −0.455 | 2.427 | 6.925 | 0.802 | 0.656 | 0.949 |

SUPPLEMENTAL TABLE S4-continued

Expanded epigenomic markers-pediatric concussion kit: Cases vs Controls.

| TargetID | CHR | UCSC_REFGENE_NAME | LOG10p | FDR p-Val | Fold change | Log FC LOG log2(FC) | LOG FC Radha | % Methylation Cases | % Methylation Control | AUC | CL_lower | CL_upper |
|---|---|---|---|---|---|---|---|---|---|---|---|---|
| cg22388260 | 16 | MIR365-1 | −30.418 | 3.81667E-31 | 0.273 | −0.564 | −0.564 | 5.969 | 21.855 | 0.787 | 0.636 | 0.938 |
| cg08528170 | 19 | MIR23A | −13.133 | 7.36464E-14 | 0.412 | −0.386 | −0.386 | 5.568 | 13.530 | 0.843 | 0.711 | 0.975 |
| cg08528170 | 19 | MIR27A | −13.133 | 7.36464E-14 | 0.412 | −0.386 | −0.386 | 5.568 | 13.530 | 0.843 | 0.711 | 0.975 |
| cg24956533 | 15 | LOC145845 | −28.502 | 3.14447E-29 | 0.475 | −0.323 | −0.323 | 16.051 | 33.762 | 0.877 | 0.759 | 0.994 |
| cg14536682 | 3 | LOC339862 | −29.321 | 4.77947E-30 | 0.457 | −0.340 | −0.340 | 14.799 | 32.383 | 0.753 | 0.593 | 0.913 |
| cg23307878 | 10 | LOC105376360 | −29.880 | 1.31813E-30 | 0.450 | −0.347 | −0.347 | 14.710 | 32.683 | 0.765 | 0.608 | 0.923 |
| cg12608247 | 2 | LOC643387 | −13.669 | 2.14417E-14 | 0.478 | −0.321 | −0.321 | 8.447 | 17.678 | 0.765 | 0.608 | 0.923 |
| cg12608247 | 2 | LOC151174 | −13.669 | 2.14417E-14 | 0.478 | −0.321 | −0.321 | 8.447 | 17.678 | 0.765 | 0.608 | 0.923 |
| cg24662666 | 10 | LOC282997 | −30.461 | 3.46333E-31 | 0.325 | −0.488 | −0.488 | 7.573 | 23.298 | 0.787 | 0.636 | 0.938 |
| cg24603047 | 2 | LOC101927156 | −30.083 | 8.26506E-31 | 0.279 | −0.554 | −0.554 | 6.652 | 23.830 | 0.818 | 0.677 | 0.959 |
| cg05908371 | 20 | LOC284798 | −13.384 | 4.12897E-14 | 0.439 | −0.357 | −0.357 | 6.617 | 15.071 | 0.784 | 0.632 | 0.936 |
| cg07044757 | 15 | LOC145845 | −16.434 | 3.68152E-17 | 0.401 | −0.397 | −0.397 | 6.325 | 15.794 | 0.855 | 0.728 | 0.982 |
| cg00037681 | 12 | LOC100233209 | −29.967 | 1.07984E-30 | 0.253 | −0.597 | −0.597 | 5.962 | 23.595 | 0.772 | 0.616 | 0.927 |
| cg20585676 | 2 | LOC100132215 | −24.888 | 1.29385E-25 | 0.326 | −0.486 | −0.486 | 5.862 | 17.966 | 0.756 | 0.597 | 0.916 |
| cg12309653 | 15 | LOC145845 | −30.647 | 2.25346E-31 | 0.280 | −0.552 | −0.552 | 5.848 | 20.868 | 0.784 | 0.632 | 0.936 |
| cg26668608 | 2 | LOC440839 | −30.367 | 4.29128E-31 | 0.250 | −0.602 | −0.602 | 5.355 | 21.435 | 0.778 | 0.624 | 0.931 |
| cg11860632 | 1 | LOC100506022 | −30.268 | 5.40048E-31 | 0.224 | −0.650 | −0.650 | 4.754 | 21.216 | 0.753 | 0.593 | 0.913 |
| cg00764796 | 16 | LOC100134368 | −14.715 | 1.92945E-15 | 0.362 | −0.441 | −0.441 | 4.625 | 12.771 | 0.762 | 0.604 | 0.920 |
| cg23543318 | 4 | LOC100130872 | −30.413 | 3.86033E-31 | 0.260 | −0.585 | −0.585 | 4.602 | 17.691 | 0.762 | 0.604 | 0.920 |
| cg11724135 | 20 | LOC284798 | −18.625 | 2.36872E-19 | 0.314 | −0.503 | −0.503 | 4.239 | 13.508 | 0.765 | 0.608 | 0.923 |
| cg12393318 | 5 | LOC645323 | −21.419 | 3.8141E-22 | 0.275 | −0.561 | −0.561 | 3.750 | 13.644 | 0.806 | 0.660 | 0.951 |
| cg11252953 | 17 | C17orf101 | −30.323 | 4.75647E-31 | 0.320 | −0.494 | −0.494 | 7.660 | 23.911 | 0.747 | 0.585 | 0.909 |
| cg03081691 | 1 | C1orf55 | −31.046 | 8.99759E-32 | 0.271 | −0.567 | −0.567 | 5.036 | 18.579 | 0.864 | 0.741 | 0.987 |
| cg27166718 | 6 | C6orf204 | −27.897 | 1.2683E-28 | 0.422 | −0.374 | −0.374 | 11.581 | 27.410 | 0.784 | 0.632 | 0.936 |
| cg11337945 | 5 | C5orf38 | −8.413 | 3.85929E-09 | 0.436 | −0.361 | −0.361 | 4.378 | 10.047 | 0.778 | 0.624 | 0.931 |
| cg10883375 | 14 | C14orf43 | −29.801 | 1.58015E-30 | 0.311 | −0.507 | −0.507 | 6.265 | 20.145 | 0.775 | 0.620 | 0.929 |
| cg10050900 | 1 | C1orf200 | −13.778 | 1.6683E-14 | 0.402 | −0.396 | −0.396 | 5.486 | 13.653 | 0.765 | 0.608 | 0.923 |
| cg03846926 | 10 | C10orf140 | −4.828 | 1.48757E-05 | 0.439 | −0.357 | −0.357 | 2.910 | 6.623 | 0.759 | 0.600 | 0.918 |
| cg14826711 | 1 | C1orf114 | −15.637 | 2.3089E-16 | 0.366 | −0.437 | −0.437 | 4.958 | 13.563 | 0.756 | 0.597 | 0.916 |
| cg21542248 | 14 | C14orf23 | −8.390 | 4.07572E-09 | 0.331 | −0.480 | −0.480 | 2.503 | 7.561 | 0.756 | 0.597 | 0.916 |
| cg06499647 | 2 | C2orf40 | −5.022 | 9.50635E-06 | 0.472 | −0.326 | −0.326 | 3.536 | 7.489 | 0.750 | 0.589 | 0.911 |
| cg12860686 | 5 | C5orf38 | −17.605 | 2.48351E-18 | 0.335 | −0.475 | −0.475 | 4.590 | 13.694 | 0.775 | 0.620 | 0.929 |
| cg14025053 | 8 | C8orf56 | −17.277 | 5.28266E-18 | 0.385 | −0.415 | −0.415 | 6.025 | 15.664 | 0.750 | 0.589 | 0.911 |

Metabolomics Data.

The present disclosure describes the use of metabolomics for diagnosing TBI. Metabolomics is the study of chemical processes involving metabolites, which are small molecule intermediates and products of cellular metabolism. The method described herein includes measuring metabolite levels in a biologic sample from a patient using separation methods such as liquid chromatography, high performance liquid chromatography, gas chromatography, capillary electrophoresis, and detection methods such as nuclear magnetic resonance (NMR) and mass spectrometry (MS) including direct flow MS or a combination thereof to identify and quantify the metabolites in the biological samples. While a total of 18 cases and 18 controls underwent metabolomic analysis, combined analysis was performed in an overlapping subgroup of 17 patients with concussion and 18 controls that also underwent epigenomic analysis and constitute the basis for the epigenomic analyses previously reported. Subsequently the performance of epigenomic, metabolomic, clinical and demographic analyses individually and combined were reported for these 17 concussion cases and 18 controls (Tables 4-8).

Examples of biological samples include tissue samples, body fluids, skin, hair, follicles/roots, and mucous membranes for methylation analyses. Examples of body fluids for metabolomic analyses include blood, saliva, urine, sweat, tear, breath condensate, or blood. Examples of mucous membranes include cheek scrapings, buccal scrapings, or scrapings from the tongue.

Table 3 provide the list of metabolites (small molecules). In embodiments, metabolites include one of more of C7-DC, PC aa C260, PC aa C322, PC aa C342, PC aa 362, PC aa 382, PC aa 384, asparagine, tyrosine, alpha-AAA, spermidine, D-glucose, hypoxanthine, pyroglutamic acid, or isopropyl alcohol. They were found to be more effective and statistically significant in predicting TBI, especially in combination with epigenomic data. Table 3 also provides other metabolites that contribute to the prediction of TBI, especially in combination with epigenomic data. The performance of metabolomic markers individually or combined with other predictive markers (epigenomic, demographic and clinical) for the prediction of mTBI are displayed in Tables 4-8.

In embodiments, the metabolomic data and the epigenomic data provided herein can be combined or used together to diagnose TBI. The combination of the metabolomic data and epigenomic data provide accurate detection of TBI.

Microarray.

Differential methylation can be analyzed using a microarray system. Nucleic acids can be linked to chips, such as microchips. See, for example, U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138. Binding to nucleic acids on microarrays can be detected by scanning the microarray with a variety of laser or charge coupled device (CCD)-based scanners, and extracting features with software packages, for example, Imagene (Biodiscovery, Hawthorne, CA), Feature Extraction Software (Agilent), Scanalyze (Eisen, M. 1999. SCANALYZE User Manual; Stanford Univ., Stanford, Calif. Ver 2.3.2.), or GenePix (Axon Instruments). A full panel of loci would include the 412 CpG sites listed in Table 2 that have been shown individually to be potentially clinically useful tests AUC≤0.75. An extended microarray panel consisting of multiple (as opposed to a single) significant CpG locus per gene would further enhance predictive ability and is shown in Supplemental Table 4 and is included in this study. This expanded panel includes more than one CpG marker per gene (in contrast with Table 2 that is limited to the single best performing Cpg locus per gene). The expanded panel for use in a microarray kit can be expected to further improve predictive accuracy using epigenomic markers.

Kits.

Kits for predicting and diagnosing TBI based on methylation of CpG loci on nucleic acids are described. The kits can include the components for extracting nucleic acids including DNA and RNA including mRNA from the biological sample, the components of a microarray system, and/or for analysis of the differentially methylated genomic sites.

Artificial Intelligence (AI).

One or more AI algorithms can be used in combination with the methods described herein to improve the accuracy for predicting and/or diagnosing TBI. Representative examples of AI algorithms include Random Forest (RF), Support Vector Machine (SVM), Linear Discriminant Analysis (LDA), Prediction of Analysis for Microarrays (PAM), Generalized Linear Model (GLM), and deep learning (DL).

Random Forest (RF) is a supervised classification algorithm used for regression, classification and other tasks. Multiple decision tree predictive models are randomly generated in the training phase and the mode of the classes and mean prediction of the individual trees are generated as outputs. There is a direct relationship between the number of trees in the forest and the results it can get the larger the number of trees, the more accurate the result. The difference between Random Forest algorithm and the decision tree algorithm is that in Random Forest, the processes of finding the root node and splitting the feature nodes will run randomly. The decision tree is a decision support tool that uses a tree-like graph to show the possible consequences. If one inputs a training dataset with targets and features into the decision tree, it will formulate a set of rules. Overfitting is one critical problem that may make the results worse in decision trees, but for Random Forest algorithm, if there are enough trees in the forest, the classifier won't overfit the model. Another advantage is the classifier of Random Forest can handle missing values, and the last advantage is that the Random Forest classifier can be modeled for categorical values.

Support vector machine (SVM) is primarily a classifier method that performs classification tasks by constructing hyperplanes in a multidimensional space that separates cases of different class labels. SVM supports both regression and classification tasks and can handle multiple continuous and categorical variables. Suppose some given data points each belong to one of two classes, and the goal is to decide which class a new data point will be in. In the case of support vector machines, a data point is viewed as a p-dimensional vector (a list of p numbers), and we want to know whether we can separate such points with a (p-1)-dimensional hyperplane. This is called a linear classifier. There are many hyperplanes that might classify the data. One reasonable choice as the best hyperplane is the one that represents the largest separation, or margin, between the two classes. We choose the hyperplane so that the distance from it to the nearest data point on each side is maximized. If such a hyperplane exists, it is known as the maximum-margin hyperplane and the linear classifier it defines is known as a maximum margin classifier or equivalently, the perceptron of optimal stability.

Linear Discriminant Analysis (LDA) is a classification method originally developed in 1936 by R. A. Fisher. It is simple, mathematically robust and often produces models whose accuracy is as good as more complex methods. LDA is based upon the concept of searching for a linear combination of variables (predictors) that best separates two classes (targets). It is closely related to analysis of variance (ANOVA) and regression analysis, which also attempt to express one dependent variable as a linear combination of other features or measurements.

Prediction Analysis for Microarrays (PAM) is a statistical technique for class prediction from gene expression data using nearest shrunken centroids. This method identifies the subsets of genes that best characterize each class.

Generalized Linear Models (GLMs) are a broad class of models that include linear regression, ANOVA, Poisson regression, log-linear models etc. But there are some limitations of GLMs, such as, linear function, e.g. can have only a linear predictor in the systematic component, and responses must be independent.

Generally classical machine learning techniques make predictions directly from a set of features that have been pre-specified by the user. However, representation learnrning techniques transform features into some intermediate representation prior to mapping them to final predictions. Deep Learnrming (DL) is a form of representation learning that uses multiple transformation steps to create very complex features. DL is widely applied in patter recognition, image processing, computer vision, and recently in bioinformatics. DL is categorized into feed-forward artificial neural networks (ANNs), which uses more than one hidden layer (y) that connects the input (x) and output layer (z) via a weight (W) matrix. The weight matrix W which is expected to minimize the difference between the input layer (x) and the output layer (z) is considered as the best one and chosen by the system to get the best results.

Treatment.

Treatment for TBI must begin as soon as possible. In embodiments, it should begin immediately following injury and/or diagnosis of TBI. The latest guidelines for treatment of mTBI in children was recently published by the CDC (Lumba-Brown A et al. *Centers for Disease Control and Prevention guideline on the Diagnosis and Management of mild traumatic brain injury among children, JAMA Pediatr* doi:10.1001/jamapediatrics 2018.2853). A summary of this document is presented below.

Recommendations Related to Management and Treatment.

The CDC has put forth recommendations to serve as guidelines and best practices for management and treatment of mTBI. What follows is a summary of those published guidelines. Key guideline components include patient and family education, reassurance, psychosocial and emotional support, cognitive and physical rest and aerobic treatment, post traumatic headache management and treatment, cognitive impairment, vestibulo-oculomotor dysfunction, sleep issues, and continued monitoring upon return to school.

Patient/Family Education and Reassurance.

When caring for a pediatric patient with mTBI the family and patient should be informed as to the injury and post-concussive symptoms, provided with anticipatory guidance as to treatment and recovery; for example, warning signs of more severe injury; information about nature of injury and the expected course including symptoms and timing of recovery; ongoing monitoring of symptoms; how to prevent/minimize of further injury; a plan for resumption of cognitive and physical activity and discussion of rest; issues of timing of returning to play and resumption of school work; and follow up instructions.

Patient/Cognitive/Physical Rest and Aerobic Treatment.

In close consultation with the clinician, a plan for gradual resumption of activity should be put in place if the patient is symptom free at rest. Physical activity that doesn't exacerbate symptoms has been shown to reduce post-concussive symptoms. However, it is worth noting that physical rest and reduced physical activity immediately after a mTBI promotes a more rapid recovery. Children with chronic sleep problems post mTBI should be referred to a sleep specialist. Inadequate sleep adversely affects medical conditions such as mTBI.

Chronic headaches may occur after a mTBI and the cause may be multifactorial. Monitoring of headaches is vital as evidence supports the presence of a more severe form of mTBI in a child with progressively more severe headache. Neuroimaging should be used to evaluate progressively worsening headache. While concerns about radiation exposure to a child is always legitimate, in these circumstances the risk of the TBI is felt to exceed the risk of ionizing radiation. The guidelines advised against administering a 3% hypertonic saline solution to children with mTBI for headache symptoms outside of a research setting.

Normal vestibulo-oculomotor reflex (VOR) function is vital for normal activities of daily living. Damage to the (VOR) may manifest as dizziness, blurry vision, problems maintaining balance with head movements. Vestibular rehabilitation may be of use in treating these symptoms although the evidence is limited.

Cognitive impairment or the disruption of cognitive processing may be direct result of brain injury or may be a secondary effect of other symptoms i.e. headache and fatigue. In this event nueropsychological evaluations are recommended to determine management.

Psychosocial/Emotional Support.

The health care professional should assess the availability, type of social support (emotional, informational, instrumental and appraisal) needed by the patient. Social support has been shown to promote recovery in patients with TBI, especially for those with cognitive changes post mTBI.

Timing of return to school is a crucial consideration in cases children who have suffered from concussion. Generally, the guidelines for the timing of return to school post mTBI require a team approach to decision-making which should include the family, patient, healthcare professionals, and school teams. Post-concussion symptoms, and other issues that may be interfering with academic progress should be identified and monitored. The necessity for appropriate support and modifications to the academic workload should be addressed. In the event of prolonged symptoms, the patient should be referred to healthcare professional/pediatrician who specializes in mTBI.

Posttraumatic Headache Management/Treatment.

Children with worsening or severe headache should undergo CT imaging. Non-opiod (e.g. ibuprofen, acetaminophen) to children with severe post-concussion headache. Discussions of the risk of these agents and also the possibility of rebound headaches after discontinuation from medication Vestibulo-Oculomotor Dysfunction Management/Treatment.

Such individuals should be referred for specialist evaluation. Evidence suggest that such findings may correlate with longer duration of post-traumatic symptoms. Physical therapy may improve symptoms such as dizziness.

Sleep Management/Treatment.

Counseling on sleep related issues and how to achieve proper amounts of sleep is of paramount importance. Maintenance of a proper amount of sleep and addressing problems of disruptive sleep may require referral to a sleep specialist.

Cognitive Impairment Management/Treatment.

Cognitive impairment affecting attention, memory, learning, response speed and executive function can develop after brain trauma. These can also be a consequence of headache, fatigue etc. A search should be made to identify the etiology of cognitive dysfunction. Consultation for neuropsychological testing might be appropriate.

Summary.

Biomarker detection of mTBI/concussion as described herein can lead to the early and accurate diagnosis and thus facilitate the management objectives outlined by the CDC. Given the evidence that a significant percentage even a majority of concussion cases remain undiagnosed, accurate biomarkers is a critical necessary complement to any effective treatment strategy.

Methods disclosed herein for include predicting, diagnosing, and/or treating patients which includes mammals, for example humans. Subjects or patients in need of (in need thereof) such predicting, diagnosing, and/or treating are subjects that may have TBI and need to be diagnosed and treated.

The following exemplary embodiments and examples illustrate exemplary methods provided herein. These exemplary embodiments and examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

EXEMPLARY EMBODIMENTS

The following are exemplary embodiments:
1. A method for diagnosing traumatic brain injury (TBI), wherein the method includes:
    assaying a biological sample including nucleic acids to determine a frequency or percentage methylation of cytosine at one or more loci throughout genome; and comparing the cytosine methylation level of the sample to one or more controls.
2. The method of embodiment 1, wherein the one or more controls include a biological sample from normal patients (patients without TBI) or a sample from patients diagnosed with TBI.
3. The method of embodiment 1 or 2, wherein the method further includes obtaining a biological sample from a patient in need thereof.
4. The method of any one of embodiments 1-3, wherein the method further includes extracting DNA from the biological sample.
5. The method of any one of embodiments 1-4, wherein the TBI includes chronic traumatic encephalopathy (CTE), recurrent TBI, or mild TBI (mTBI).
6. The method of any one of embodiments 1-5, wherein the method further comprises calculating the patients risk of TBI based on the cytosine methylation level at different sites throughout the genome.
7. The method of any one of embodiments 1-6, wherein the biological sample includes body fluid or a tissue obtained from the patient.
8. The method of any one of embodiments 1-7, wherein the biological sample includes blood, plasma, serum, urine, buccal swab, saliva, sputum, urine, tear, sweat, or hair.
9. The method of any one of embodiments 1-8, where in the percentage methylation of cytosines are determined for different combinations of loci to calculate the probability of TBI in an individual.
10. The method of any one of embodiments 1-8, wherein the patient is greater than 19 years old or wherein the patient is a pediatric patient.
11. The method of any one of embodiments 1-9, wherein the patient is a pediatric patient less than 18 years old, less than 15 years old, less than 12 years old, less than 9 years old, less than 6 years old, less than 3 years, or less than one year old.
12. The method of any one of embodiments 1-11, wherein the nucleic acids include cellular nucleic acids or wherein the nucleic acids include cell free nucleic acids.
13. The method of any one of embodiments 1-12, wherein the nucleic acids include DNA or RNA.
14. The method of any one of embodiments 1-13, wherein the RNA includes mRNA.
15. The method of any one of embodiments 1-14, wherein the nucleic acids includes cell free DNA cell free extracted from body fluid including blood, CSF and urine.
16. The method of any one of embodiments 1-15, wherein the one or more loci include at least two genomic loci.
17. The method of any one of embodiments 1-16, wherein the one or more loci include the loci from Table 2, Supplemental Table S1, Supplemental Table S2, Supplemental Table S3, Supplemental S4, Table 4, Table 5, Table 6, Table 7, or Table 8.
18. The method of any one of embodiments 1-17, wherein the one or more loci include the loci from Table 2, Supplemental Table S1, Supplemental Table S2, Supplemental Table S3, Supplemental S4, Table 4, Table 5, Table 6, Table 7, or Table 8 and wherein the one or more loci include an AUC of 0.80 or greater, 0.85 or greater, 0.90 or greater, or 0.95 or greater.
19. The method of any one of embodiments 1-18, wherein the one or more loci include two, three, four, five, six, seven, eight, nine, or 10 loci.
20. The method of any one of embodiments 1-19, wherein the assay is a bisulfite-based methylation assay or a whole genome methylation assay.
21. The method of any one of embodiments 1-20, wherein measurement of the frequency or percentage methylation of cytosine nucleotides includes using single gene or whole genome sequencing techniques.
22. The method of any one of embodiments 1-21, wherein the sample is obtained and stored for purposes of pathological examination.
23. The method of any one of embodiments 1-22, wherein the sample is stored as slides, tissue blocks, or frozen.
24. A method of any one of embodiments 1-23, wherein the method includes assaying proteins encoded by the nucleic acids including the differentially methylated CpG loci
25. A method of any one of embodiments 1-24, wherein the method further comprises assaying mRNA including the differentially methylated CpG loci.
26. A method of diagnosing TBI including assaying expression of one or more RNA transcripts in a biological sample from a patient, wherein the one or more RNA transcripts include transcripts that are regulated by methylation of a CpG locus that is differentially methylated in TBI patients; and comparing the cytosine methylation level of the patient to a control.

27. A method of diagnosing TBI including assaying the expression of one or more proteins in a biological sample from a patient, wherein the one or more proteins include proteins with expression regulated by methylation of a CpG locus that is differentially methylated in TBI patients; and comparing the cytosine methylation level of the patient to a control.

28. The method of any one of embodiments 1-27, wherein the method further includes using an mRNA genome-wide chip for assaying.

29. A method of diagnosing TBI of any one of embodiments 1-28, wherein the method further includes using metabolomic data obtained from the patient.

30. The method of any one of embodiments 1-29, wherein the method includes using the one or more metabolomic markers shown in Table 3.

31. The method of embodiment 30, wherein the one or more metabolomic markers include C7-DC, PC aa C260, PC aa C322, PC aa C342, PC aa 362, PC aa 382, PC aa 384, asparagine, tyrosine, alpha-AAA, spermidine, D-glucose, hypoxanthine, pyroglutamic acid, or isopropyl alcohol.

32. A method of diagnosing TBI in a patient, wherein the method comprises obtaining a biological sample from the patient and detecting and measuring one or more metabolomic markers in the sample to determine whether the patient has TBI.

33. The method of embodiment 32, wherein the detected and measured metabolomic markers include one or more of the small molecules shown in Table 3.

34. The method of embodiment 32 or 33, wherein the one or more metabolomic markers include C7-DC, PC aa C260, PC aa C322, PC aa C342, PC aa 362, PC aa 382, PC aa 384, asparagine, tyrosine, alpha-AAA, spermidine, D-glucose, hypoxanthine, pyroglutamic acid, or isopropyl alcohol.

35. The method of any one of embodiments 1-34, wherein epigenomic biomarkers are combined with metabolomic markers and or existing clinical assessment tools and clinical findings for improved accuracy in predicting and/or diagnosing TBI.

36. The method of any one of embodiments 1-35, wherein the method further includes using artificial intelligence techniques.

37. The method of any one of embodiments 1-36, wherein the method further includes using artificial intelligence and wherein using artificial intelligence includes using one or more of the following machine learning algorithms: Random Forest (RF), Support Vector Machine (SVM), Linear Discriminant Analysis (LDA), Prediction of Analysis for Microarrays (PAM), Generalized Linear Model (GLM), or deep learning (DL).

38. The method of any one of embodiments 1-37, wherein the method further includes treating the patient for TBI.

39. The method of any one of embodiments 1-38, wherein the method further includes treating the patient for TBI and wherein treating the patient includes one or more of cognitive and physical rest and aerobic treatment, post traumatic headache management and treatment, cognitive impairment treatment, vestibulo-oculomotor dysfunction treatment, sleep deprivation treatment, or continued monitoring of the patient.

40. A kit for predicting TBI of any one of embodiments 1-39, wherein the kit includes a microarray for identifying one or more methylated CpG loci shown in Table 2, Supplemental Table S1, Supplemental Table S2, Supplemental Table S3, Supplemental S4, Table 4, Table 5, Table 6, Table 7, or Table 8 and other components.

41. The kit of embodiment 40, wherein the kit further includes a microarray for identifying one or more methylated CpG loci of miRNAs shown in Supplemental Table S1, ORFs shown in Supplemental Table S2, or LOC genes of Supplemental Table S3.

42. The kit of embodiment 40 or 41, wherein the kit further includes an array for identifying one or more proteins encoded by the one or more nucleic acids including the differentiated loci.

EXAMPLES

Example 1

The purpose of this study was to examine DNA methylation changes in blood leucocytes to clarify the molecular mechanisms of concussion in children and to develop potential non-invasive molecular biomarkers for the detection of pediatric concussion. The age of study patients ranged from infancy </=to 1 year of age up to <15 years. A further objective was also to look at epigenomics, metabolomics and clinical predictors in different combination for the detection of concussion using Deep Learning (DL) and other Artificial Intelligence (AI) techniques. The combination of epigenomics and metabolomics have not been previously reported for the prediction of concussion.

Materials and Methods. Study Population and Sample Collection.

This prospective case-control was conducted at the pediatric emergency center of Dokuz Eylul University School of Medicine. The study was approved by the Ethics Committee of Ankara Children's Hematology and Oncology Hospital, Ankara, Turkey. After written and verbal consents were obtained from the parents, subjects were enrolled in the study and used for metabolomic and epigenomic analyses. Of these 18 cases and 18 controls were used for the epigenomic analysis and 17 cases and 18 controls with complete clinical, epigenomic and metabolomic data were used for the combined metabolomic and epigenomic analysis. The case children had closed head trauma and a subsequent CT evaluation.

The study cohort were seen in the pediatric clinic at Dokuz Eylul University School of Medicine Hospital, Ankara, Turkey. A Glasgow Coma Score (GCS) between 13-15 was used to define mTBI or concussion. Genomic DNA from whole blood was isolated using Puregene DNA Purification kits (Gentra Systems® MN, USA) according to manufacturer's protocols. The blood samples were taken from the subjects immediately at the medical visit once the clinical diagnosis was made. All subjects were of Turkish origin and gave written informed consent prior to participation in the study. As noted, IRB approval was provided by the Ethics Committee of Ankara Children's Hematology and Oncology Hospital, Ankara, Turkey and the Human Investigation Committee of Research Institute, WIlliam Beaumont Hospital, Royal Oak, MI, USA {IRB).

Epigenomic Analysis.

Bisulfite conversion genomic DNA and Illumina Human-Methylation450 analysis. Genomic DNA (500 ng) was bisulfite converted using the EZ DNA Methylation-Direct Kit (Zymo Research, Orange, CA). Genome-wide DNA methylation analysis was done using the HumanMetl1ylation450 assay (Illumine, Inc. San Diego, CA, USA) according the manufacturer's guidance. The assay assesses 450,000 CpG loci throughout the genome and covers the enhancer regions, gene bodies, promoters and CpG islands at a single-nucleotide resolution. Fluorescently-stained BeadChips were imaged by the Illumina iScan. DNA methylation data were processed using GenomeStudio software (Ver. 2.0.3; Illumine, Inc.) applying the default settings. Data were analyzed with Illumina's Genome Studio methylation analysis package program. Detailed methodology has been previously published [20].

Single nucleotide polymorphisms (SNPs) are the most common type of genetic variation. Around 25% of Illumina 450K array probes are associated with SNPs [21]. Methylation levels of a specific locus with SNPs near or within the probe sequence may influence corresponding methylated probes [22]. Therefore, in order to avoid this potential confounding, and as suggested by Illumina, SNPs near or within the probe sequence or in the target CpG dinucleotide (i.e., within 10 bp of the CpG site) were excluded from further analysis [21,23, 24]. To avoid potential bias related to significant CpG sites on sex chromosomes, CpG probes on the X and Y chromosomes were removed from the analysis to avoid gender-specific methylation bias.

Statistical Analysis.

Methylation levels for all autosomal chromosome CpG sites were calculated as n-values of the individual CpG site. Data were normalized using the Controls Normalization Method. To avoid potential experimental confounding, various statistical modeling were used. Methylation alteration levels were computed by comparing the β-values per individual nucleotide at each CpG site between concussion cases and controls. The p-value for methylation differences between case and normal groups at each locus was calculated [25]. Filtering criteria for p-values was set at <0.05 and <0.01 to identify the most differentiating cytosines. Subsequently, the p-values were adjusted for multiple hypotheses testing and were calculated using the Benjamini-Hochberg correction for False Discovery Rate. Receiver Operating Characteristic (ROC) and Area Under Curve (AUC) were calculated in 'R' computer program using built-in packages and functions (v1.6.0 R package v3.2.2). This was used for calculating AUC for the individual CpG loci.

Fold changes in methylation variation were achieved by dividing the mean n-value for the probes in each CpG site by that of the normal controls. Absolute percentage difference in methylation at each CpG locus was also calculated. Based on multiple pre-set cutoff criteria, the most significantly differentiated CpG sites were selected using the criteria of 22.0-fold increase and/or 22.0-fold decrease with Benjamini-Hochberg False Discovery Rate (FDR) p<0.01. When multiple significantly differentially methylated CpG sites were present in a single gene, selection of the CpG was resolved by considering the targets with the highest fold-change ranking and the lowest p-value. After this filtering, a threshold was set to select ROC curves based on sensitivity plotted against specificity, using multiple different n-value threshold at each CPG locus to calculate paired sensitivity and specificity values and ultimately AUC for mTBI prediction. Individual markers with AUC z0.75, significant 95% CI and FDR p-value <0.0001 were considered potentially clinically significant predictors (by themselves) of pediatric concussion and further used in the pathway analysis.

Bioinformatics Analysis.

Integrated gene ontology and pathway analysis was performed using Chilibot (www.chilibot.net) database, with gene names and keywords of interest. Ingenuity Pathway Analysis (Ingenuity Systems, www.ingenuity.com) was performed for differentially methylated genes at an FDR p-value <0.0001 to investigate potential molecular functions of the candidate biomarkers. Only genes with Entrez identifiers were used in the Pathway analysis. Biological pathways that were statistically enriched, over-represented established pathways, and molecular processes were identified.

Quantitative Pyrosequencing.

To further validate the results, and to confirm that the CHIP hybridization results are not artifacts and these CpG sites are indeed robust, we tested bisulfite-converted genomic DNA by quantitative pyrosequencing analysis. A total of 25 CpG sites were selected for validation of variable methylation by pyrosequencing. One candidate site in each of 25 genes was selected and all were in the body of the gene. DNA methylation variations were compared with the data obtained from conventional quantitative pyrosequencing. Detailed methodology was published previously [20].

Metabolomic Analysis.

Both $^1$H-NMR (proton-based Nuclear Magnetic Resonance) and Liquid chromatography/Mass spectrometry/ Mass Spectrometry (LC-MS-MS) metabolomic analysis were performed on the serum.

$^1$H-NMR Sample Preparation.

Prior to NMR analysis 300 μL of the serum samples were filtered through 3-kDa cut-off centrifuge filter units at 13,000 g for 30 min at 4° C. (Amicon Microcon YM-3; Sigma-Aldrich, St. Louis, MO). To 200 μl of the filtrate 25 μl of $D_2O$ and 21 μl of 1.75 $K_2HPO_4$ buffer (pH 7.2) containing 5.84 mM 2-choloro pyrimidine-5-carboxylic acid and 5.8333 mM of DSS-De (disodium-2, 2-dimethyl-2-silceptentane-5-sulphonate) were added (final pH was 7.27±0.07 for all samples). 200 μl of the solution was transferred to 3 mm NMR tubes for analysis.

$^1$H-NMR Analysis.

Samples were analyzed in a randomized order and maintained at 4° C. using the state-of-the-art SampleJet™ (Bruker, Cambridge, MA) sample changer. Prior to analysis by NMR, samples were heated to room temperature over 3 min before being transferred to the magnet. All $^1$H-NMR experiments were recorded at 300.0 (±0.05) K on a Bruker Avance III HD 600 MHz spectrometer (Bruker-Biospin, USA) operating at 600.13 MHz equipped with a 5 mm TCI cryoprobe using the pulse sequence as reported by Ravanbaksh et al., (2015)$^9$. 256 transients were acquired across 64k data points with a spectral with of 11.964 Hz and inter-pulse delay of 5.4 s between each transient. The free induction decay signal was zero filled to 128k points prior to Fourier transformation and 0.1 Hz of line broadening was applied. All peaks were referenced to the singlet produced by the internal standard DSS-De (50.00) which was also used for the accurate quantification of all metabolites. All spectra were processed and analyzed using the Chenomx NMR Suite Professional Software package (v8.1, Chenomx Inc, Edmonton, AB).

Mass Spectra Profiling.

Targeted analysis of metabolites were carried out using p180 Absolute IDQ kit (Biocrates Life Sciences AG, Innsbruk, Austria) with a TQ-S mass spectrometer coupled to a Acquity I Class ultra-pressure liquid chromatography (UPLC) system (Waters Technologies Corporation, Milford, MA, USA). This system enables the accurate quantification of up to 180 endogenous metabolites including amino acids, acylcarnitines, biogenic amines, glycerophospholipids, sphingolipids, and sugars. Serum samples were analyzed using the protocol described in AbolutelDQ manual. Briefly, serum samples were thawed on ice, vortexed and centrifuged at 4° C. for 5 minutes at 2750 g. 10 µl of blank, 3 zero samples, 7 calibration standards and 3 quality control samples were LDAded onto the filters in the upper 96 well plate and dried under a constant stream of nitrogen using a 96 well plate positive pressure manifold (Waters Technologies Corporation, Milford, MA, USA). Subsequently, 50 µl of the derivatization solution phenylisothiocyanate was added to each well and left at room temperature for 20 minutes. The plate was dried under nitrogen for 60 minutes, followed by the addition of 300 µl of methanol containing 5 mM ammonium acetate and shaking for 30 minutes. The extracts were filtered to a collection plate under nitrogen in the pressure manifold. The eluates were diluted with water for analysis of metabolites using UPLC-MS and diluted with running solvent for analysis by flow injection analysis (FIA)-MS. Sample registration, metabolite concentrations calculations and data export were undertaken using the Biocrates MetlDQ software.

Clinical and demographic information including the SAC (Standard Assessment of Concussion tool) score were utilized.

Artificial Intelligence (AI) Analysis.

A representative set of six artificial intelligence algorithms which have been applied for problems of data classification in bioinformatics field were selected. They include Random Forest (RF), Support Vector Machine (SVM), Linear Discriminant Analysis (LDA), Prediction of Analysis for Microarrays (PAM), Generalized Linear Model (GLM), and deep learning (DL).

Software Packages Utilized.

The H2O R package (https://cran.r-project.org/web/packages/h2o/h2o.pdf, Author The H2O.ai team Maintainer Tom Kraljevic <tomk@Oxdata.com>) was used to tune the parameters of the DL model.

To get the optimal predictions for the Artificial Intelligence algorithms other than DL, the caret R package (https://cran.r-project.org/web/packages/careVcaret.pdf, Maintainer Max Kuhn <mxkuhn@gmail.com>, Dec. 10, 2017) was used to tune the parameters in the models.

The variable importance functions varimp in h2o and var/mp in caret R packages were used to rank the models features in each of the predictive algorithms.

The pROC R package was used to compute area under the curve (AUC) of a receiver-operating characteristic (ROC) curve to assess the overall performance of the models.

Modeling and Evaluation. The objective of this study is to determine the performance of different categories of markers for the prediction of concussion using different Artificial Intelligence techniques. There are five marker combinations: 1. Epigenomic markers by themselves; 2. Combined epigenomic and clinical markers; 3. Combined epigenomic, and metabolic markers; 4. Combined epigenomic, clinical and metabolic markers; and 5. Combination of metabolomic and clinical markers.

The top markers from each of the groups listed above were identified and ranked using each of the 6 Artificial Intelligence techniques: Random Forest, Support Vector Machine, Linear Discriminant Analysis, Prediction Analysis for microarrays, Generalized Linear Model, and Deep Learning.

The data was split into 80% training set and 20% testing set. While dealing with a small size of data in the machine learning applications, the 80/20 split is a commonly used one. A 10-fold cross validation was performed on the 80% training data during the model construction process and tested the model on the hold out 20% of data. To avoid sampling bias, the above splitting process was repeated ten times and calculated the average AUC on the 10 hold out test sets. In addition to AUC, sensitivity, specificity, and 95% confidence intervals were calculated for the test sets.

Feature predictors were estimated using a model-based approach. In other words, a feature was considered important if it contributed to the model performance.

Artificial Intelligence Analysis.

For the prediction of concussion, the top 390 most accurate individual epigenomic markers/genes, ranked based on the area under the receiver operating characteristics curve (AUC) and the false discovery rate p-values, were evaluated for the prediction of mTBI using AI, Machine Learning techniques. DL and five other commonly used artificial intelligence methods: RF, SVM, LDA, PAM, and GLM to identify the best combination of predictive markers. The average AUCs, sensitivity and specificity values calculated on the hold out test or validation sets were reported. Next, the same process was repeated combining the group of 20 epigenomic features (predictors) with clinical and demographic predictors including the SAC score, symptoms e.g. loss of consciousness, age of the child and gender etc. From this group of features, the optimal combination of features was used to generate the specific predictive models. These were also compared across different machine learning approaches.

As noted previously, the analysis was repeated using the top 390 epigenomic markers as a single group.

Results.

The mean (SD) age of the concussion cases was $12.71 \pm 2.70$ years and for controls was $12.45 \pm 2.76$ for controls. This is for the overall study population of 18 mTBI cases and 18 controls. Clinical comparison of the two groups are shown in Table 1. A total of 412 CpG targets were identified in which there were statistically significant differences (increased or decreased) in cytosine methylation levels in mTBI subjects compared with the normal samples (Table 2). All CpG methylation and corresponding genes targets had an AUC ROC$\geq$0.75 (FDR p-value <0.0001) for the detection of isolated mTBI. 412 protein-coding genes (Table 2), 7 microRNAs (Supplementary Table S1), 12 open reading frames (ORFs) (Supplementary Table S2), and 18 LOC genes of uncertain function (Supplementary Table S3) are aberrantly methylated and associated with mTBI.

Table 1. Comparison of Demographics and Clinical Characteristics: Cases Vs Controls.

Clinical and Demographic Data: 18 Concussion cases and 18 unaffected controls (that underwent epigenetic analysis)

|  | Mean (SD) | | |
| --- | --- | --- | --- |
|  | Cases | Controls | p-value |
| Number | 18 | 18 | — |
| Age (SD) | 12.71 (2.70) | 12.45 (2.76) | 0.771+ |
| Gender (n) | | | |
| Female | 4 | 4 | — |
| Male | 14 | 14 | — |
| BMI | 18.36 (3.56) | 20.34 (4.31) | 0.165+ |
| Neuropsychiatric disorder (n) | 2 (ADHD) | — | — |
| History of concussion (n) | 4 | 0 | <0.01^ |
| Time elapse (h) after Injury (SD) | 7.66 (5.55) | — | — |
| Type of Injury (n) | | | |
| Closed | 2 | — | — |
| Impact | 8 | — | — |

-continued

| | Mean (SD) | | |
|---|---|---|---|
| | Cases | Controls | p-value |
| Penetrating | 5 | — | |
| Sports-related injury | 6 | — | — |
| Loss of consciousness | 5 | — | <0.01+ |
| Loss of memory | 11 | — | <0.01+ |
| SAC-C score* (SD) | 20.0 (4.02) | 27.72 (1.22) | <0.01+ |
| Concentration | 2.05 (0.93) | 3.94 (0.80) | <0.01+ |
| Immediate Memory | 11.44 (3.09) | 13.72 (0.93) | <0.01+ |
| Orientation | 4.0 (1.13) | 5 (0) | <0.01+ |
| Delayed Recall | 2.55 (1.5) | 5 (0) | <0.01+ |

*SAC-C score = Concentration + Immediate Memory + Orientation + Delayed Recall
+t-test;
^Chi-square Table 2 (shown above) shows differentially methylated 412 genes with Target ID, Gene ID, chromosome location, % methylation change (compared to controls), and FDR p-value for each gene identified in the analysis (shown above). CpG sites with significant individual False Detection Rate p-values indicating methylation status and area under the receiving operator characteristic curve ≥0.75 appear to have strong potential as diagnostic biomarkers for Pediatric concussion.

Supplemental Table S1 (shown above) shows differentially methylated microRNAs in mTBI.

Supplemental Table S2 (shown above) shows differentially methylated 12 ORF genes.

Supplemental Table S3 (shown above) shows differentially methylated 18 LOC genes.

Table 3 shows metabolomic results of 17 mTBI cases and 18 controls (shown above). In Table 3, metabolites, such as C7-DC, PC aa C260, PC aa C322, PC aa C342, PC aa 362, PC aa 382, PC aa 384, asparagine, tyrosine, alpha-AAA, spermidine, D-glucose, hypoxanthine, pyroglutamic acid, and isopropyl alcohol, were found to be statistically significant, while the others can still contribute to the prediction of TBI, especially in combination with epigenomic data.

Figure 1B:
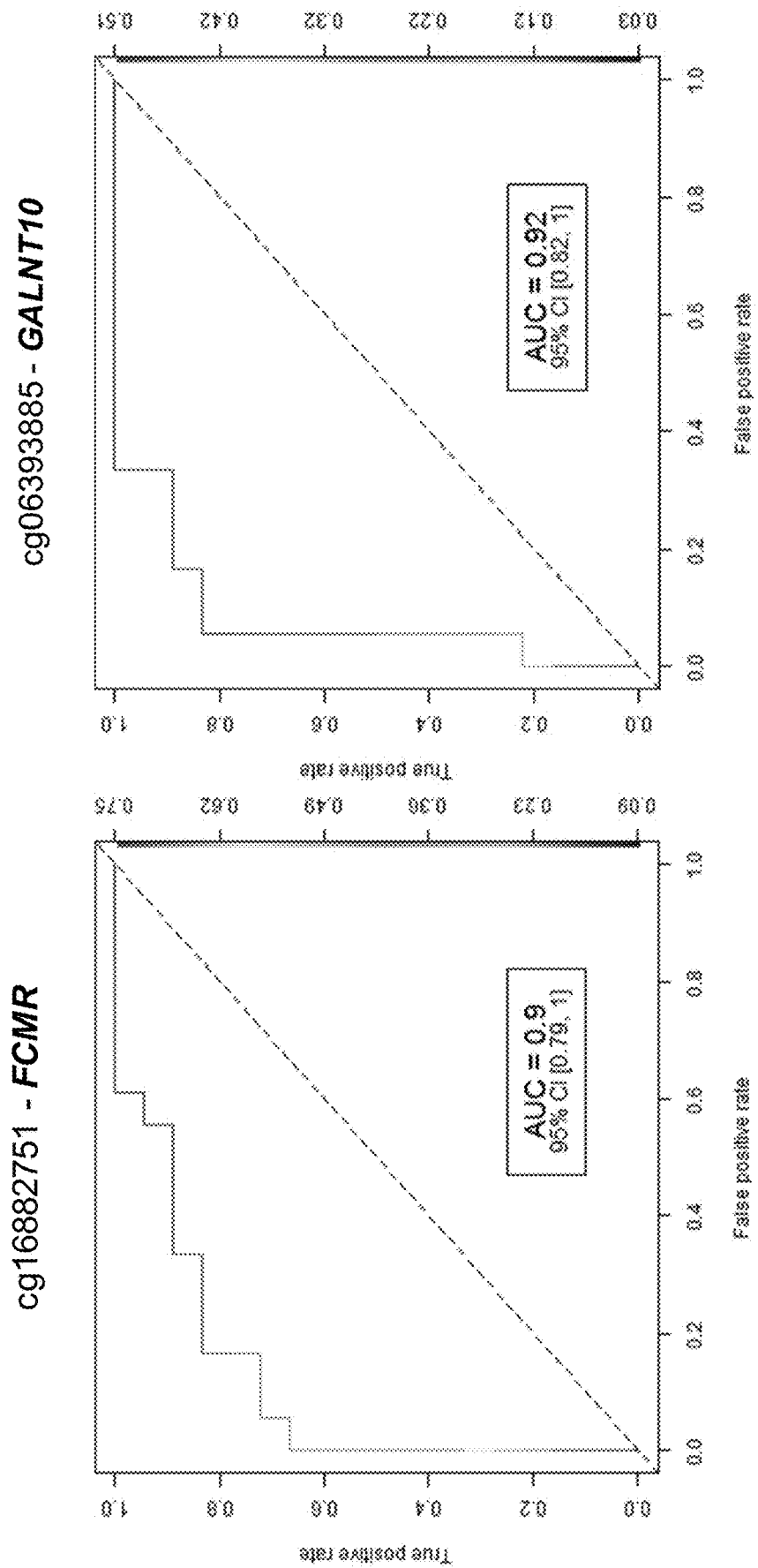

AUC is an effective way to summarize the overall diagnostic accuracy of any potential test. AUC 0.8 to 0.9 is considered excellent, and more than 0.9 is considered outstanding. In the present analysis four individual CpG loci (4 separate genes) had an individual AUC≥0.90, with an additional 119 individual CpG loci (119 genes) having an AUC between AUC≥0.8 to 0.90 for mTBI detection. FIG. 1 shows the ROC curves for four representative CpG sites (and associated genes) that had AUC>0.90 (FIG. 1).

Figure 2:
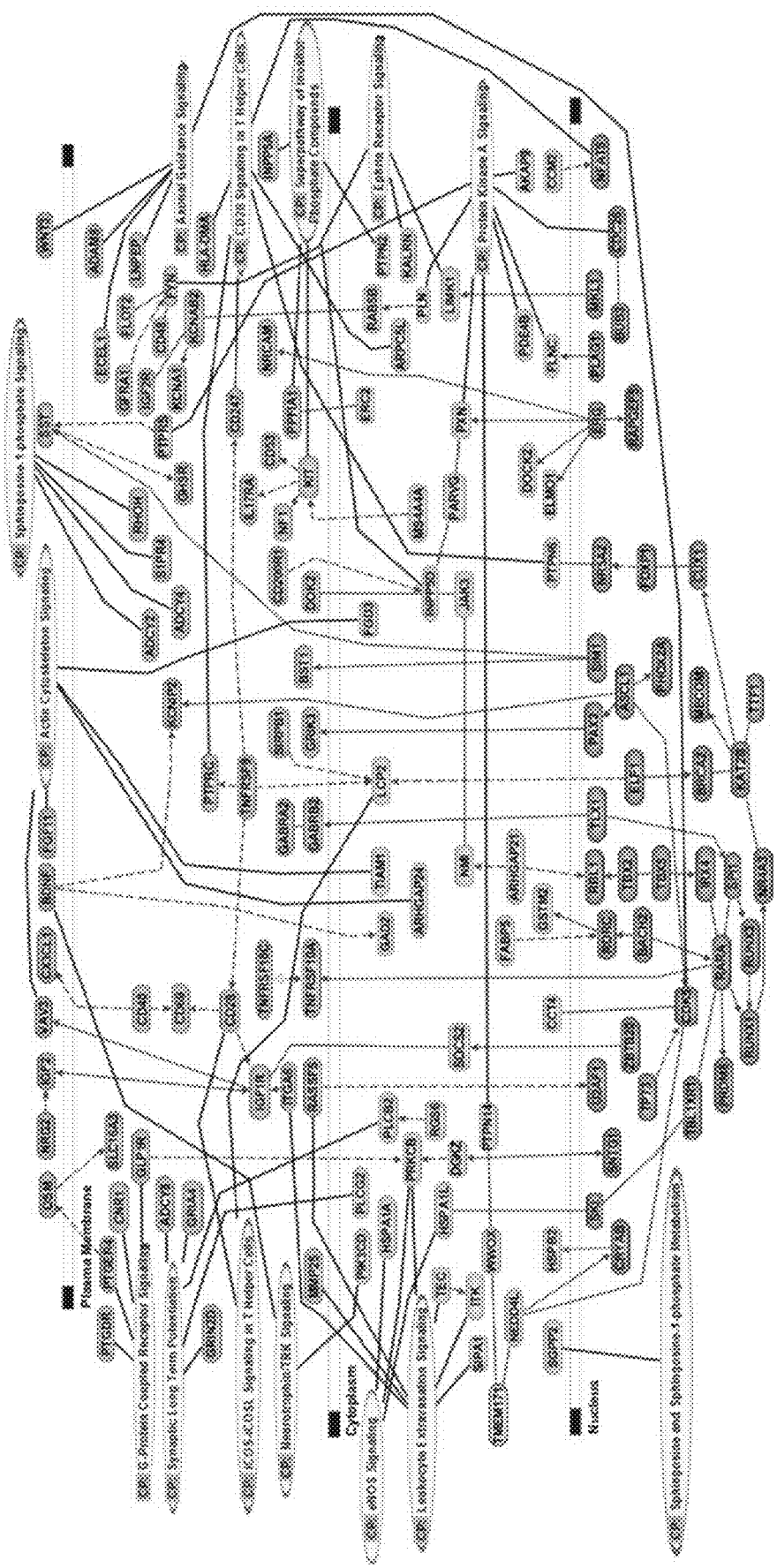
FIG. 2. Pathways analysis displaying gene and gene-pathways that appear to be epigenetically dysregulated in mTBI.

Signaling pathway analyses showed that the majority of the genes that were significantly differentially methylated were involved in multiple pathways, and most were implicated in brain function, including learning and memory pathways, and Alzheimer's disease (FIG. 2). Some of the affected pathways significantly perturbed in mTBI included G-protein coupled receptor signaling, Sphingosine-1 phosphate signaling, and Sphingosine and Sphingosine-1 phosphate metabolism. Actin Cytoskeleton Signaling and Synaptic long-term potentiation, Neurotrophin/TRK signaling, eNOS signaling, CD28 signaling in T-Helper Cells, Leukocyte extravasation signaling, Superpathway of Inositol Phosphate Compounds, Ephrin receptor signaling, Protein kinase A signaling, and Axonal guidance signaling, have all been involved in both impaired brain function, including learning and memory and also associated disorders including Alzheimer's disease. These pathway alterations may be associated with the clinical pathological features and outcome of mTBI patients.

Many of the identified genes were associated with significant dysregulation of brain function. These genes included some known to be responsible for post-concussion management (PTGER4 p=1.5, E-29), mood disorder (ADCYB, p=1.2, E-14), severe epileptic encephalopathy, seizures, cognitive, behavior (GRIN2D p=1.77, E12), pediatric bipolar disorder (HSPAIL p=1.77, E6), diminished activity of purkinje cells and disruption of motor function (INPP5A p 2.4, E19). The seven important microRNAs identified in the present study are miR-24-2, miR-548AS, miR-1938, miR-137, miR-365-1, miR-23A, and miR-27A.

Artificial Intelligence Analyses Results.

The six Machine Learning (ML)/Artificial Intelligence approaches were used to combine epigenomic, clinical and metabolomic markers.

1. Epigenomic Only Markers:

The top (based on the area under the ROC curve for each individual marker) 390 best performing individual epigenomic biomarkers was used for mTBI detection. These markers displayed excellent predictive accuracy for detection of mTBI (Table 4, shown above). Table 4 shows results of concussion prediction (total of 390 evaluated).

2 Combined Epigenomic and Clinical Markers:

The top (based on the area under the ROC curve for each individual marker) 390 best performing individual epigenomic biomarkers were combined with clinical predictors for mTBI detection. Overall addition of clinical predictors performed excellently (Table 5, shown above) but did not improve performance over epigenomics alone when considering the six AI approaches but performed just as well. Table 5 shows results of concussion prediction with epigenetic markers (total of 390 evaluated) plus clinical characteristics.

3. Combined Epigenomic, and Metabolic Markers:

The top (based on the area under the ROC curve for each individual marker) 390 best performing individual epigenomic biomarkers were combined with metabolomic markers for mTBI detection. The combination of metabolomic with genomic markers had good to excellent predictive accuracy (Table 6, shown above) depending on the ML approach used but performed less well than epigenomic markers by themselves. Table 6 shows concussion prediction based on combined epigenetic (390 markers) plus metabolomic markers.

4. Combined Epigenomic, Clinical and Metabolic Markers:

The top (based on the area under the ROC curve for each individual marker) 390 best performing individual epigenomic biomarkers were combined with metabolomic and clinical markers for mTBI detection had good to outstanding performance however this was slightly less accurate then epigenomic markers by themselves or combined with clinical predictors (Table 7, shown above). Table 7 shows combined epigenetic and metabolomic markers plus clinical characteristics for prediction of concussion.

5. Combination of Metabolomic and Clinical Markers:

The combination yielded outstanding predictive accuracy when using GLM, PAM, RF and DL approaches. These yielded areas under the ROC curves varied from 0.9789-0.9911. Using SVM and LDA the AUCs were slightly less than 0.75 (moderately accurate). (Table 8, shown above). Table 8 shows combined metabolomic markers plus clinical characteristics for concussion prediction (shown above).

Supplemental Table S4 (shown above) shows expanded epigenomic markers-pediatric concussion kit: Cases vs Controls. This table shows an expanded list of CpG loci, including more than one locus per gene that was significantly differentially methylated in concussion cases versus unaffected controls that can be used on a microarray chip for predicting the presence of a concussion.

The six Machine Learing (ML)/Artificial Intelligence approaches were used to combine multiple epigenomic markers, combine epigenomic and clinical/demographic markers and finally to combine epigenomic, clinical/demographic and metabolomic markers to achieve optimal predictive accuracy, i.e. maximal sensitivity and specificity values for concussion. Excellent to outstanding predictive accuracy was achieved using different Machine Learing approaches including Deep Learning data, the area under the ROC curve for each of the six AI techniques exceeded 0.92. Overall, higher areas under the ROC curve values were consistently achieved with DL than other Machine Learning/AI methods for the different marker combinations.

Discussion.

In recognition of the clinical importance of traumatic brain injury and the significant gaps in the understanding of this disorder, the USA Food and Drug Administration (FDA) launched the launched the Critical Pathway initiative (CPI) in 2004 to promote research collaboration for the detection and treatment of TBI. Predictive tests being considered include imaging and blood-based biomarkers. Given the complexity of the cellular mechanisms in TBI the unique potential value of a systems biology approach using high through-put genomics and proteomic approaches for understanding the disease mechanisms and for bio-marker generation is now being recognized (Feala J D, Abdulhameed M D M, Yu C et al. Systems biology approaches for discovering biomarkers for traumatic brain injury. *Neurotrauma* 2013; 30:1101-16). There were 449 significant CpG methylation variations (p<0.05) identified in 449 genomic regions associated with pediatric concussion, including 412 protein-coding genes, 7 microRNAs, 12 ORFs and 18 LOC genes linked to mTBI.

A large number of potential epigenomic biomarkers were identified for the detection of pediatric concussion. Diagnostic performance of individual CpG methylation sites was evaluated for the prediction of pediatric concussion. The area under the ROC curve and 95% CI was used to determining the diagnostic accuracy of the individual markers. The single best performing CpG locus per gene was considered. There were 100 CpG methylation markers with good diagnostic accuracy defined as AUC≥0.80-0.89 for the detection of concussion. In addition, there were eight other putative epigenomic-biomarkers with excellent diagnostic accuracy defined as AUC≥0.90-1.00. While only a single marker per gene was considered, a combination of markers within the same gene can further enhance the diagnostic accuracy of prediction. Likewise, a combination of CpG loci from different genes can also improve cumulative diagnostic accuracy over that of individual epigenomic markers.

The performance of different combinations of epigenomic, metabolomic and clinical data for the prediction of pediatric concussion was assessed. Six different Machine LearninglArtificial Intelligence techniques were used to assess the robustness of each algorithms. Consistently excellent to outstanding accuracies based on the AUCs for the prediction of concussion was achieved across the different AI techniques. Deep Learnrning consistently achieved the highest overall predictive accuracy for the prediction of concussion compared to other AI techniques. Using Deep Learning and other AI techniques, epigenomic markers by themselves had good to excellent diagnostic accuracy as determined by AUC values. The performance was further improved by the addition of clinical markers and the standard concussion assessment tool, Standard assessment of Concussion (SAC) clinical evaluation and other clinical and demographic factors (they did not all contribute to overall predictive accuracy). The predictive accuracy was high with the use of epigenomic markers and slightly improved when clinical or clinical plus metabolomic markers were used when only subgroups of epigenomic markers were considered. When a large number of epigenomic markers were considered simultaneously (top 390) the performance of these markers was excellent with minimal improvement from the consideration of clinical and psychological markers or predictions. Overall, higher areas under the ROC curve values were consistently achieved with DL over other AI methods.

To determine whether the findings that genes are epigenetically modified in TBI/concussion are merely chance findings or likely to be significant it is important to assess whether biological plausibility exists. In other words, are the genes (and related gene pathways) found to be epigenetically altered known, suspected or plausibly linked to neuronal activity, the brain dysfunction or other brain disorders that that are known or suspected to develop as a result of head injury or that are currently thought to be related to traumatic neuronal injury. A number of important genes with potential functional consequences from aberrant genome-wide DNA methylation was identified. Pathway analysis revealed differentially methylated genes in mTBI that are known to be involved in impaired brain function, including learning and memory, and Alzheimer's disease; each of these over-represented (read differentially activated) pathways found in the analyses are briefly discussed below. This gives our findings significant biological plausibility.

Genes in G-Protein Coupled Receptor Signaling.

G-protein coupled receptors (GPCRs) belong to a large family of membrane proteins with characteristic seven membrane-spanning α-helical segments. GPCRs modulate numerous cellular responses to neurotransmitters and hormones at the neuronal synapse [26] and regulate processes of electric and chemical activity at the connection between neurons [27]. Specialized G-protein-signaling pathways can exert control over the levels of cytoplasmic $Ca^{2+}$, which is involved in excitation or inhibition at the synapse [28]. Based on the location of these GPCRs, they act as auto-receptors and regulate neurotransmission at the synapses. Approximately 80% of neurotransmitters exert their effects through interactions with GPCRs [29]. This neurochemical cascade plays a significant role during concussion [30]. PTGDR (Prostoglandin D2 Receptor), which is a GPCR gene, is expressed by astrocytes and is involved in the inflammation of brain [31]. Significant differences in PTGDR gene expression were demonstrated in the rat brain after traumatic brain injury [32]. PTGER4 (Prostaglandin EP4) is involved in the defense against neurotoxicity [33] and differential DNA methylation of this gene was identified in this study that may attenuate excitotoxic brain injury [33].

Genes in Sphingosine-1 Phosphate Signaling and Sphingosine and Sphingosine-1 Phosphate Metabolism.

Sphingosine-1-phosphate (S1P) is a bioactive lipid mediator that signals through the activation of S1P receptors and a family of G protein-coupled receptors. The receptors for S1P are expressed by both astrocytes and endothelial cells in the brain [34]. This lipid mediator participates in regulating cellular functions such as cell proliferation, cell process retraction, cell survival and migration in the central nervous system (CNS). The expression level of sphingosine genes (S1P1, S1P2, S1P3, S1P4, S1P5) alters during and after brain damage [35, 36]. Receptors of sphingosine gene (S1PR4) identified to be hypomethylated in this study, have previously been reported in association with ischemic brain injury [37]. ADCY4 (Adenyl cyclase type 4) has been identified to be involved in neuro-pathophysiological conditions [38] and we observed hypomethylation of ADCY4 in this study.

Genes in Actin Cytoskeleton Signaling and Synaptic Long-Term Potentiation.

These two pathways contain five important genes which were found to be differentially methylated in this study i.e., ADCY8, GRIN20, PLCG2, FGD3, ARHGAP24. Synapses in cortical and hippocampal neurons form at cellular protrusions called dendritic spines that are rich in actin proteins [39]. Synaptic activity of the brain regulates the morphology of dendritic spines through changes in actin polymerization. These dendritic spines can alter the long-term synaptic strength [40, 41]. The process of "synaptic long term potentiation" initiates polymerization of actin filaments on dendritic spines, leading to the stability of F-actin, regulated by calcium dependent kinases and GTPases [42, 43). The gene product of ADCY8 is adenyl cyclase, and the receptor for adenyl cyclase binds to G proteins and has a GTPase activity. In the present study, patients with concussion demonstrated significant dysregulation of the ADC YB gene, which has also been reported to play a role in human mood disorders [44].

A rare sequence variation in PLCG2, and FGD3 genes (found to be hypomethylated) have been observed in Alzheimer's disease [45, 46]. The ARHGAP24 gene has a potential role in branching and outgrowth of axons and dendrites in the brain [47]. Variations in gene methylation have been observed to be associated with intellectual disability in children. The present study identified hypomethylation on GRIN2D. Alterations of the GRIN2D gene has been reported in patients with neurological deficits including severe epileptic encephalopathy, seizures, and cognitive impairment, [48]. These clinical manifestations are seen in concussion patients [49].

Genes in Neurotrophin/TRK Signaling.

Neurotrophins are class of signaling molecules belonging to the group of homodimeric polypeptide growth factors. Neurotrophins promote neuronal development, survival, and death [50] [51] [41]. Two important genes in the neurotrophin/TRK signaling pathway that were found by us to be differentially methylated following mTBI were brain-derived neurotrophic factor (BDFN) and PIK3CD. BDNF encodes for nerve growth factor and has been extensively studied and found to be associated with multiples brain disorders including traumatic brain injury [52], bipolar disorder [53], and Alzheimer's disease [54]. The PIK3CD (Phosphatidylinositol-4, 5-Bisphosphate 3-Kinase Catalytic Subunit Delta) gene is involved in immune function and although gene expression occurs primarily in leucocytes it is also expressed in the brain. Decreased expression has been reported in traumatic brain injury [55]. This is also considered to be important gene in mTBI recovery.

Genes in eNOS (Endothelial Nitric Oxide Synthase) Signaling.

Cerebral blood now is regulated by the key signaling molecule nitric oxide (NO), under both physiological conditions and after the brain injury. Two important mechanisms are known to regulate cerebral blood now; one is autoregulation involving eNOS-generated NO and the other is neurovascular coupling, where nNOS-derived NO plays a key role [56]. One study found that post-traumatic cerebral blood now and pressure autoregulation mediation by erythropoietin depended on eNOS signaling [57]. HSPAIL, found to be differentially methylated in the study, is a heat shock protein that may play a role in regulating eNOS signaling [58]. Differential methylation of HSPA 1L was also been previously found to be associated with pediatric bipolar disorder [59, a type of psychiatric disorder that may follow traumatic brain injury and concussion in certain patients [60].

Genes in CD28 Signaling in T-Helper Cells.

A number of genes found to be differentially methylated in the study have important roles in immune system inflammatory pathways, including PTPRC (CD45), HLA-DMA, NFAT5 and PTPN6. Brain injury activates crosstalk between the immune system and injured brain. For example, following an intracerebral hemorrhage there is increased T lymphocyte migration [61] and increased production of cytokines occur. The adaptive immune response plays a crucial role in resolving inflammation and promoting the process of repair in neurodegeneration. These mechanisms are deficient in neurodegenerative disorders [62]. PTPRC (CD45) has been extensively studied and is highly expressed on macrophages at the site of injury in TBI [63].

Protein tyrosine phosphatase is the product of the PTPRC gene, an important regulator of T- and B-cell receptor signaling and cytokine receptor signaling. HLA-DMA encodes a Class II transmembrane protein that is expressed in antigen presenting cells such as dendrites and B-lymphocytes and has been shown to have a role in Alzheimer's disease [64]. NFAT5 codes for a gene transcription factor involved in controlling gene transcription during an immune response. A study in mice revealed disruption of expression levels of NFAT5 following ischemic injury which affected osmolarity, an important determinant of intracranial pressure [65, 66], and the neuronal cell death process [66]. The protein transcript of the PTPN6 gene is a PTP (protein tyrosine phosphatase), a signaling molecule involved in many cellular functions such as mitosis, cell growth and differentiation. It is primarily expressed in hematopoietic cells. Altered PTPN6 expression has also been identified after traumatic brain injury in a mouse model [67]. The genes, PTPRC, HLA-DMA, NFAT5 and PTPN6 were identified to be hypomethylated in this study subjects.

Genes in Leukocyte Extravasation Signaling.

Signal-induced proliferation activating family (SIPA1) gene and IL2 inducible T-cell kinase (ITK) were hypomethylated in mTBI samples in this study. The blood-brain barrier normally provides immune protection to the brain by restricting the passage of cells and other substances in and out of the brain. While leukocyte migration is essential for normal physiology and host defense, the blood-brain barrier restricts this process [34]. Inflammation is characterized by weakened blood brain barrier function, increased reactive oxygen species and endothelial cell adhesion molecules, leukocyte recruitment, recruitment of other inflammatory cells and platelets. All these processes increase during brain injury (68). The transcription product of SIPA1 encodes signal-induced proliferation activating protein 1, which is increased in several metastatic cancers and might be involved in cell migration. The role of S/PA1 in TBI is not clear at this time. The IL2 inducible T-cell kinase (ITK) gene product has capacity to induce neuroinflammation by regulating $CD4^+$ T-cell activation and trafficking [69]. An ITK mutation affecting the SH2 domain has been identified in a patient who died after ischemic brain injury [70]. We identified hypomethylation on ITK gene.

Genes in Superpathway of Inositol Phosphate Compounds.

The Inositol Polyphosphate-4-Phosphatase Type IA gene (INPP4A) codes for a family of inositol phosphates and was found to be differentially methylated in this study. Inositol phosphates play a diversified role in membrane trafficking, actin cytoskeleton maintenance, and regulation of cell survival and cell death. They also anchor to the plasma membrane proteins and help regulate osmolyte concentration, [71-73]. This is important for maintaining fluid balance in the CNS through the mobilization of intracellular calcium along with the traffic of ions such as $Na^+$, $K^+$, $H^+$ and $Cl^-$ across the plasma membrane [74,75]. Physical injuries affecting the blood brain barrier may disrupt the inflow and outflow of these molecules or ions resulting in vasogenic edema and other pathologies [76]. One study showed that a patient with a large deletion in the INPP4A gene had early-onset cerebellar atrophy and myoclonic seizures [77]. Mutations of the INPP5A gene, which was found to be differentially methylated in this study, reportedly lead to diminished activity of purkinje cells and disruption of motor function [78, 79], which is another clinical feature of concussion [80].

Genes in Ephrin Receptor Signaling.

In the early embryonic brain, neuro-epithelial cells abundantly express ephrin receptors. Null mutation of the ephrin results in the development of a larger brain size during embryogenesis, while over expression of ephrin gene signaling initiates neuro-epithelial cell apoptosis, thus indicating that ephrin is important for both apoptosis and maintenance of brain size [81]. Knox reported [82] ischemic brain injury in mice with Fyn gene mutations. FYN gene hypomethylation was observed in the present study.

Genes in Protein Kinase A Signaling.

Protein kinase cascades play key roles in cellular processes such as survival, proliferation, differentiation, growth arrest and apoptosis, during which various transcription factors are induced to modify gene expression. Mitogen-activated protein kinases (MAPKs) are serine/threonine protein kinases involved in critical cellular functions such as stress response, apoptosis and the survival of neuronal cells and altered expression of MAPKs can lead to brain damage [83]. A group of protein kinases called death-associated protein kinases have also been identified in cerebral ischemic damage. They cause cell death through the induction of processes such as excitotoxicity, autophagy, membrane blebbing and DNA fragmentation [84]. At-least 3 protein kinase signaling cascades are activated in response to CNS trauma including MAPKs, protein kinase B/Akt and glycogen synthase kinase [85]. Several genes differentially methylated in this study were found to be associated with protein kinase A signaling on pathway analysis. These included PXN, CDC26 and PDE48. PXN has been identified in multiple pathways involved in the cerebellar response to hypoxia [86]. CDC26 was found to be downregulated in a murine neuronal differentiation study and the same study identified the upregulation of the BDNF [87] PDE48, which was differentially methylated in this study, is known to play a role in brain inflammation by inducing pro-inflammatory marker TNF-α in circulating monocytes and macrophages [88]. Hypoxia, neuronal differentiation and brain inflammation are all features of traumatic brain injury and concussion [89].

Genes in Axonal Guidance Signaling.

Axonal guidance plays a key role in the brain neuronal network during fetal development and also is involved in the connectivity and repair mechanism of the brain throughout life [90]. Over- or under-expression of the axonal guidance pathway induced by trauma may hamper the healing process. Wnt genes intensely influence axon plasticity and axon pathfinding. The Wnt signaling pathway is involved in disruption of axon guidance signaling during brain injuries [91, 92]. One of the major WNT family genes, WNT3, was differentially methylated in this study, and was previously found to be differentially methylated in autism, leading to dysregulation in neurogenesis and neural developmental pathways [93].

Genes in Micro RNAs and Pediatric Concussion.

MicroRNAs (miRNAs or miRs) are small noncoding RNAs that control gene expressions at the post-transcriptional level. Approximately 66% of all mRNAs are controlled by miRNAs in the human genome [94]; the cerebrum contains approximately 70% of all known miRNAs identified [95]. Crucial developmental processes of the brain including CNS development, synapse formation and memory function involves post-transcriptional regulation by miRNAs [94, 96]. Modified action in these miRNAs hamper the downstream pathways essential for normal functioning [97]. Single miRNAs targeting multiple mRNAs (messenger RNA) as well as single mRNAs targeted by multiple miRNAs have now been shown to be involved in a number of disorders [95]. Aberrant methylation of miRNA gene promoter region has now been causatively linked to the development of neurodegenerative disorders (Chhabra 2015) hence the interest in looking specifically at the methylation of miRNA genes throughout the genome.

miR-24-2, miR-548AS, miR-1938, miR-137, miR-365-1, miR-23A, and miR-27A were identified to be differentially methylated in the pediatric concussion study. A study of traumatic brain injury linked dysregulated miRNA expression led to neuronal cell death (98). The present study found differential methylation of miR24-2, supporting findings that the downregulation of the miR-24 family was associated with neuronal apoptosis and caspase-3 activation [98]. miR-24-2 has also been identified as one of the factors involved in changes in normal brain-endothelial barrier function during neuro-inflammation [99]. miR-1938 has not been investigated in brain injury studies but has been associated with the promotion of cell proliferation in glioma patients by targeting SMAD3 [100].

miR-137 is a very important micro RNA molecule that plays a crucial role in neural development, neoplastic transformation [101], neuronal maturation [102] and has been identified in association with schizophrenia [103]. It has been found to be down-regulated in the blood of stroke patients and has been associated with post-stroke depression [104]. Further, reduced expression of miR-137 has been linked with traumatic brain injury in mice, [105] which is mirrored in the clinical population of this study. miR-23A and miR-27A were both found to be hyper-methylated in pediatric concussion patients in thisstudy. They were also identified in a traumatic brain injury study where neuronal cell death was induced (98). Again, the results of this study support these findings. It has been reported that improvement in miR-23A expression levels correlate with recovery from traumatic brain injury and reduction in cognitive impairment [106]. Overexpression of miR-27A is neuroprotective and can attenuate neurological deficits, and also attenuate traumatic brain injury-induced neuronal autophagy [107].

LOC Genes.

There were 18 genes identified and designated as "LOC" e.i. that are uncharacterized and currently not annotated i.e. published gene symbols or abbreviations for the gene name is currently not available. None of these genes have previously been associated with concussion or brain injuries, and among the 18, only two genes were identified as probable targets of brain function. LOC 100134368 has been putatively associated with the neuronal development process through its differential expression levels in umbilical cord tissue from extremely low gestational age newborns [108]. LOC645323 has been identified to have a conserved exonic structure and sequence to the mouse Visc-1 transcript. The sequence match is approximately 82% and LOC645323 is considered as orthologous to mouse Visc-1 gene [109]. Visc-1 along with Visc-2 are long non-coding RNA genes that are highly expressed in brain and may have an important biological function. Visc-1 is preferentially expressed in the developing forebrain and is co-localized with rostral and caudal interneuron migratory streams [109]. This signifies a plausible effect of these LOC genes in the pathophysiology of concussion in children on differential methylation status. However, the detailed biological functions of these genes are yet to be identified.

ORF Genes.

An open reading frame (ORF) is a nucleic acid sequence without a stop codon in its reading frame that can be translated into a potential functional protein product [110]. A total of 12 open reading frame genes were identified as being differentially methylated in this study; among them a hypomethylated gene, C2orf40 has been previously associated with a brain-related anomaly to our knowledge. C2orf40 is a neuro-immune factor and in transgenic mice, expression of this gene results in the aggregation of neurofibrillary tangle-protein tau, responsible for the induction of senescence in the central nervous system and also is associated with tumor suppression and Alzheimer's disease. Along with these functions, C2orf40 has been identified as an inflammatory factor in Alzheimer's disease (Chhabra R. (2015) miRNA and methylation: a multifaceted liaison. Chembiochem 16, 195-203).

Conclusion.

In this study, blood based epigenomic and metabolomic biomarkers that appear to have excellent to outstanding diagnostic accuracy for the detection of concussion were identified. Regarding the epigenomic aspect of the study, we have found blood molecular markers that are associated with changes in mTBI. We have also identified genes and gene pathways that are known or can be plausibly linked to neuronal and brain function and dysfunction that have been epigenetically dysregulated. These results give biological plausibility to our findings. These markers can be used by themselves or in combination with currently used clinically parameters. Similarly, metabolomic markers by themselves or combined with psychological testing scores yield good to excellent accuracy of detection for TBI. Multiple AI techniques were used simultaneously to assess and confirm the robustness of epigenomic and metabolomic biomarkers for the detection of pediatric concussion. AI has the advantage that it can find patterns in data that might not be identified using conventional statistical analysis. AI is particularly advantageous when a large number of predictors are being simultaneously evaluated in the same patient. Finally, the accuracy of AI prediction improves the larger the number of subjects evaluated by this approach. The consequence is likely to be further improvement in accuracy of prediction when larger number of cases and controls than used in this study is evaluated in the future—such as population based screening tests e.g. for high school athletes. The high predictive accuracy observed is potentially important clinically given the fact that a significant proportion, potentially even the majority of concussions are undiagnosed particularly in vulnerable subjects such as children. In the present genome-wide methylation study, >400 CpG loci had fair to outstanding CpG accuracy for TBI detection. Also, microRNAs, ORFs and LOC genes demonstrated significant methylation variation between mTBI and control subjects. Many of these genes and gene pathways are of substantial importance in normal brain development function and have been implicated in numerous brain pathologies. Deep Learning and other AI techniques were used to achieve high diagnostic performance using epigenomics alone or combined with clinical and metabolomic data. This is the first analysis using AI and the first combining epigenomic and metabolomic for concussion prediction.

The subject matter described above is provided by way of illustration only and should not be construed as limiting. Various modifications and changes may be made to the subject matter described herein without following the example embodiments and applications illustrated and described. and without departing from the true spirit and scope of the present invention, which is set forth in the following claims.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±15% of the stated value; ±10% of the stated value; ±5% of the stated value; ±4% of the stated value; ±3% of the stated value; ±2% of the stated value; ±1% of the stated value; or ±any percentage between 1% and 20% of the stated value.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

REFERENCES

1. Langlois J A, Rutland-Brown W, Wald M M: The epidemiology and impact of traumatic brain injury: a brief overview. *J Head Trauma Rehabil* 2006, 21(5):375-378.
2. Carroll L J, Cassidy J D, Peloso P M, Borg J, von Hoist H, Holm L, Paniak C, Pepin M, Injury WHOCCTFo-MTB: Prognosis for mild traumatic brain injury: results of the WHO Collaborating Centre Task Force on Mild Traumatic Brain Injury. *J Rehabil Med* 2004 (43 Suppl): 84-105.
3. Mayer A R, Quinn D K, Master C L: The spectrum of mild traumatic brain injury: A review. *Neurology* 2017, 89(6): 623-632.
4. McKee A C, Stem R A, Nowinski C J, Stein T D, Alvarez V E, Daneshvar D H, Lee H S, Wojtowicz S M, Hall G, Baugh C M el al: The spectrum of disease in chronic traumatic encephalopathy. *Brain* 2013, 136(Pt 1):43-64.
5. Karlin A M: Concussion in the pediatric and adolescent population: "different population, different concerns". *PM R* 2011, 3(10 Suppl 2):S369-379.
6. Moser R S, Schatz P, Jordan B O: Prolonged effects of concussion in high school athletes. *Neurosurgery* 2005, 57(2):300-306; discussion 300-306.
7. Anderson V, Moore C: Age at injury as a predictor of outcome following pediatric head injury: A longitudinal perspective. *Child Neurophyschol* 1995(1):187-202.
8. Cook R S, Schweer L, Shebesta K F, Hartjes K, Falcone R A, Jr.: Mild traumatic brain injury in children: just another bump on the head? *J Trauma Nurs* 2006, 13(2): 58-65.
9. In: *Sports-Related Concussions in Youth: Improving the Science, Changing the Culture*. Edited by Graham R, Rivara F P, Ford M A, Spicer C M. Washington (DC); 2014.
10. Sim A, Terryberry-Spohr L, Wilson K R: Prolonged recovery of memory functioning after mild traumatic brain injury in adolescent athletes. *J Neurosurg* 2008, 108(3):511-516.
11. McKinlay A, Dalrymple-Alford J C, Horwood L J, Fergusson D M: Long term psychosocial outcomes after mild head injury in early childhood. *J Neurol Neurosurg Psychiatry* 2002, 73(3):281-288.
12. Papa L: Potential Blood-based Biomarkers for Concussion. *Sports Med Arthrosc* 2016, 24(3):108-115.
13. Bennett E R, Reuter-Rice K, Laskowitz D T: Genetic Influences in Traumatic Brain Injury. In: *Translational Research in Traumatic Brain Injury*. Edited by Laskowitz D, Grant G. Boca Raton (Fla.); 2016.
14. Blackman J A, Worley G, Strittmatter W J: Apolipoprotein E and brain injury: implications for children. *Dev Med C/1ild Neurol* 2005, 47(1):64-70.
15. Kurowski B, Martin L J, Wade S L: Genetics and outcomes after traumatic brain injury (TBI): what do we know about pediatric TBI? *J Pediatr Rehabil Med* 2012, 5(3):217-231.
16. Gao W M, Chadha M S, Kline A E, Clark R S, Kochanek P M, Dixon C E, Jenkins L W: Immunohistochemical analysis of histone H3 acetylation and methylation—evidence for altered epigenetic signa ling following traumat ic brain injury in immature rats. *Brain Res* 2006, 1070(1):31-34.
17. Zhang Z Y, Zhang Z, Fauser U, Schluesener H J: Global hypomethylation defines a sub-population of reactive microglialmacrophages in experimental traumatic brain injury. *Neurosci Lett* 2007, 429(1):1-6.
18. Dash P K, Hergenroeder G W, Jeter C B, Choi H A, Kobori N, Moore A N: Traumatic Brain Injury Alters Methionine Metabolism: Implications for Pathophysiology. *Front Sys/Neurosci* 2016, 10:36.
19. Petrone A B, Gionis V, Giersch R, Barr T L: Immune biomarkers for the diagnosis of mild traumatic brain injury. *NeuroRehabililalion* 2017, 40(4):501-508.
20. Radhakrishna U, Albayrak S, Alpay-Savasan Z, Zeb A, Turkoglu O, Sobolewski P, Bahado-Singh R O: Genome-Wide DNA Methylation Analysis and Epigenetic Variations Associated with Congenital Aortic Valve Stenosis (AVS). *PLoS One* 2016, 11(5):e0154010.
21. Liu Y, Aryee M J, Padyukov L, Fallin M D, Hesselberg E, Runarsson A, Reinius L, Acevedo N, Taub M, Ronninger M et al: Epigenome-wide association data implicate DNA methylation as an intermediary of genetic risk in rheumatoid arthritis. *Nat Biotechnol* 2013, 31(2):142-147.
22. Daca-Roszak P, Pfeifer A, Zebracka-Gala J, Rusinek O, Szybinska A, Jarzab B, Witt M, Zietkiewicz E: Impact of SNPs on methylation readouts by Illumina Infinium HumanMethylation450 BeadChip Array: implications for comparative population studies. *BMC Genomics* 2015, 16(1):1003.
23. Chen Y A, Lemire M, Choufani S, Butcher O T, Grafodatskaya D, Zanke B W, Gallinger S, Hudson T J, Weksberg R: Discovery of cross-reactive probes and polymorphic CpGs in the Illumina Infinium HumanMethylation450 microarray. *Epigenelics* 2013, 8(2):203-209.
24. WIlhelm-Benartzi C S, Koestler D C, Karagas M R, Flanagan J M, Christensen B C, Kelsey K T, Marsit C J, Houseman E A, Brown R: Review of processing and analysis methods for DNA methylation array data. *Br J Cancer* 2013, 109(6):1394-1402.
25. Altorok N, Tsou P S, Coit P, Khanna O, Sawalha A H: Genome-wide DNA methylation analysis in dermal fibroblasts from patients with diffuse and limited systemic sclerosis reveals common and subset-specific DNA methylation aberrancies. *Annals of/he rheumatic diseases* 2014.
26. Rosenbaum O M, Rasmussen S G, Kobilka B K: The structure and function of G-protein-coupled receptors. *Nature* 2009, 459(7245):356-363.
27. Kamat P K, Kalani A, Tyagi N: Role of hydrogen sulfide in brain synaptic remodeling. *Methods Enzymol* 2015, 555:207-229.
28. Huang Y, Thathiah A: Regulation of neuronal communication by G protein-coupled receptors. *FEBS Lett* 2015, 589(14):1607-1619.
29. Ghanemi A: Targeting G protein coupled receptor-related pathways as emerging molecular therapies. *Saudi Pharm J* 2015, 23(2): 115-129.
30. MacFarlane M P, Glenn T C: Neurochemical cascade of concussion. *Brain Inj* 2015, 29(2):139-153.
31. Bortell N, Basova L, Semenova S, Fox H S, Ravasi T, Marcondes M C: Astrocyte-specific overexpressed gene signatures in response to methamphetamine exposure in vitro. *J Neuroinflammation* 2017, 14(1):49.
32. Bimie M, Morrison R, Camara R, Strauss K I: Temporal changes of cytochrome P450 (Gyp) and eicosanoid-related gene expression in the rat brain after traumatic brain injury. *BMC Genomics* 2013, 14:303.
33. Ahmad A S, Ahmad M, de Brum-Femandes A J, Dore S: Prostaglandin EP4 receptor agonist protects against acute neurotoxicity. *Brain Res* 2005, 1066(1-2):71-77.
34 Spampinato S F, Obermeier B, Cotleur A, Love A, Takeshita Y, Sano Y, Kanda T, Ransohoff R M: Sphingosine I Phosphate at the Blood Brain Barrier: Can the Modulation of SIP Receptor I Influence the Response of Endothelial Cells and Astrocytes to Inflammatory Stimuli? *PLoS One* 2015, 10(7):e0133392.
35. Nishimura H, Akiyama T, Irei I, Hamazaki S, Sadahira Y: Cellular localization of sphingosine-1-phosphate receptor I expression in the human central nervous system. *J Histochem Cytochem* 2010, 58(9):847-856.
36. Punsawad C: A Review of the Role of Sphingosine-1-Phosphate in the Brain: An Important Mediator Implicated in the Central Nervous System. *Walailak Joumrnal of Science and Technology (WJST)* 2013, 11(5):395-402.
37. Yang D, Sun Y Y, Bhaumik S K, Li Y, Baumann J M, Lin X, Zhang Y, Lin S H, Dunn R S, Liu C Y et al: Blocking lymphocyte trafficking with FTY720 prevents inflammation—sensitized hypoxic-ischemic brain injury in newborns. *J Neurosci* 2014, 34(49):16467-16481.
38. Kumar G, Chhabra A, Mishra S, Kalam H, Kumar D, Meena R, Ahmad Y, Bhargava K, Prasad O N, Sharma M: H2S Regulates Hypobaric Hypoxia-Induced Early Glio-Vascular Dysfunction and Neuro-Pathophysiological Effects. *EBioMedicine* 2016, 6:171-189.
39. Okamoto K, Nagai T, Miyawaki A, Hayashi Y: Rapid and persistent modulation of actin dynamics regulates postsynaptic reorganization underlying bidirectional plasticity. *Nat Neurosci* 2004, 7(10):1104-1112.
40. Rochefort N L, Konnerth A: Dendritic spines: from structure to in vivo function. *EMBO Rep* 2012, 13(8): 699-708.
41. Gordon-Weeks P R, Fournier A E: Neuronal cytoskeleton in synaptic plasticity and regeneration. *J Neurochem* 2014, 129(2):206-212.
42. Lin W H, Webb D J: Actin and Actin-Binding Proteins: Masters of Dendritic Spine Formation, Morphology, and Function. *Open Neurosci J* 2009, 3:54-66.
43. Saneyoshi T, Hayashi Y: The Ca2+ and Rho GTPase signaling pathways underlying activity-dependent actin remodeling at dendritic spines. *Cytoskeleton (Hoboken)* 2012, 69(8):545-554.
44. de Mooij-van Malsen A J, van Lith H A, Oppelaar H, Hendriks J, de Wit M, Kostrzewa E, Breen G, Collier D A, Olivier B, Kas M J: Interspecles trait genetics reveals association of Adcy8 with mouse avoidance behavior and a human mood disorder. *Biol Psychiatry* 2009, 66(12): 1123-1130.
45. Sims R, van der Lee S J, Naj A C, Bellenguez C, Badarinarayan N, Jakobsdottir J, Kunkle B W, Boland A, Raybould R, Bis J C et al: Rare coding variants in PLCG2, ABI3, and TREM2 implicate microglial-mediated innate immunity in Alzheimer's disease. *Nat Genet* 2017.
46. Bai Z, Stamova B, Xu H, Ander B P, Wang J, Jickling G C, Zhan X, Liu D, Han G, Jin L W et al: Distinctive RNA expression profiles in blood associated with Alzheimer disease after accounting for white matter hyperintensities. *Alzheimer Dis Assoc Disord* 2014, 28(3): 226-233.
47. Coutton C, Dieterich K, Satre V, Vieville G, Amblard F, David M, Cans C, Jouk P S, Devillard F: Array-CGH in children with mild intellectual disability: a population—based study. *Eur J Pediatr* 2015, 174(1):75-83.
48. Li D, Yuan H, Ortiz-Gonzalez X R, Marsh E D, Tian L, McCormick E M, Kosobucki G J, Chen W, Schulien A J, Chiavacci R el al: GRIN2D Recurrent De Novo Dominant Mutation Causes a Severe Epileptic Encephalopathy Treatable with NMDA Receptor Channel Blockers. *Am J Hum Genet* 2016, 99(4):802-816.
49. Guskiewicz K M, Ross S E, Marshall S W: Postural Stability and Neuropsychological Defic its After Concussion in Collegiate Athletes. *J A/hi Train* 2001, 36(3):263-273.
50. da Silva Meirelles L, Simon D, Regner A: Neurotrauma: The Crosstalk between Neurotrophins and Inflammation in the Acutely Injured Brain. *Int J Mo/Sci* 2017, 18(5).
51. Huang E J, Reichardt L F: Neurotrophins: roles in neuronal development and function. *Annu Rev Neurosci* 2001, 24:677-736.
52. Kaplan G B, Vasterling J J, Vedak P C: Brain-derived neurotrophic factor in traumatic brain injury, post-traumatic stress disorder, and their comorbid conditions: role in pathogenesis and treatment. *Behav Pharmacol* 2010, 21(5-6):427-437.

53. Femandes B S, Molendijk M L, Kohler C A, Soares J C, Leite C M, Machado-Vieira R, Ribeiro T L, Silva J C, Sales P M, Quevedo J et al: Peripheral brain-derived neurotrophic factor (BDNF) as a biomarker in bipolar disorder: a meta-analysis of 52 studies. *BMC Med* 2015, 13:289.
54. Beeri M S, Sonnen J: Brain BDNF expression as a biomarker for cognitive reserve against Alzheimer disease progression. *Neurology* 2016, 86(8):702-703.
55 White T E, Surles-Zeigler M C, Ford G D, Gates A S, Davids B, Distel T, LaPlaca M C, Ford B O: Bilateral gene interaction hierarchy analysis of the cell death gene response emphasizes the significance of cell cycle genes following unilateral traumatic brain injury. *BMC Genomics* 2016, 17:130.
56. Garry P S, Ezra M, Rowland M J, Westbrook J, Pattinson K T: The role of the nitric oxide pathway in brain injury and its treatment—from bench to bedside. *Exp Neurol* 2015, 263:235-243.
57. Cruz Navarro J, Pillai S, Ponce L L, Van M, Goodman J C, Robertson C S: Endothelial nitric oxide synthase mediates the cerebrovascular effects of erythropoietin in traumatic brain injury. *Front Immunol* 2014, 5:494.
58. Amour J, Brzezinska A K, Weihrauch D, Billstrom A R, Zielonka J, Krolikowski J G, Bienengraeber M W, Waritier D C, Pratt P F, Jr., Kersten J R: Role of heat shock protein 90 and endothelial nitric oxide synthase during early anesthetic and ischemic preconditioning. *Anesthesiology* 2009, 110(2):317-325.
59. Fries G R, Quevedo J, Zeni C P, Kazimi I F, Zunta-Soares G, Spiker D E, Bowden C L, Waiss-Bass C, Soares J C: Integrated transcriptome and methylome analysis in youth at high risk for bipolar disorder: a preliminary analysis. *Transl/Psychiatry* 2017, 7(3):e1059.
60. Schwarzbold M, Diaz A, Martins E T, Rufino A, Amante L N, Thais M E, Quevedo J, Hohl A, Linhares M N, Walz R: Psychiatric disorders and traumatic brain injury. *Neuropsychiatr Dis Treat* 2008, 4(4):797-816.
61. Ma L, Shen X, Gao Y, Wu Q, Ji M, Luo C, Zhang M, Wang T, Chen X, Tao L: Blocking B7-1/C028 Pathway Diminished Long-Range Brain Damage by Regulating the Immune and Inflammatory Responses in a Mouse Model of Intracerebral Hemorrhage. *Neurochem Res* 2016, 41(7):1673-1683.
62. Amor S, Peferoen L A, Vogel D Y, Breur M, van der Valk P, Baker D, van Noori J M: Inflammation in neurodegenerative diseases—an update. *Immunology* 2014, 142(2):151-166.
63. Hsieh C L, Kim C C, Ryba B E, Niemi E C, Sando J K, Locksley R M, Liu J, Nakamura M C, Seaman W E: Traumatic brain injury induces macrophage subsets in the brain. *Eur J Immunol* 2013, 43(8):2010-2022.
64. Cribbs D H, Berchtold N C, Perreau V, Coleman P D, Rogers J, Tenner A J, Cotman C W: Extensive innate immune gene activation accompanies brain aging, increasing vulnerability to cognitive decline and neurodegeneration: a microarray study. *J Neuroinflammation* 2012, 9:179.
65. Haddad S H, Arabi Y M: Critical care management of severe traumatic brain injury in adults. *Scand J Trauma Resusc Emerg Med* 2012, 20:12.
66. Shaterian A, Borboa A, Coimbra R, Baird A, Eliceiri B P: Non-invasive detection of spatio-temporal activation of SBE and NFAT5 promoters in transgenic reporter mice following stroke. *Neuropathology* 2012, 32(2):118-123.
67. Paban V, Ogier M, Chambon C, Femandez N, Davidsson J, Risling M, A lescio-Lautier B: Molecular gene expression following blunt and rotational models of traumatic brain injury parallel injuries associated with stroke and depression. *J Transl Sci*, 2016, 2(6):330-339.
68. Yilmaz G, Granger O N: Leukocyte recruitment and ischemlc brain injury. *Neurmolecular Med* 2010, 12(2):193-204.
69. Kannan A K, Kim D G, August A, Bynoe M S: Itk signals promote neuroinflammation by regulating CD4+ T-cell activation and trafficking. *J Neurosci* 2015, 35(1):221-233.
70. Ghosh S, Bienemann K, Boztug K, Borkhardt A: Interleukin-2-inducible T-cell kinase (ITK) deficiency—clinical and molecular aspects. *J Clin Immunol* 2014, 34(8):892-899.
71. Toker A, Cantley L C: Signalling through the lipid products of phosphoinositide-3-0H kinase. *Nature* 1997, 387(6634):673-676.
72. Irvine R F, Schell M J: Back in the water: the return of the inositol phosphates. *Nat Rev Mo/Cell Biol* 2001, 2(5):327-338.
73. Vanhaesebroeck B, Leevers S J, Ahmadi K, Timms J, Katso R, Driscoll P C, Woscholski R, Parker P J, Waterfield M D: Synthesis and function of 3-phosphorylated inositol lipids. *Annu Rev Biochem* 2001, 70:535-602.
74. Strange K: Regulation of solute and water balance and cell volume in the central nervous system. *J Am Soc Nephrol* 1992, 3(1):12-27.
104. Zhao L, Li H, Guo R, Ma T, Hou R, Ma X, Du Y: miR-137, a new target for post-stroke depression? *Neurol Regen Res* 2013, 8(26):2441-2448.
105. Meissner L, Gallozzi M, Balbi M, Schwarzmaier S, Tiedt S, Terpolilli N A, Plesnila N: TemporalProfile of MicroRNA Expression in Contused Cortex after Traumatic Brain Injury in Mice. *J Neurolrauma* 2016, 33(8):713-720.
106. Sun L, Liu A, Zhang J, Ji W, Li Y, Yang X, Wu Z, Guo J: miR-23b improves cognitive impairment s in traumatic brain injury by targeting ATG12-mediated neuronal autophagy. *Behav Brain Res* 2016.
107. Sun L, Zhao M, Wang Y, Liu A, Lv M, Li Y, Yang X, Wu Z: Neuroprotective effects of miR-27a against traumatic brain injury via suppressing Fox03a-mediated neuronal autophagy. *Biochem Biophys Res Commun* 2017, 482(4):1141-1147.
108. Tilley S K, Joseph R M, Kuban K C K, Dammann O U, O'Shea™, Fry R C: Genomic biomarkers of prenatal intrauterine inflammation in umbilical cord tissue predict later life neurological outcomes. *PLoS One* 2017, 12(5):e0176953.
109 Oliver P L, Chodroff R A, Gosal A, Edwards B, Cheung A F, Gomez-Rodriguez J, Elliot G, Garrett U, Lickiss T, Szele F et al: Disruption of Visc-2, a Brain-Ex pressed Conserved Long Noncoding RNA, Does Not Elicit an Overt Anatomical or Behavioral Phenotype. *Cereb Cortex* 2015, 25(10):3572-3585.
110 Gong Y N, Chen G W, Chen C J, Kuo R L, Shih S R: Computational analysis and mapping of novel open reading frames in influenza A viruses. *PLoS One* 2014, 9(12):e115016.
111. Podvin S, Miller M C, Rossi R, Chukwueke J, Donahue J E, Johanson C E, Baird A, Stopa E G: The Orphan C2orf40 Gene is a Neuroimmune Factor in Alzheimer's Disease. *JSM Alzheimers Dis Relat Dement* 2016, 3(1).

The invention claimed is:
1. A method for diagnosing and treating traumatic brain injury (TBI), wherein the method comprises assaying a biological sample from a patient in need of TBI diagnosis comprising nucleic acids to determine a frequency or percentage methylation of cytosine at two or more loci throughout genome;

comparing the cytosine methylation level of the sample to cytosine methylation level of a control sample thereby diagnosing TBI in the patient, wherein the control sample is a corresponding biological sample from a healthy subject wherein difference in cytosine methylation level between the biological sample and control sample at two or more loci is greater than 2%, and wherein the two or more loci comprise two or more of the following loci: cg06393885, cg20569893, cg00611535, and/or cg16882751; and treating the patient, wherein treating the patient comprises cognitive and physical rest and aerobic treatment, post traumatic headache management and treatment, cognitive impairment treatment, vestibulo-oculomotor dysfunction treatment, or sleep deprivation treatment.

2. The method of claim 1, wherein the method further comprises extracting nucleic acids from the biological sample.

3. The method of claim 1, wherein the TBI comprises chronic traumatic encephalopathy (CTE), recurrent TBI, or mild TBI (mTBI).

4. The method of claim 1, wherein the method further comprises calculating the patient's risk of TBI based on the cytosine methylation level at different sites throughout the genome.

5. The method of claim 1, wherein the biological sample comprises body fluid or a tissue obtained from the patient.

6. The method of claim 1, wherein the biological sample comprises blood, plasma, serum, cerebral spinal fluid, buccal swab, saliva, sputum, urine, tear, sweat, or hair.

7. The method of claim 1, wherein the biological sample is from a patient of greater than 19 years old or wherein the biological sample is from a pediatric patient.

8. The method of claim 1, wherein the nucleic acids comprise cellular nucleic acids or wherein the nucleic acids comprise cell free nucleic acids.

9. The method of claim 1, wherein each of the loci comprises an AUC of 0.75 or greater, 0.80 or greater, 0.85 or greater, 0.90 or greater, or 0.95 or greater.

10. The method of claim 1, wherein the assay is a bisulfite-based methylation assay or a whole genome methylation assay.

11. The method of claim 1, wherein measurement of the frequency or percentage methylation of cytosine nucleotides is obtained using single gene or whole genome sequencing techniques.

12. A method of claim 1, wherein the method further comprises assaying proteins encoded by the nucleic acids comprising the differentially methylated CpG loci, or assaying mRNA comprising the differentially methylated CpG loci.

13. The method of claim 1, wherein the method further comprises assaying for one or more metabolomic markers.

14. The method of claim 1, wherein the method further comprises using artificial intelligence techniques.

15. The method of claim 14, wherein using artificial intelligence techniques comprises using one or more of the following machine learning algorithms: Random Forest (RF), Support Vector Machine (SVM), Linear Discriminant Analysis (LDA), Prediction of Analysis for Microarrays (PAM), Generalized Linear Model (GLM), or deep learning (DL).

16. The method of claim 1, wherein the two or more loci comprise cg06393885, cg20569893, cg00611535, and cg16882751.

17. The method of claim 1, wherein the loci further comprise one or more of the following loci: cg24402518, cg20601481, cg05138188, cg27384352, cg24684739, cg13528854, cg24104241, cg24684739, cg18419977, cg07077221, cg03957481, cg19470964, cg06233996, cg24742298, cg15531403, and cg16117781.

18. The method of claim 16, wherein the loci further comprise one or more of the following loci: cg24402518, cg20601481, cg05138188, cg27384352, cg24684739, cg13528854, cg24104241, cg24684739, cg18419977, cg07077221, cg03957481, cg19470964, cg06233996, cg24742298, cg15531403, and cg16117781.

* * * * *